(12) United States Patent
Wilkie et al.

(10) Patent No.: US 9,986,723 B2
(45) Date of Patent: Jun. 5, 2018

(54) SCREEN AND USE OF THERAPEUTICS FOR PANCREATIC DUCTAL ADENOCARCINOMA

(71) Applicant: The Board of Regents of the University of Texas System, Austin, TX (US)

(72) Inventors: Thomas M. Wilkie, Dallas, TX (US); Rolf A. Brekken, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days. days.

(21) Appl. No.: 14/920,195

(22) Filed: Oct. 22, 2015

(65) Prior Publication Data

US 2016/0128311 A1 May 12, 2016

Related U.S. Application Data

(60) Provisional application No. 62/067,276, filed on Oct. 22, 2014, provisional application No. 62/067,304, filed on Oct. 22, 2014, provisional application No. 62/232,901, filed on Sep. 25, 2015, provisional application No. 62/232,922, filed on Sep. 25, 2015.

(51) Int. Cl.
| | |
|---|---|
| A01K 67/027 | (2006.01) |
| A61K 31/337 | (2006.01) |
| A61K 31/7068 | (2006.01) |
| A61K 31/366 | (2006.01) |
| A61K 31/502 | (2006.01) |
| A61K 49/00 | (2006.01) |
| C12Q 1/68 | (2018.01) |
| G01N 33/574 | (2006.01) |
| A61K 31/00 | (2006.01) |

(52) U.S. Cl.
CPC ...... *A01K 67/0278* (2013.01); *A01K 67/0275* (2013.01); *A61K 31/00* (2013.01); *A61K 31/337* (2013.01); *A61K 31/366* (2013.01); *A61K 31/502* (2013.01); *A61K 31/7068* (2013.01); *A61K 49/0008* (2013.01); *C12Q 1/6886* (2013.01); *G01N 33/57438* (2013.01); *A01K 2217/056* (2013.01); *A01K 2227/105* (2013.01); *A01K 2267/0331* (2013.01); *C12Q 2600/106* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

2008/0242742 A1* 10/2008 Depinho ............ A01K 67/0276
514/789

OTHER PUBLICATIONS van Blesen et al., Receptor-tyrosine-kinase- and Gpy-medlated MAP kinase activation by a common signalling pathway Nature vol. 376 Aug. 31, 1995; pp. 781-784.*
Kahn et al Is the model of signal amplification by GPCRs/GEFs activating multiple GTPases relevant to a broad spectrum of heterotrimeric and RAS superfamily GTPases? Cellular Logistics 4:2, e943602; Apr.-Jun., 2014; pp. 1-5.*
Wu et al Recurrent GNAS Mutations Define an Unexpected Pathway for Pancreatic Cyst DevelopmentSci Transl Med. Jul. 20, 2011; 3(92): 92ra66 pp. 1-18.*
Kim et al RGS16 and FosB underexpressed in pancreatic cancer with lymph node metastasis promote tumor progression Tumor Biology Oct. 2010, vol. 31, Issue 5, pp. 541-548.*
Kim et al gGS16 and FosB underexpressed in pancreatic cancer with lymph node metastasis promote tumor progression Tumor Biol (2010) 31:541-548.*
Chan et al BRAF and KRAS Mutations in Colorectal Hyperplastic Polyps and Serrated Adenomas Cancer Research 2003. pp. 4878-4881.*
RGS16 and FosB underexpressed in pancreatic cancer with lymph node metastasis promote tumor progressionTumor Biol. (2010) 31:541-548.*
Villasenor et al., Rgs16 and Rgs8 in embryonic endocrine pancreas and mouse models of diabetes Disease Models & Mechanisms 3, 567-580 (2010).*
Aguirre et al., "Activated Kras and *Ink4a/Arf* deficiency cooperate to produce metastatic pancreatic ductal adenocarcinoma," *Genes & Dev.*, 17:3112-3126, 2003.
Byers et al., "An epithelial-mesenchymal transition gene signature predicts resistance to EGFR and PI3K inhibitors and identifies Axl as a therapeutic target for overcoming EGFR inhibitor resistance," *Clin Cancer Res*, 19: 279-290, 2013.
Frese et al., "nab-Paclitaxel potentiates gemcitabine activity by reducing cytidine deaminase levels in a mouse model of pancreatic cancer," *Cancer Discov*, 2:260-269, 2012.
Gjerdrum et al., "Axl is an essential epithelial-to-mesenchymal transition-induced regulator of breast cancer metastasis and patient survival," *Proc. Nat'l Acad. Sci.USA*, 107:1124-1129, 2010.
Gong et al., "A gene expression atlas of the central nervous system based on bacterial artificial chromosomes," *Nature*, 425:917-925, 2003.
Hruban et al., "Progression model for pancreatic cancer," *Clin Cancer Res*, 6:2969-2972, 2000.
Kirane et al., "Warfarin Blocks Gas6-Mediated Axl Activation Required for Pancreatic Cancer Epithelial Plasticity and Metastasis," *Cancer Res.*, 75(18):3699-3705, 2015.
Lew et al., "Differential TAM receptor-ligand-phospholipid interactions delimit differential TAM bioactivities," *Elife*, 3:e03385, 2014.

(Continued)

*Primary Examiner* — Maria Leavitt
(74) *Attorney, Agent, or Firm* — Parker Highlander PLLC

(57) ABSTRACT

The present disclosure relates to methods for screening compounds for treating pancreatic ductal adenocarcinoma (PDA) using a mouse model with an Rgs16::GFP reporter. Also described are combination therapies for treating pancreatic ductal adenocarcinoma (PDA) using taxanes, gemcitabine and an Axl kinase inhibitor.

3 Claims, 34 Drawing Sheets
(28 of 34 Drawing Sheet(s) Filed in Color)

(56) References Cited

OTHER PUBLICATIONS

Linger et al., "TAM receptor tyrosine kinases: biologic functions, signaling, and potential therapeutic targeting in human cancer,"*Advances in Cancer Research*, 100:35-83, 2008.

Maitra et al., "Precursors to invasive pancreatic cancer," *Adv Anat Pathol*, 12:81-91, 2005.

Masellis et al., "Successful treatment of metastatic pancreatic adenocarcinoma with combination chemotherapy regimens," *Int J Clin Oncol*, 14:478-481, 2009.

Neesse et al., "SPARC independent drug delivery and antitumour effects of nab-paclitaxel in genetically engineered mice," *Gut*, 63:974-983, 2014.

Ocal et al., "A rapid in vivo screen for pancreatic ductal adenocarcinoma therapeutics," *Dis Model Mech.*, 8(10):1201-1211, 2015.

Ocal et al., "Rapid in vivo screen of pancreatic ductal adenocarcinoma (PDA) therapeutics," Poster, Texas Fresh Air, Oct. 23, 2014.

Ocal et al., "Rapid in vivo screen of pancreatic ductal adenocarcinoma (PDA) therapeutics," Poster, AACR Pancreas Cancer New Orleans, May 18, 2014.

Ocal et al., "Rapid in vivo screen of pancreatic ductal adenocarcinoma (PDA) therapeutics," Poster—RAS Oncognees: From Biology to Therapy, American Association for Cancer Research Special Conference, Lake Buena Vista, Florida, Feb. 24, 2014.

Paolino et al., "The E3 ligase Cbl-b and TAM receptors regulate cancer metastasis via natural killer cells," *Nature*, 507:508-512, 2014.

Pashkov et al., "Regulator of G protein signaling (*Rgs16*) inhibits hepatic fatty acid oxidation in a ChREBP-dependent manner," *J Biol Chem*, 286:15116-15127, 2011.

Reichl et al., "Multicenter analysis of soluble Axl reveals diagnostic value for very early stage hepatocellular carcinoma," *Int J Cancer.*, 137(2):385-394, 2014.

Schmidt et al., "Macrophage-tumor crosstalk: role of TAMR tyrosine kinase receptors and of their ligands," *Cellular and Molecular Life Sciences*, 69:1391-1414, 2012.

Song et al., "Overexpression of receptor tyrosine kinase Axl promotes tumor cell invasion and survival in pancreatic ductal adenocarcinoma," *Cancer*, 117:734-743, 2011.

Villasenor et al., "Rgs16 and Rgs8 in embryonic endocrine pancreas and mouse models of diabetes," *Disease Models & Mechanisms*, 3:567-580, 2010.

Von Hoff et al., "Increased survival in pancreatic cancer with nab-paclitaxel plus gemcitabine," *The New England Journal of Medicine*, 369:1691-1703, 2013.

Wilkie, "$G_{q/11\text{-}Rgs}$ signaling in diabetes, malnutrition and pancreatic cancer," Presentation, ASPET Symposium, San Diego, Apr. 15, 2014.

Wilson et al., "AXL inhibition sensitizes mesenchymal cancer cells to antimitotic drugs," *Cancer Res.*, 74(20):5878-90, 2014.

\* cited by examiner

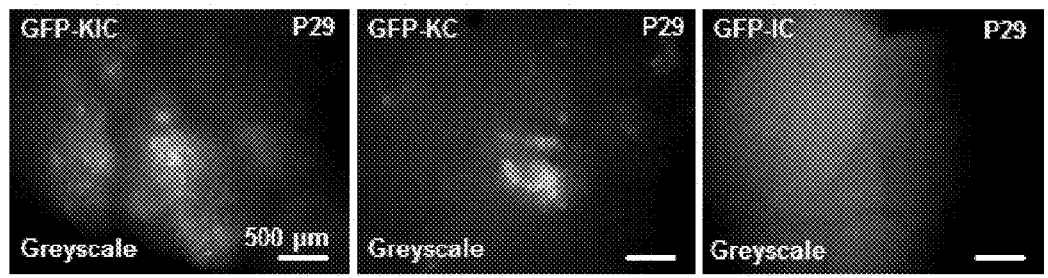
FIG. 1
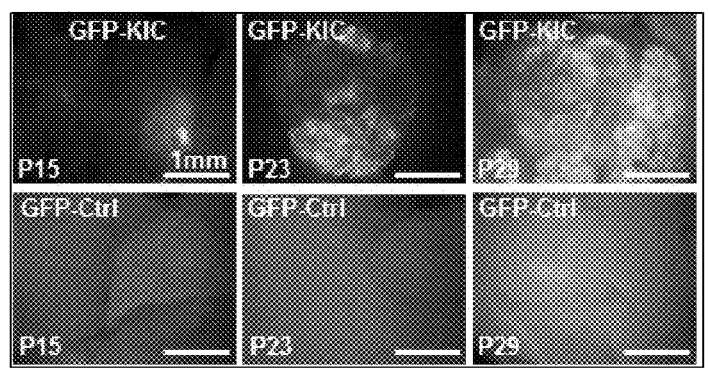
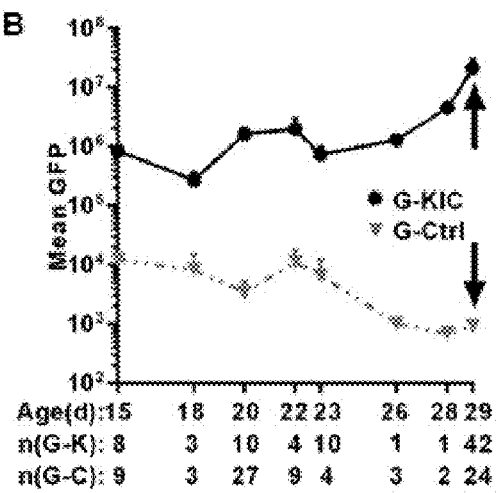
FIGS. 2A-B

|  | NT (n = 27) | GA (n = 12) | p-value | BGA (n = 15) | p-value | WGA (n = 14) | p-value |
|---|---|---|---|---|---|---|---|
| Mean | 6.33 | 5.69 | 0.0007 | 5.86 | 0.0085 | 5.70 | 0.0042 |
| Median* | 6.31 | 5.81 | 0.0048 | 6.06 | 0.0498 | 5.84 | 0.0195 |
| Range | 1.18 | 2.15 | 0.0263 | 1.73 | 0.1628 | 1.57 | 0.0848 |
| IQR | 0.55 | 0.69 | 0.4044 | 0.64 | 0.6763 | 0.70 | 0.2927 |
| Lowest / Highest Log GFP | 0.83 | 0.69 | 0.0087 | 0.74 | 0.1040 | 0.75 | 0.0445 |
| Lowest / Median NT Log GFP[#] | 0.91 | 0.73 | 0.0010 | 0.77 | 0.0316 | 0.76 | 0.0124 |
| Highest / Median NT Log GFP[#] | 1.10 | 1.07 | 0.5341 | 1.04 | 0.0739 | 1.01 | 0.0327 |
| Highest / Median GA Log GFP[#] | - | 1.16 | - | 1.14 | 0.6415 | 1.10 | 0.2819 |
| Highest / Median BGA Log GFP[#] | - | - | - | 1.09 | - | 1.05 | 0.2751 |

FIG. 7

|  | NT (n = 46) | G (n = 33) | p-value | WG (n = 33) | p-value |
|---|---|---|---|---|---|
| Mean | 6.07 | 5.87 | 0.0160 | 5.70 | 0.0001 |
| Median* | 6.03 | 5.85 | 0.0303 | 5.74 | 0.0005 |
| Range | 0.74 | 0.84 | 0.2495 | 0.98 | 0.0274 |
| IQR | 0.39 | 0.36 | 0.6320 | 0.41 | 0.6903 |
| Lowest / Median NT Log GFP[#] | 0.95 | 0.91 | 0.0152 | 0.87 | <0.0001 |
| Highest / Median NT Log GFP[#] | 1.07 | 1.05 | 0.1472 | 1.03 | 0.0158 |
| Highest / Median G Log GFP[#] | - | 1.08 | - | 1.07 | 0.4451 |

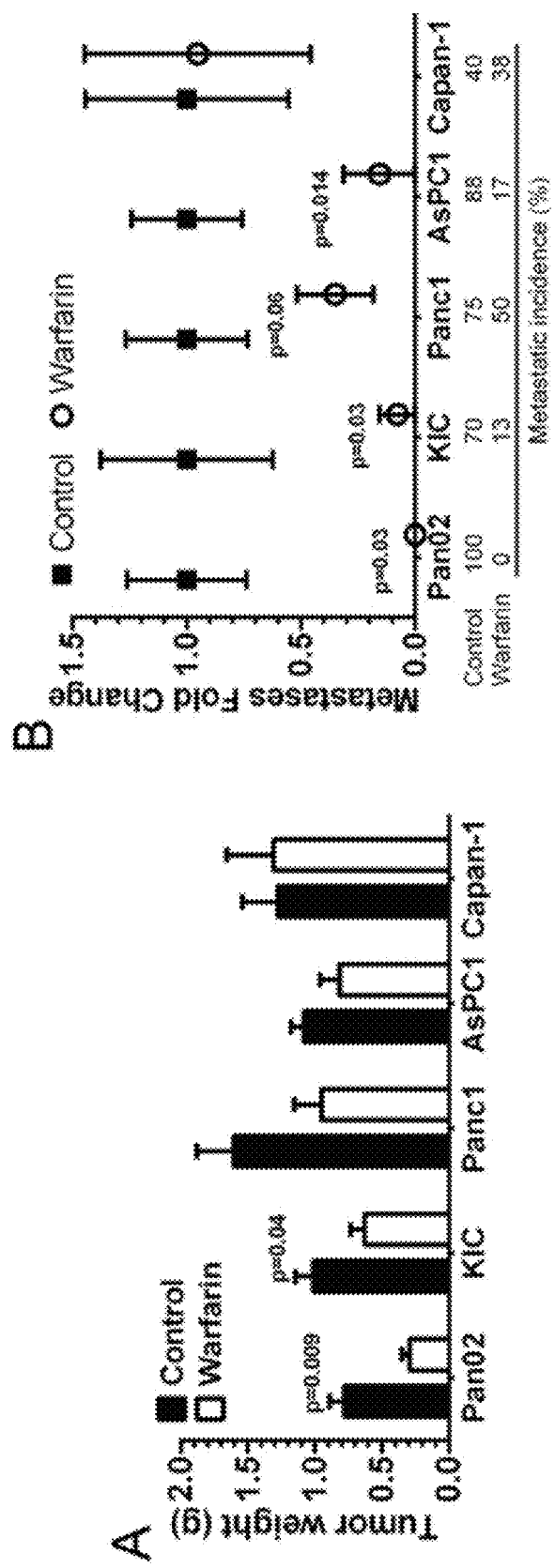
FIGS. 23A-B

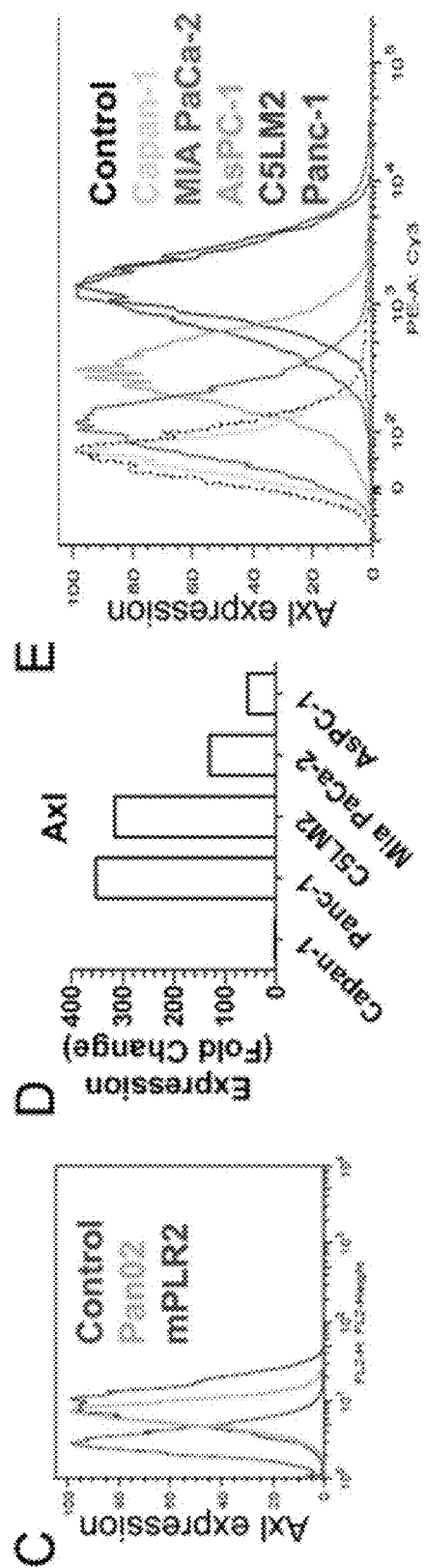
FIGS. 23C-E

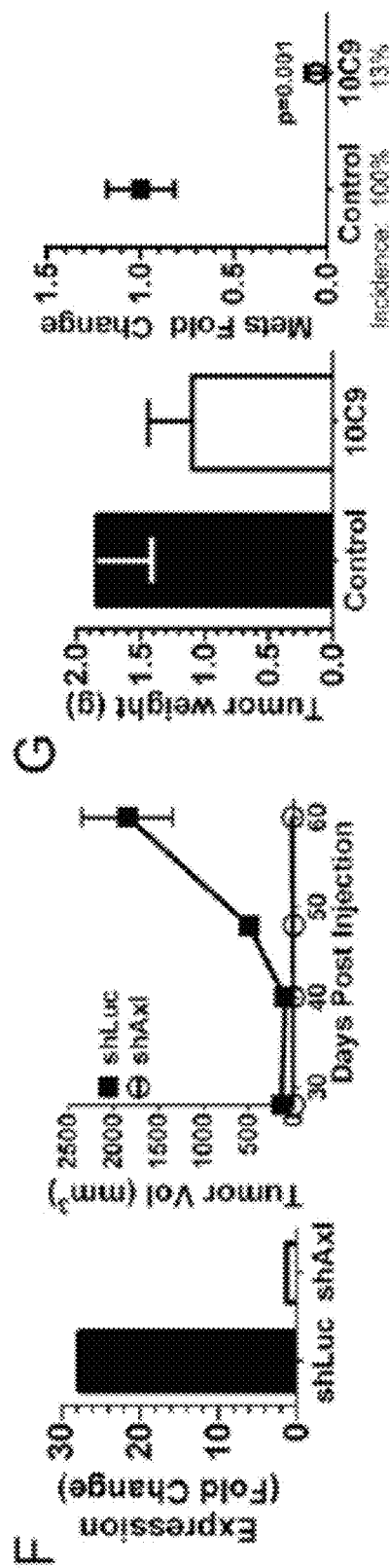
FIGS. 23F-G

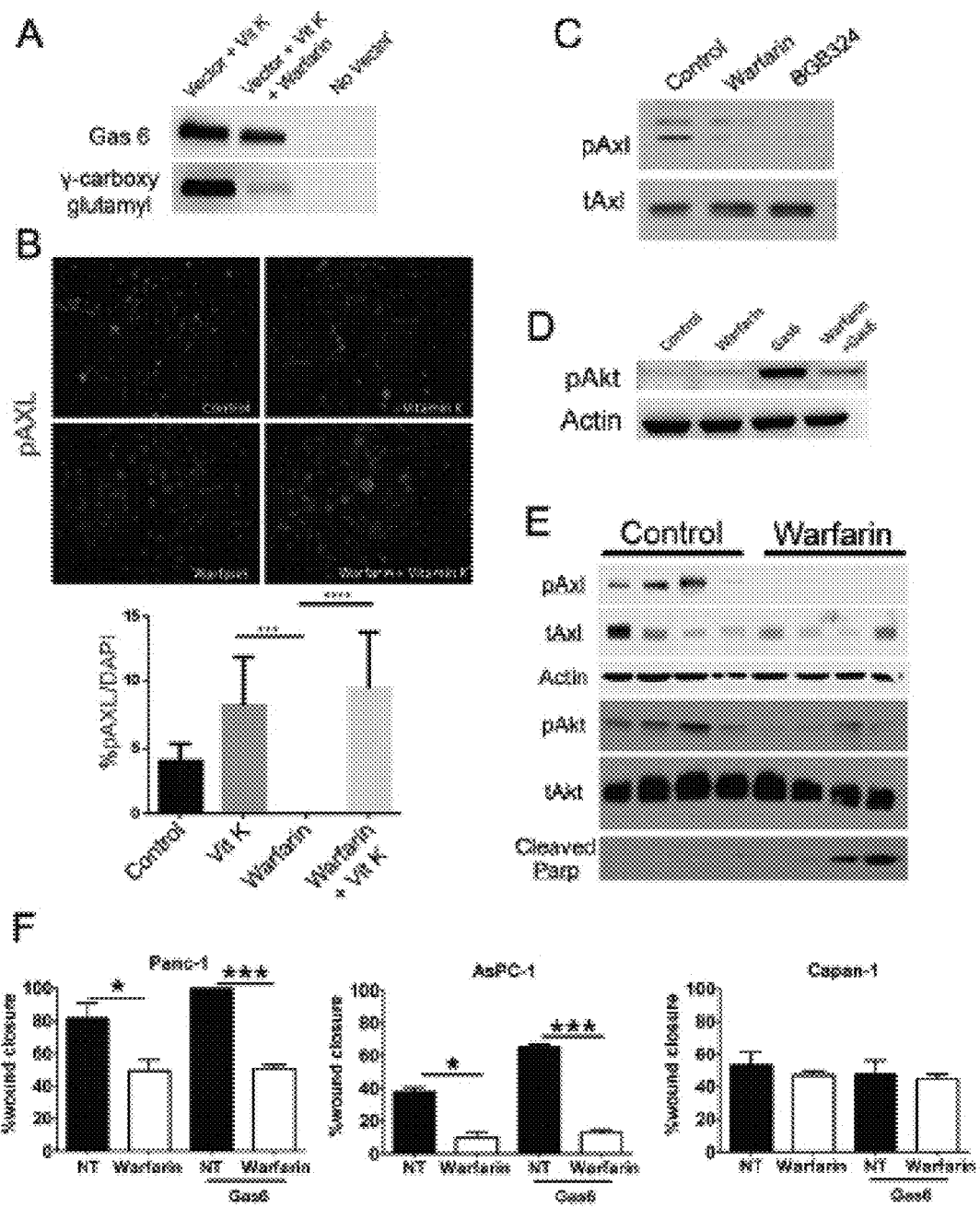
FIGS. 24A-F

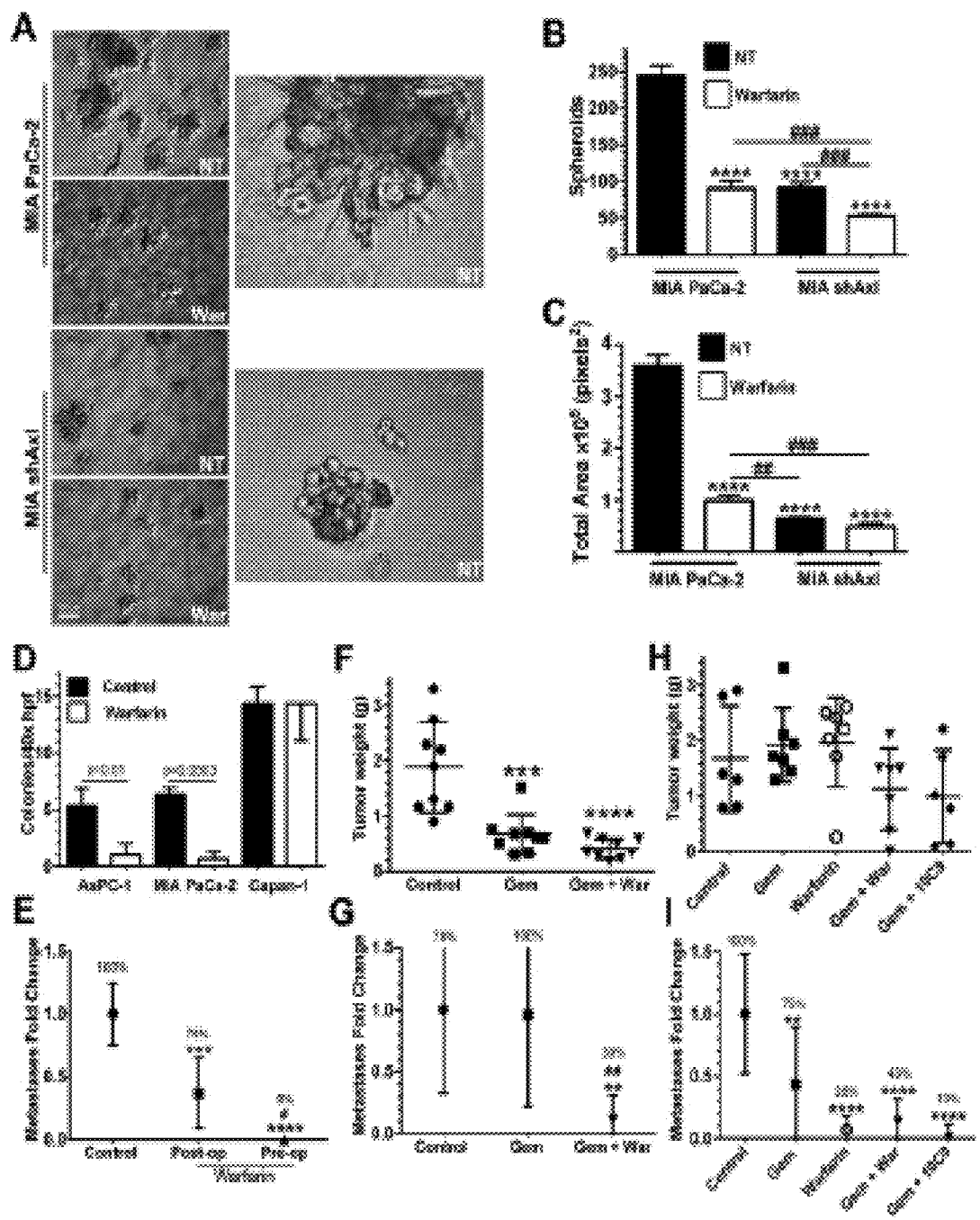
FIGS. 25A-I

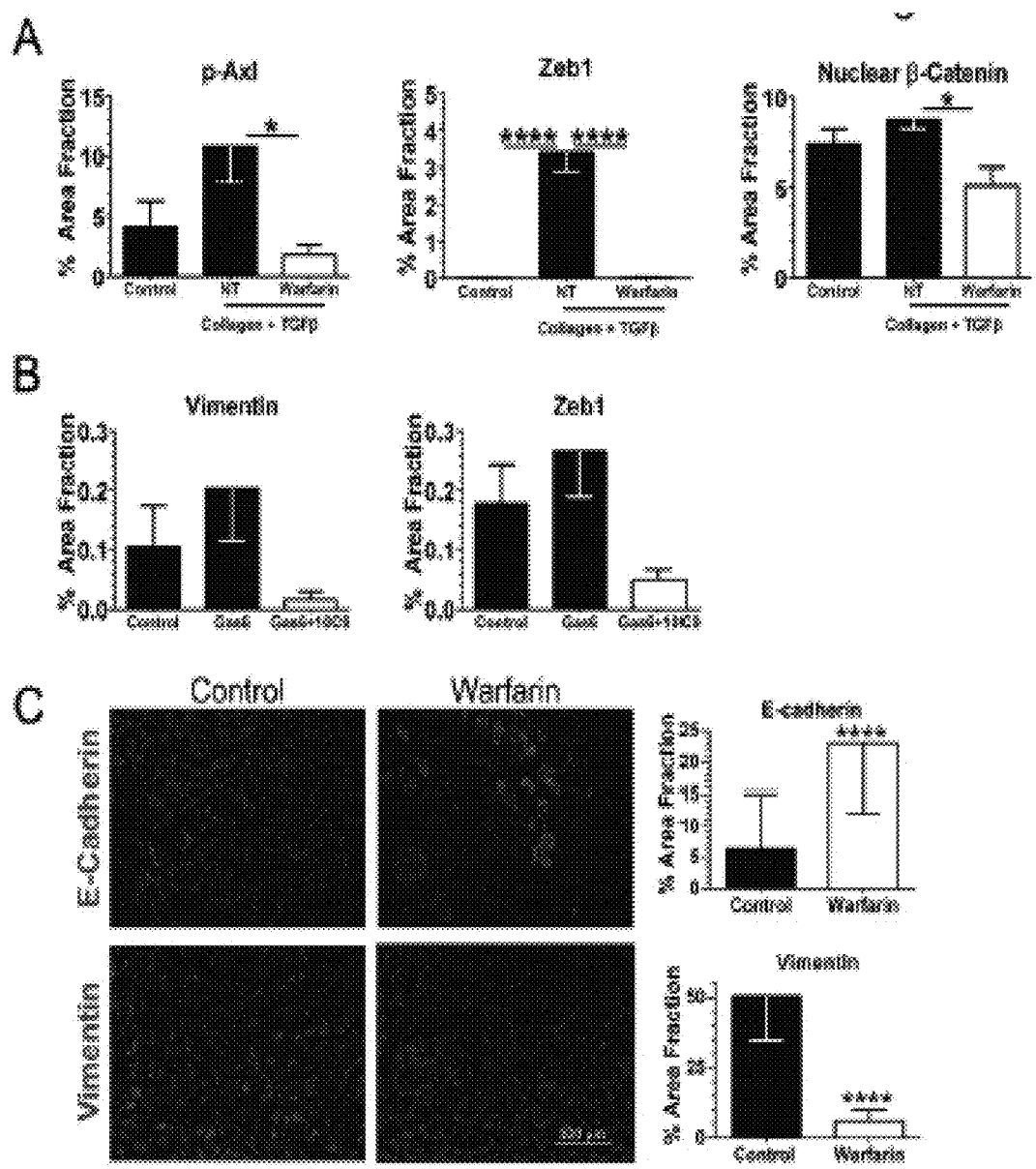
FIGS. 26A-C

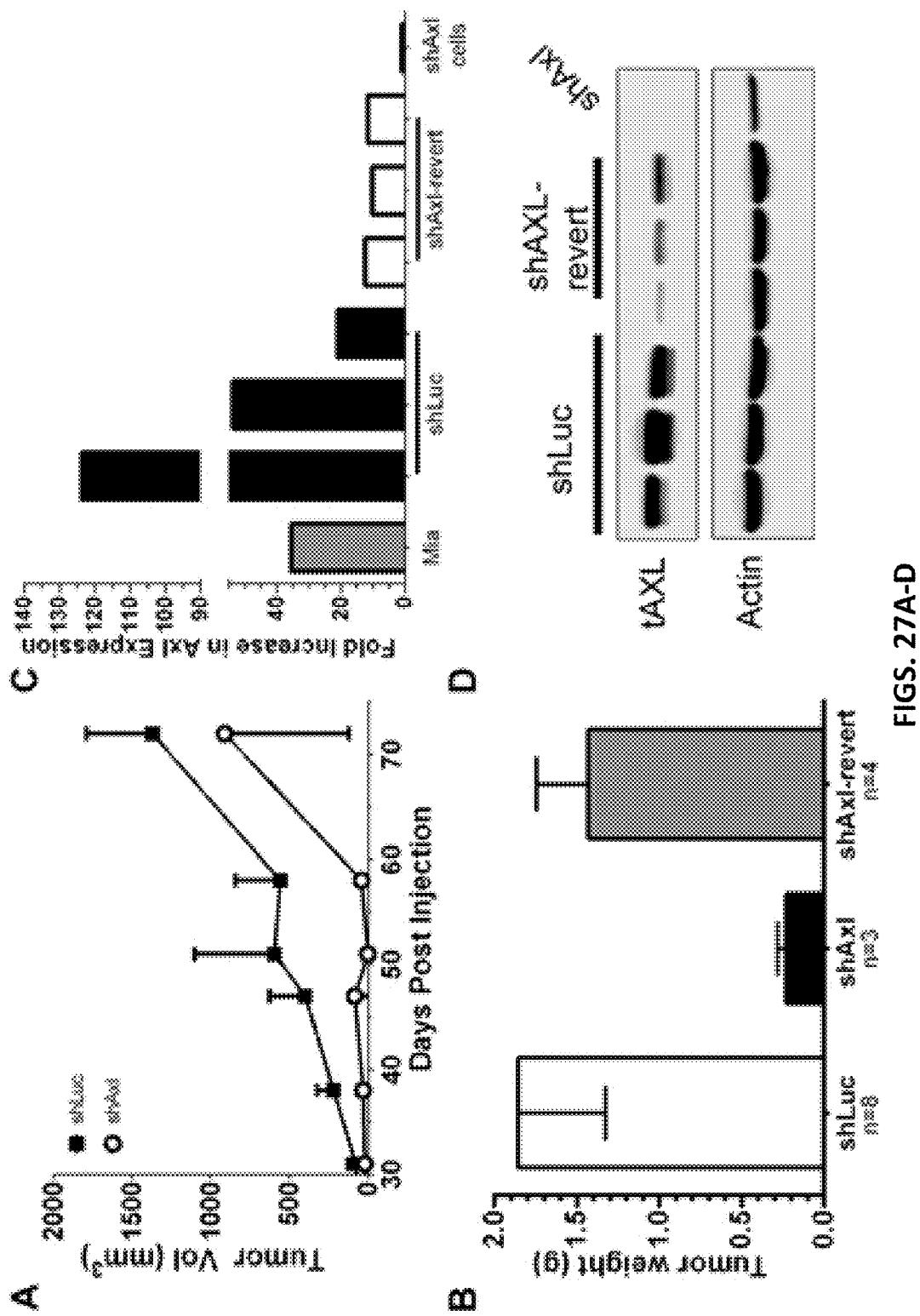
FIGS. 27A-D

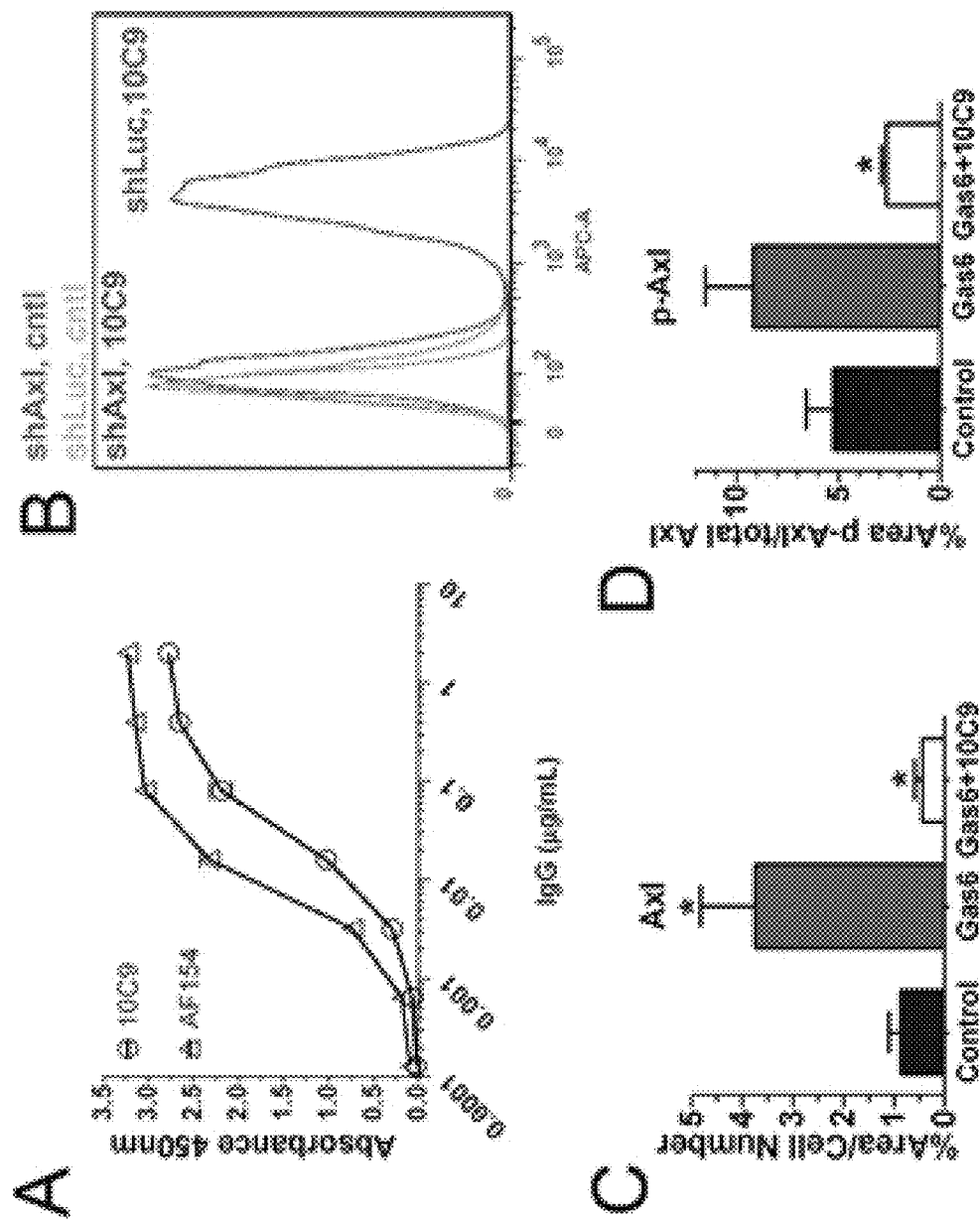
FIGS. 28A-D

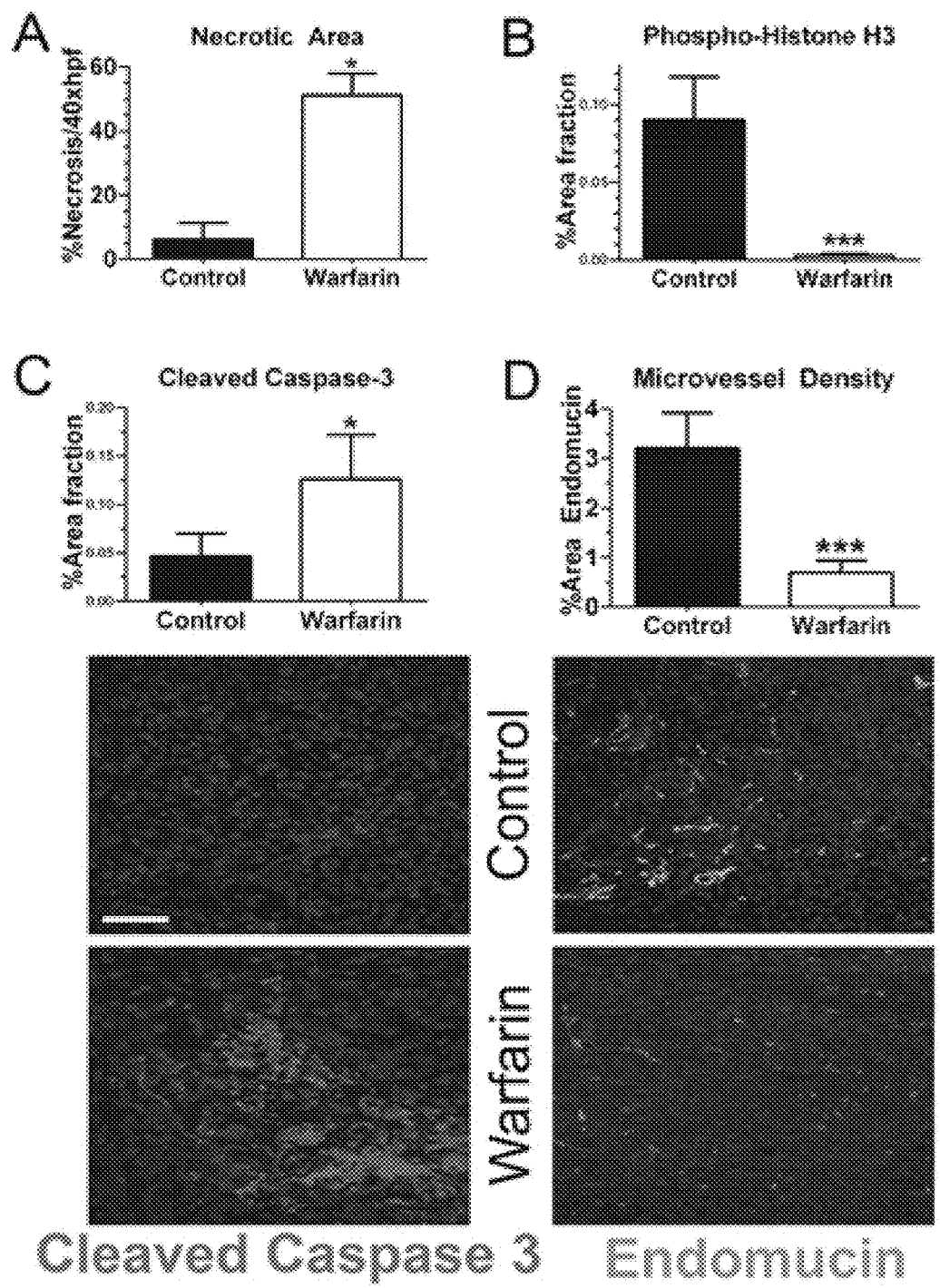
FIGS. 30A-D

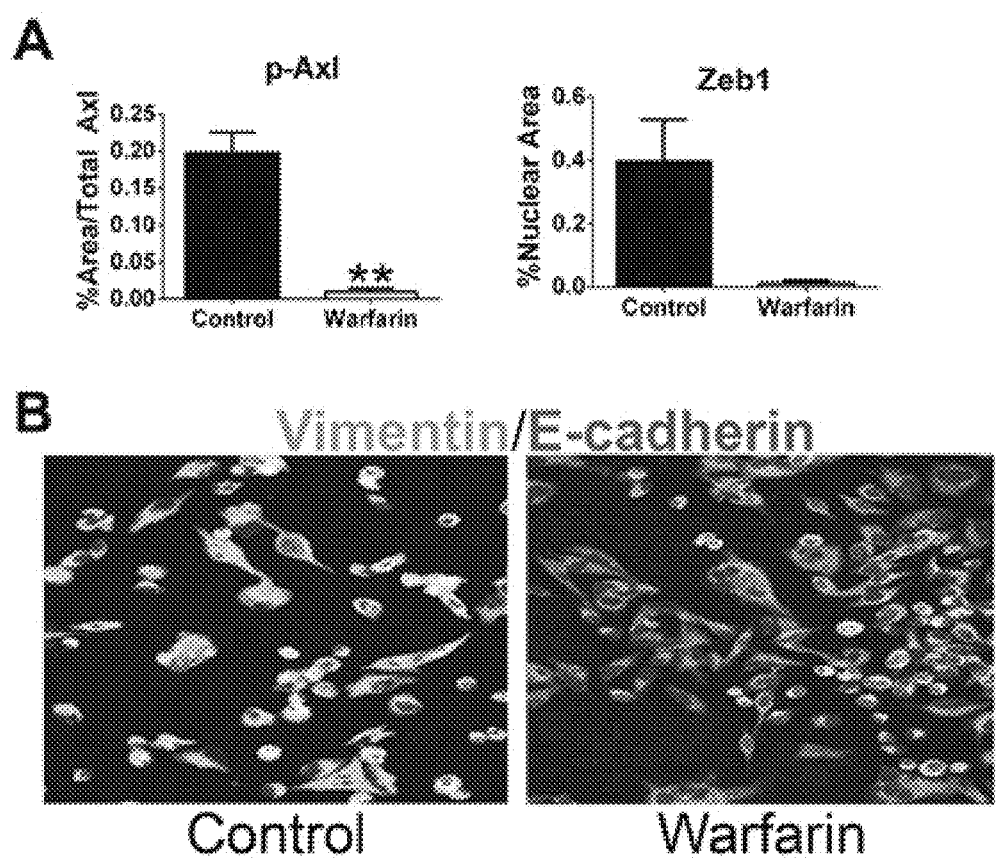
FIGS. 31A-B

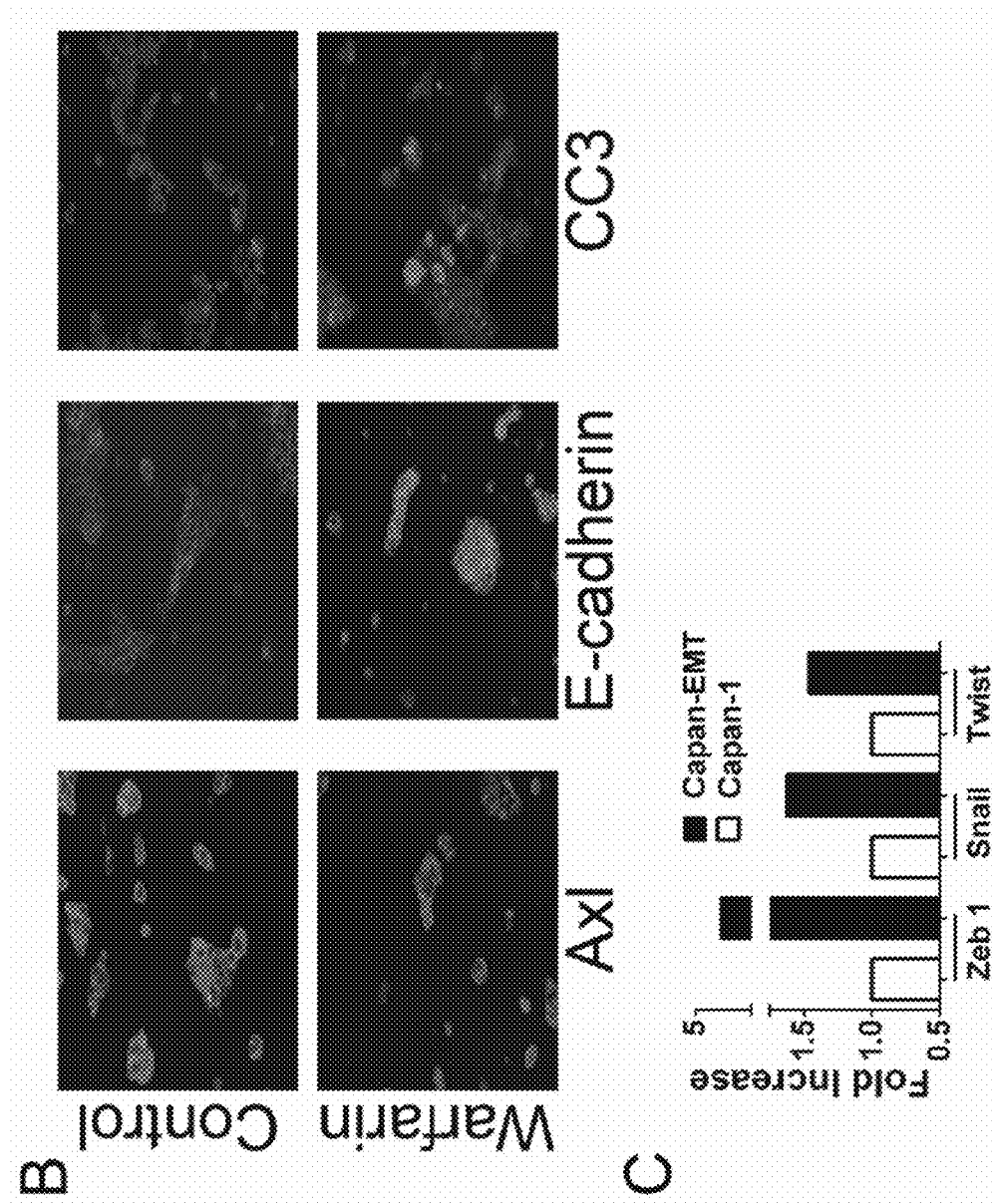
FIGS. 32B-C

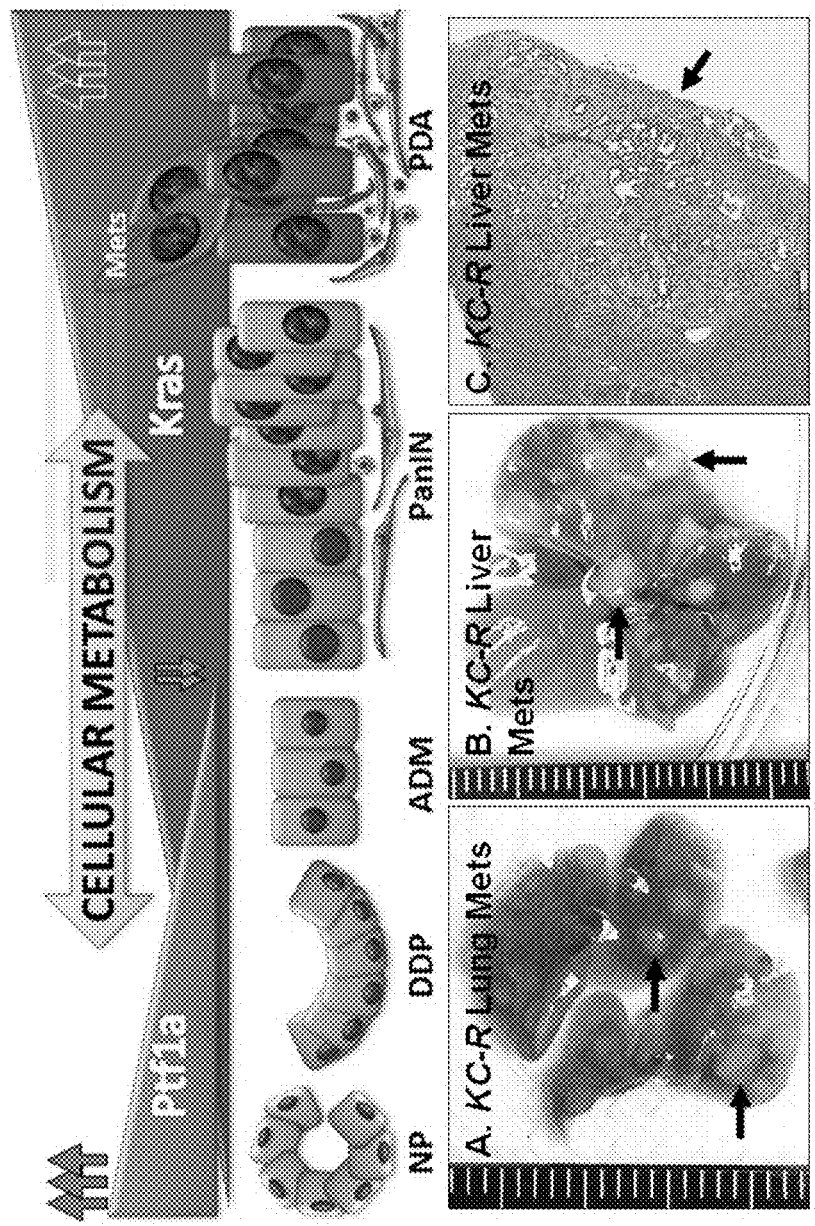
FIGS. 33A-C

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Synthetic Primer

<400> SEQUENCE: 1
cctggaaaat gcttctgtcc g                                           21

<210> SEQ ID NO 2
<211> LENGTH: 21
<212> TYPE: DNA
<213> ORGANISM: Artificial Sequence
<220> FEATURE:
<223> OTHER INFORMATION: Synthetic Primer
```

```
<400> SEQUENCE: 2
cagggtgtta taagcaatcc c                                           21

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3
ctagccacca tggcttgagt                                             20

<210> SEQ ID NO 4
<211> LENGTH: 23
<212> TYPE: DNA
<213> ORGANISM: Artificial Sequence
<220> FEATURE:
<223> OTHER INFORMATION: Synthetic Primer

<400> SEQUENCE: 4
tccgaattca gtgactacag atg                                         23

<210> SEQ ID NO 5
<211> LENGTH: 24
<212> TYPE: DNA
<213> ORGANISM: Artificial Sequence
<220> FEATURE:
<223> OTHER INFORMATION: Synthetic Primer

<400> SEQUENCE: 5
ttgttggccc aggatgccga catc                                        24

<210> SEQ ID NO 6
<211> LENGTH: 23
<212> TYPE: DNA
<213> ORGANISM: Artificial Sequence
<220> FEATURE:
<223> OTHER INFORMATION: Synthetic Primer

<400> SEQUENCE: 6
ccaagtgtgc aaacccaggc tcc                                         23

<210> SEQ ID NO 7
<211> LENGTH: 62
<212> TYPE: DNA
<213> ORGANISM: Artificial Sequence
<220> FEATURE:
<223> OTHER INFORMATION: Synthetic oligonucleotide

<400> SEQUENCE: 7
gacatcctct ttctcctgcg aagcccatct ggtcatgggc ttcgcaggag aaagaggatg    60
tc                                                                 62

<210> SEQ ID NO 8
<211> LENGTH: 64
<212> TYPE: DNA
<213> ORGANISM: Artificial Sequence
<220> FEATURE:
<223> OTHER INFORMATION: Synthetic oligonucleotide
```

```
<400> SEQUENCE: 8
gattatgtcc ggttatgtaa acaatccggc tggtcccgga ttgtttacat aaccggacat        60
aatc                                                                     64
```

SCREEN AND USE OF THERAPEUTICS FOR PANCREATIC DUCTAL ADENOCARCINOMA

The present application claims benefit of priority to U.S. Provisional Application Ser. Nos. 62/067,276 and 62/067,304 filed Oct. 22, 2014, and Provisional Application Ser. Nos. 62/232,901 and 62/232,922, filed Sep. 25, 2015, the entire contents of all applications being hereby incorporated by reference.

BACKGROUND

I. Technical Field

The present disclosure relates generally to the fields of medicine and oncology genetics. More particularly, it relates to the use of mouse models to screen for pancreatic ductal adenocarcinoma therapeutics, and the use of such therapeutics, alone or in combination, to treat pancreatic ductal adenocarinoma.

II. Related Art

Pancreatic ductal adenocarcinoma (PDA) is the 4$^{th}$ leading cause of cancer-related deaths but is predicted to become more common due to its association with smoking, diet, obesity, and type 2 diabetes (Pannala et al., 2008; Rahib et al., 2014; Siegel et al., 2015). Three major classifications of pancreatic precancerous lesions are associated with progression to PDA: PanIN (pancreatic intraepithelial neoplasia), IPMN (intraductal papillary mucinous neoplasm) and MCN (mucinous cystic neoplasm) (Distler et al., 2014). Precancerous lesions can be common in the elderly or obese. For example, early PanINs were found in 65% of obese patients, associated with intravisceral fat and pancreatic intralobular fibrosis and fat (Rebours et al., 2015). IPMN are next most commonly associated with PDA. They are found in the pancreatic main and branching ducts. MCN occur predominately in the peripheral pancreas in females.

Recent mathematical predictions attribute spontaneous mutations during cell division as initiators of PDA, making early detection and effective therapy the only two elements determining survival (Tomasetti and Vogelstein, 2015). Unfortunately, PDA symptoms present late, and other than surgical resection, limited progress has been made in developing effective treatment after gemcitabine was introduced as first-line therapy for advanced PDA (Burris et al., 1997). Gemcitabine treatment alone or after resection is marginally effective in prolonging survival. One of the two predominant therapeutic regimens is gemcitabine combined with nab-paclitaxel (Abraxane), which was shown to increase survival to 8.5 months compared with 6.7 months for patients who received gemcitabine alone (Von Hoff et al., 2013). In a follow up study, 12 patients were still alive after 42 months of treatment (Goldstein et al., 2015). In addition to interfering with microtubule function, Abraxane augments gemcitabine efficacy by reducing the level of its metabolizing enzyme, cytidine deaminase (Ibrahim et al., 2002; Frese et al., 2012). However, tumors are often resistant to this combination (Neesse et al., 2014). The other common drug treatment, FOLFIRINOX, consisting of four different chemotherapy agents, is more effective but less well tolerated (Becker et al., 2014; Moorcraft et al., 2014). Therefore, there is a need for a systematic and robust in vivo screen that can accelerate the pace of discovery for improved PDA therapeutics.

PDA initiates as ductal neoplasia, derived from any of three pancreatic adult cell types—ductal progenitor cells, centroacinar cells, or acinar cells that have undergone acinar to ductal metaplasia (ADM) (Bonner-Weir et al., 2004; Rovira et al., 2010; von Figura et al., 2014). In humans, activated Kras and inactivated Cdkn2a are the earliest and most common genetic mutations identified in disease progression (Hezel et al., 2006; Iacobuzio-Donahue et al., 2012). Genetically engineered mouse models (GEMM) based on these mutations have been developed to investigate PDA initiation and propagation. In this report, the inventors use KC (p48$^{Cre}$;LSL-Kras$^{G12D}$) and KIC mice (p48$^{Cre}$;LSL-Kras$^{G12D}$;Cdkn2a$^{f/f}$). Both lines form tumors because they express activated Kras$^{G12D}$ (KIC also has inactivation of the tumor suppressor Cdkn2a) in all three pancreatic lineages—ducts, acinar and endocrine cells—under control of the p48 (Ptf1a) promoter. By contrast, IC mice (p48$^{Cre}$;Cdkn2a$^{f/f}$) never form tumors. KIC mice are an excellent GEMM for PDA therapeutic screens because neoplasia develops early, between 2 to 3 weeks of age, and large aggressive tumors develop in all mice by 4 weeks of age (Aguirre et al., 2003).

PDA is the most frequent major cancer harboring Ras mutations (e.g., Kras$^{G12D}$); (Pylayeva-Gupta et al., 2011). Kras mutations are found in over 90% of human PDA (Iacobuzio-Donahue et al., 2012). Kras$^{G12D}$ expression is necessary but not sufficient to initiate neoplasia; GTP binding is required to activate Kras$^{G12D}$ (Huang et al., 2014). Ras guanine nucleotide exchange factors (Ras-GEFs) catalyze GDP dissociation, and subsequent GTP binding to Ras (Jeng et al., 2012). Protein kinase and G-Protein Coupled Receptor (GPCR) signaling can stimulate Ras-GEFs to promote Kras$^{G12D}$-dependent neoplasia (van Biesen et al., 1995; Kahn, 2014). Regulators of G-protein Signaling (RGS) proteins are GTPase activating proteins (GAPs) for the Gi- and Gq-alpha subunits of heterotrimeric G proteins (Berman et al., 1996). Interestingly, RGS-resistant mutations in Gα$_q$ (and Gα$_s$) were found in IPMNs isolated from patients (Wu et al., 2011). RGS proteins are coincidence detectors that can be induced by and integrate multiple inputs to feedback regulate the GPCR arm of the pathway, by virtue of their Gα-GAP activity (Ross and Wilkie, 2000; Huang et al., 2006; Villasenor et al., 2010; Pashkov et al., 2011). The induction of RGS proteins can therefore be monitored to report hyperactivated Ras signaling (Dohlman et al., 1996; Dignard et al., 2008). Because Ras remains an elusive drug target (Stephen et al., 2014), the inventors developed an in vivo screen for PDA therapeutics that is responsive to Kras signaling.

Expression of an Rgs16::GFP bacterial artificial chromosome (BAC) transgene has been shown during embryonic and postnatal pancreas development in pancreatic progenitors, endocrine and duct cells (Villasenor et al., 2010). GFP was expressed in ducts and islet beta cells during neonatal pancreas development but was not detected in euglycemic adult mice. Rgs16::GFP was reactivated, first in ducts, then islet beta cells, under conditions of chronic insulin demand or hyperglycemia in mouse models of type 1 and type 2 diabetes, and during gestation. In humans, Rgs16 expression was observed in ducts of pancreatic cancer patients prior to detectable metastasis (Kim et al., 2010). Chronic stress might induce Rgs16 in progenitor cells within the pancreatic ductal epithelium (Bonner-Weir et al., 2004; Villasenor et al., 2010).

SUMMARY

Thus, in accordance with the present disclosure, there is provided a method of inhibiting pancreatic ductal adenocarcinoma (PDA) in a subject comprising administering to said subject (a) a taxane; (b) gemcitabine; and (c) an Axl kinase inhibitor, in an amount sufficient to inhibit said PDA. The subject may be a human or a non-human mammal. Inhibiting may comprise inhibiting the growth of primary tumor cells, inhibiting the formation of metastases, inhibiting the growth of metastases, killing circulating melanoma cells, inducing remission, extending remission, or inhibiting recurrence. The Axl kinase inhibitor may be administered more than once, and/or the taxane and/or gemcitabine may be administered more than once. The taxane may be selected from paclitaxel and nab-paclitaxel. The Axl kinase inhibitor may be selected from BGB324 and warfarin.

The method may have taxane and/or gemcitabine administered before said Axl kinase inhibitor, or may have taxane and/or gemcitabine administered at the same time as said Axl kinase inhibitor, or may have taxane and/or gemcitabine administered after said Axl kinase inhibitor. Administering may comprise intravenous, intraperitoneal intraarterial, subcutaneous, oral or intra-tumoral administration, or comprise local, regional or systemic administration, or comprise continuous infusion over a period of time.

The PDA may be stage T1-T2 disease, or stage T3-T4 disease. The subject may previously received a radiotherapy, a chemotherapy, an immunotherapy, a molecularly targeted therapy or had surgical resection of a tumor. The subject may have failed one or more standard melanoma therapies. The amount sufficient to inhibit said PDA may be less than the amount required for inhibition by any single agent alone. The amount sufficient to inhibit said PDA may be less toxic than the amount required for inhibition by any single agent alone.

Also provided are methods and compositions for screening therapeutics and biomarkers for pancreatic ductal adenocarcinoma. In a first embodiment, there is provided a non-human transgenic animal comprising a transgene encoding Rgs16 operably linked to green fluorescent protein (GFP) or a functional disruption in an endogenous Rgs16 and an endogenous Rgs8 gene; and an activating Kras mutation. In certain aspects, the functional disruption substantially reduces the expression of the Rgs16 and Rgs8 gene products. In some aspects, the animal is a rodent. In particular aspect, the rodent is a mouse.

In certain aspects, the one or more tumor suppressor gene or loci that is misexpressed. In some aspects, misexpression results in decreased expression of one or more tumor suppressor genes or loci. In particular aspects, the one or more tumor suppressor genes or loci are disrupted by removal of DNA encoding all or part of the tumor suppressor protein. For example, the tumor suppressor gene is selected from the group consisting of Ink4a/ARF, Ink4a, Arf, p53, Smad4/Dpc, Lkb1, Brca2, and Mlh1.

In other aspects, the Kras mutation is $Kras^{G12D}$ knock-in allele (LSL-Kras). In particular aspects, the LSL-$Kras^{G12D}$ is under the control of p48-Cre. In a particular aspect, the animal comprises a functional disruption in an endogenous Rgs16 gene and an endogenous Rgs8 gene, and the activating Kras mutation is LSL-$Kras^{G12D}$ under the control of p48-Cre.

A further embodiment provides a method of screening a candidate drug or drug combination for efficacy in treating pancreatic ductal adenocarcinoma (PDA) in a subject comprising administering an effective amount of the drug or drug combination to the transgenic animal comprising a transgene encoding Rgs16 operably linked to green fluorescent protein (GFP) or a functional disruption in an endogenous Rgs16 and an endogenous Rgs8 gene; and an activating Kras mutation; and measuring the Rgs16::GFP fluorescence intensity wherein a decrease in fluorescence intensity identifies a candidate drug or drug combination. In certain aspects, the efficacy in treating comprises inhibiting the growth of primary tumor cells, inhibiting the formation of metastases, inhibiting the growth of metastases, or killing circulating tumor cells. In some aspects, the subject is human.

In further aspects, the pancreas is dissected prior to measuring fluorescence intensity. In some aspects, the fluorescence intensity correlates with tumor size and number of tumor initiation sites.

In some aspects, the candidate drug or drug combination is administered orally, topically, or by injection. For example, the drug combination comprises gemcitabine and/or paclitaxel.

In certain aspects, the step of measuring the fluorescence intensity is performed about 1 to 3 weeks after administering an effective amount of the drug or drug combination. In other aspects, the step of measuring the fluorescence intensity is performed about 2 weeks after administering an effective amount of the drug or drug combination In yet another embodiment, there is provided a method of identifying a biomarker for pancreatic insufficiency, pancreatic intraepithelial neoplasms (PanINs) or PDA comprising comparing the expression of a gene or protein in a sample from the transgenic animal comprising a transgene encoding Rgs16 operably linked to green fluorescent protein (GFP) or a functional disruption in an endogenous Rgs16 and an endogenous Rgs8 gene; and an activating Kras mutation to a sample from a control mouse.

In further aspects, RNA-sequencing or mass spectrometry is performed on the sample. For example, the sample is blood, pancreatic juice, feces or other body fluids.

In certain aspects, the biomarker is a metabolic marker associated with malnutrition. In other aspects, the identified biomarker is a diagnostic biomarker. In further aspects, the identified biomarker is a prognostic biomarker.

In even further aspects, cells are isolated from the genetically engineered mouse model. In some aspects, the RNA-sequencing and/or mass spectrometry is performed on the isolated cells.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The disclosure may be better understood by reference to one or more of these drawings in combination with the detailed description of specific embodiments presented herein.

FIG. 1. Rgs16::GFP is a Kras$^{G12D}$-dependent reporter of pancreatic neoplasia. Rgs16::GFP is expressed in early pancreatic ductal neoplasia (IPMN, PanIN and PDA) but not in functional acinar cells of GFP-KIC and GFP-KC mice (age=P29). No fluorescence background is detected in PDA tumors in mice lacking the Rgs16::GFP transgene (KIC or KC w/o GFP) nor in GFP-IC or normal glycemic Rgs16::GFP (GFP-WT) pancreata. Live fluorescence microscopy. Scale bar=1 mm.

FIGS. 2A-B. Rgs16::GFP is a Kras$^{G12D}$-dependent reporter of PDA expansion. (FIG. 2A) Early lesions appear by postnatal day 15 (P15) marked by Rgs16::GFP expression in ducts. As tumors grow GFP expression increases. (FIG. 2A) (lower panels) pancreata of normal glycemic, age-matched Rgs16::GFP mice. Live fluorescence microscopy. Scale bar=1 mm. (FIG. 2B) Rgs16::GFP expression increases with age and PDA expansion. GFP fluorescence of PDA tumors at P29 (arrows) is about 10,000-fold greater than non-tumorigenic, euglycemic Rgs16::GFP mice. Quantification of GFP expression based on the averages of the highest intensity pictures of each pancreas of GFP-KIC (G-KIC) and control (G-Ctrl) mice between P15 to P29. Age and number of mice in Rgs16::GFP;KIC and Rgs16::GFP-Control groups is noted.

(FIG. 5A) Endogenous Rgs16 protein is expressed in ducts of primary tumors. Anti-Rgs16 antibody staining (brown) of a KIC mouse pancreas. (insert: section from the same tumor not stained with primary antibody. Background staining is Alcian Blue & Periodic Acid-Schiff.; Scale bar=50 µm). (FIG. 5B) Single cell suspension of PDA cells from tumor at 6 weeks transplanted orthotopically into NOD-SCID recipient forms large tumors within two weeks. Rgs16::GFP is expressed in duct-like structures in close association with blood vessels (white bar, 100 µm). (FIG. 5C) Primary tumor; Rgs16::GFP (green) and Muc-1 (red) are co-expressed (overlap appears yellow) in PanIN lesions of the ductal epithelium. (FIG. 5D) Cluster dendrogram of RNA-Seq gene expression profiles. The dendrogram was obtained by hierarchical clustering of pairwise distances between all samples using normalized gene expression values. Each branch represents a sample. E18.5 and adult pancreas (5 replicates each), PDA primary cell culture (cells sorted into Rgs16::GFP positive and GFP negative samples), E13.5 and E17.5 (1 sample each). (FIG. 5E) 3D scatterplot showing dissimilarity between samples. The inventors computed Euclidean distance between each pair of samples and scaled these distances using multidimensional scaling for representation in three-dimensional space. Each axis represents a dimension and axis values represent range of dissimilarities between samples. (FIG. 5F) Heatmap showing the expression of markers in each sample. They selected a set of markers for developmental stages and computed the z-score to portray their relative expression levels in each sample. Red represents higher expression and green represents lower expression compared to population mean.

(FIG. 6A) The two highest intensity images of GFP-KIC mice at P29 are shown for the (a and b) untreated (Untr), (c and d) warfarin (W), (e and f) gemcitabine and Abraxane (GA), and (g and h) warfarin with gemcitabine and Abraxane (WGA) groups. Scale bars are 1 mm. (FIG. 6B) gemcitabine+Abraxane (GA) with the Gas6/Axl inhibitors warfarin (blue dots; WGA, n=14), BGB324 (light blue dots; BGA, n=15) or both (WBGA, dark blue dots, n=24) inhibit growth of large PDAs and reduce PanINs throughout the pancreas (many fields with little or no GFP; n=53). GA alone (green dots, n=30) reduces PanINs but resistant tumors occur (many fields with high GFP). Warfarin alone (W, pale dots, n=16) has no effect, similar to untreated control (U, black dots, n=42). WGA, BGA, WBGA show pancreata from individual mice; each column of 5 dots represents one pancreas, each dot a single micrograph, non-overlapping fields from 1st to 5th brightest (quantitated by ImageJ; statistics in FIG. 7). All of the untreated (U), gemcitabine+Abraxane (GA), and warfarin (W) group images are collapsed into a single vertical alignment each to save space. The response to gemcitabine alone (n=30) and gemcitabine+warfarin (n=33) is shown in FIG. 18; statistics in FIG. 8. Control mice (Ctrl, Rgs16::GFP transgenics, grey lines, n=24) which are represented as one line per mouse. The 95-percentile and 1-percentile of all image values within untreated group are depicted with dashed horizontal lines and the percentage of mice with images above and below, respectively, of these values are indicated for each group. Small alphabetical letters correspond to images in FIG. 6A. Mean Log (GFP) of each group (FIG. 7). Pancreata of untreated PDA mice express significantly more Rgs16::GFP than treated groups (GA, BGA, WGA), WT (Rgs16::GFP; WT p48; light grey bar), P (PDA without GFP, P39, dark grey bar). Student's t-test, $p<0.01$, *$p<0.001$, ****$p<0.0001$.

FIG. 7. Axl inhibitors augment gemcitabine+Abraxane inhibition of PDA growth. Statistical analysis for difference between non-treatment and treatment mice, except for the final two statistics, were performed against the GA and BGA group, respectively. Values in red show a statistically significant difference between treated and non-treated groups. All tests are based on finding the respective statistic for each mouse and then taking the mean across the groups, except for median, which took the median of the medians across the groups. The Student's t-test was used for all tests except for the median, which was assessed using the Wilcoxon rank sum test. #The ratio statistics involving a median were calculated in the following manner: for each mouse, the lowest (or highest) log GFP was taken and divided by the indicated group's median log GFP, followed by taking the mean of those individual ratios across each group. NT, non-treatment group; GA, gemcitabine and Abraxane; BGA, BGB324 with gemcitabine and Abraxane; WGA, warfarin with gemcitabine and Abraxane. ##Mean and median log Rgs16::GFP are significantly lower in all treatment groups, including lowest log GFP of each treatment group compared to the median log GFP of the non-treatment group. These drugs suppress PanIN progression towards PDA. However, highest GFP in the GA group is not significantly different from NT, indicating drug-resistant PDA. Treatment with Gas6/Axl inhibitors (B and W) lowers the highest log Rgs16::GFP (WGA is statistically significant), indicating combined therapy retards drug-resistant PDA. NT, non-treatment group; GA, gemcitabine and Abraxane; BGA, BGB324 with gemcitabine and Abraxane; WGA, warfarin with gemcitabine and Abraxane.

FIG. 8. Gemcitabine (G) and warfarin (WG) inhibit PDA tumor growth. The figure presents the results for testing for differences between the non-treatment and the treatment mice, except for the final statistic, which was tested against the G group. Values shown in red show statistically significant difference between treated and non-treatment groups. All tests are based on finding the respective statistic for each mouse and then taking the mean across the groups, except for median, which took the median of the medians across the groups. The Student t-test was used for all tests except for the median*, which was assessed using the Wilcoxon rank sum test. #The ratio statistics involving a median were calculated in the following manner: for each mouse, the lowest (or highest) log GFP was taken and divided by the indicated group's median log GFP, followed by taking the mean of those individual ratios across each group. NT, non-treatment group; G, Gemcitabine; WG, Warfarin+Gemcitabine.

(FIGS. 9A-B) Pancreatic ductal neoplasia observed in bright-field (BF) and Rgs16::GFP expression observed by fluorescence microscopy always coincided (white arrows) regardless of whether mice were vehicle or drug treated. PDA was never observed in the hepatopancreatic common duct (HPCD; delineated by red dotted line). Intestine (Int). (FIGS. 9C-F) PDA in KIC mice initiates anywhere from head to tail of the pancreas. Neoplasia seen in bright-field whole-pancreas (white arrow) are compared to their corresponding Hematoxylin & Eosin (H&E) stained sections (black arrows). FIGS. 9C and 9E are composites of several low magnification pictures. Scale bar=1 mm.

(FIG. 15A) Pancreatic lobe with high Rgs16::GFP expression which, in live imaging, always marks lobes with edema. Remarkably high level of CPA1 in Rgs16::GFP-expressing acinar-like cells relative to normal acinar cells in neighboring unaffected lobes. (FIGS. 15B-C) Continued expression of Rgs16::GFP in pancreatic lobes with features of ADM and PanIN (FIG. 15B) and PanIN and PDA (FIG. 15C). Arrows in FIG. 15A and FIG. 15B highlight examples of acini with co-expression of Rgs16::GFP and CPA1.

(FIG. 17A) Abraxane; B, BGB324; G, gemcitabine; W, warfarin. (FIG. 17B) All of the mice from each cohort of untreated (Unt, n=42), gemcitabine and Abraxane treated (GA, n=12; n=9 for _v2B; n=9 for _v2G), and warfarin treated (W, n=16) are shown. Images of the 5 brightest fields from one representative untreated mouse (red box) are shown to the left. Each column of 5 dots shows GFP intensity in the pancreas of an individual mouse, where each dot corresponds to a single micrograph: non-overlapping fields from $1^{st}$ to the $5^{th}$ brightest (quantitated by ImageJ; FIG. 7). The horizontal dotted lines define the 95% ile and 1% ile of all Unt GFP intensity. 14% of the untreated mice had at least one field of Rgs16::GFP expression in pancreas greater than the upper 95% ile of all fields, whereas GA (combined) and W had 20% and 13% incidences, respectively. On the other hand, 53% of the GA treated mice had at least one field in the lower 1% ile of all fields (some fields are comparable to Ctrl), indicating a significant inhibition of neoplasia initiation compared to Unt (7%) or W (19%). Rgs16::GFP control mice (Ctrl, n=24), which do not express Kras$^{G12D}$, show background fluorescence levels (grey lines). Vehicle for Abraxane and gemcitabine was saline solution and PBS, respectively. Meanwhile, drugs BGB324 and GDC980 dissolved in 30% Cyclodextrin (_v2B and _v2G) did not exert an effect on GFP levels when combined with GA and added to the GA pool in FIGS. 6A-B. Scale bar=1 mm. (FIG. 17C) Averages of quantified values from maximum intensity micrographs of untreated and drug-treated KIC mice are shown. Statistical analyses were obtained by comparing log(GFP) values of drug-treated mice to Unt via unpaired and two-tailed Student's t-test. *, $p<0.05$; *, $p<0.001$; **, $p<0.0001$. Asterisks match the color of the comparison group.

(FIG. 20B) BGB324 (green round); (FIG. 20C) warfarin (blue round); or (FIG. 20D) BGB324 with warfarin (green or blue round) at the indicated concentrations. PDA primary cells were plated at equal density (black open circle) at the start. Next day, cells were treated with drugs (D, red font) for 24 hr (red line). Approximate cell number at the start of drug treatment was obtained from another plate with equal density (red open circle). At the end of treatment, cells in each group were counted and subsequent passages started with cells plated at equal density (grey asterisk). Drug treated groups were allowed to grow without drug selection thereafter. Control cells (Ctrl) on separate plates were grown without drug and counted at the end of each passage (black open circle). PDA live cell numbers were obtained via counts using a hemocytometer after 2% Trypan blue staining to distinguish between living and dead cells under an inverted microscope with 10× objective. Statistical significances are based on comparison of drug-treated cell counts to Ctrl. Cells did not recover from gemcitabine treatment but did from BGB324 treatment within four passages. Warfarin had little or no effect on cell growth. Statistical analyses were obtained by comparing counts of drug-treated cells to Ctrl via unpaired and two-tailed Student's t-test. *, $p<0.05$; , $p<0.01$; *, $p<0.001$; ****, $p<0.0001$. Asterisks match the color of the comparison group.

FIGS. 23A-G. Warfarin inhibits tumor progression in Axl expressing cell lines. (FIG. 23A) Primary tumor burden after therapy with warfarin. Therapy was initiated when implanted tumors were visible by ultrasound (~10 mm³) and consisted of control (normal drinking water) or warfarin, administered in the drinking water at 0.5 mg/L (immunocompetent mice: Pan02 (n=4, control; 3, warfarin), KIC (n=10, control; 8, warfarin)) or 1 mg/L (Panc-1 (n=10, control; 8, warfarin), AsPC-1 (n=8, control; 6, warfarin), Capan-1 (n=10, control; 7, warfarin)) and continued for 2-4 weeks until control mice were moribund. Therapy in KIC mice was initiated at 3 weeks of age and continued for 4 weeks. (FIG. 23B) Metastases were determined grossly upon sacrifice and confirmed by histological evaluation of the liver. Metastatic burden is normalized to mean number of metastases in control treated animals and is displayed as a fold change. Incidence of metastasis is also indicated. (FIG. 23C) Murine pancreatic cancer cells express Axl by flow cytometry. (FIGS. 23D-E) Expression of Axl message and protein by human pancreatic cancer cell lines. (FIG. 23F) shRNA-mediated knock-down of Axl suppresses growth of orthotopic Mia PaCa-2 tumors (n=8, shLuc; 7, shAxl). Tumor volume determined by serial ultrasound. (FIG. 23G) Inhibition of Axl with mAb 10C9 reduces tumor growth and suppresses metastasis of MiaPaCa-2 tumors (n=7, control; 8, 10C9). Therapy with mAb 10C9 (250 µg 2x/week) was initiated when tumors were established as above and persisted for 4 weeks. All results were compared by unpaired two-tailed t-test with Welch's correction, actual p values are shown. Error bars indicate s.e.m.

FIGS. 24A-F. Warfarin inhibits Axl signaling in vitro and in vivo. (FIG. 24A) HEK293 cells engineered to stably express recombinant Gas6 were grown in the presence of Vitamin K or Vitamin K+warfarin. Gas6 levels and γ-carboxylation were assayed by immunoblotting conditioned media. Conditioned media from untransfected HEK293 cells was used as a negative control. (FIG. 24B) Panc1 cells were grown overnight in media with 1% serum with no additions (NT), warfarin (2 µM) or BGB324 (2 µM). Lysates were probed for total Axl (tAxl) and phosphorylated Axl (pAxl). (FIG. 24C) Panc1 cells were grown in the presence of control media, Vitamin K, warfarin or warfarin+Vitamin K. The level of phosphorylated Axl (pAXL, red) was determined by immunofluorescence. (FIG. 24D) Panc1 cells were grown overnight in media with 1% serum with no additions (control), warfarin (1 µM), Gas6 (1.3 nM) or Gas6+warfarin. Lysates were probed for phosphorylated Akt (pAkt) and actin. (FIG. 24E) Lysates from Panc1 tumors harvested from mice treated with control or warfarin were probed for expression of tAxl, pAxl, actin, pAKT, tAKT, and cleaved Parp. (FIG. 24F) The effect of warfarin on cell migration was assessed by a 'scratch' assay. Monolayers of the indicted cells were wounded with a pipet tip. The cells were incubated in media containing 2% serum+/−warfarin (2 µM) or media containing 2% serum+Gas6 (1.3 nM)+/−warfarin. Wound closure was monitored at 16 hrs and is reported as % wound closure. *$p<0.05$, ***$p<0.001$ by ANOVA, Bonferroni's MCT.

FIGS. 25A-I. Axl inhibition reduces colony formation and enhances chemotherapy. (FIGS. 25A-C) parental Mia PaCa-2 cells or Mia PaCa-2 cells stably transfected with shRNA targeting Axl (Mia shAxl) were grown as spheroids in matrigel for 7 days in the presence or absence of warfarin (200 ng/ml), n=4/condition. Mia PaCa-2 cell colonies form large stellate colonies characteristic of invasive tumor growth. Colonies and cognate cell projections were imaged (FIG. 25A) with a Nikon Phase contrast microscope using 40× and 200× magnification. Mean total colony number (FIG. 25B) and total colony area+/−s.d. (FIG. 25C) reflective of invasive growth were calculated using Image J image analysis. Scale bar, 100 µm. **, $p<0.001$ vs Mia PaCa-2 NT; ##, $p<0.01$; ###, $p<0.005$. by ANOVA with Tukey's MCT. (FIG. 25D) soft agar colony formation for AsPC-1, Mia PaCa-2, and Capan-1 cells grown in normal growth media in the presence or absence (Control) of warfarin (2 µM) for 14 days. Mean+/−s.d. colonies/hpf is shown. Unpaired two tailed t-test with Welch's correction. (FIG. 25E) liver metastases were quantified after intrasplenic injection of C5LM2 cells. Animals (10/group) were treated with normal drinking water, warfarin (1 mg/L) beginning 48 hours prior to (pre-op) or 48 hours following tumor cell injection (post-op) and then continued on warfarin therapy until time of sacrifice. *, $p<0.005$; **, $p<0.001$ vs control; #, $p<0.05$ vs post-injection treatment group by ANOVA with Tukey's MCT. (FIGS. 25F-I) Mice bearing established orthotopic C5LM2 (FIGS. 25F-G) or Mia PaCa-2 (FIGS. 25H-I) were treated with saline (control), gemcitabine (Gem), Gem+warfarin (Gem+War). Mice bearing Mia PaCa-2 tumors were also treated with warfarin alone (War), Gem+10C9. Mice were sacrificed when control treated animals were moribund and primary and metastatic burden was determined. Primary tumor weight+/−s.d. (FIG. 25F, FIG. 25H) and fold change in metastases+/−s.d. (FIG. FIG. 25) is shown. The incidence of metastasis in each group is shown as a %. , $p<0.01$; *, $p<0.005$; **, $p<0.001$ vs Control; #4, $p<0.01$ vs Gem by ANOVA with Tukey's MCT.

FIGS. 26A-C. Warfarin inhibits Axl-dependent maintenance of EMT. (FIG. 26A) the expression level of pAxl, Zeb1 and nuclear β-catenin in Panc1 cells in vitro was measured by immunofluorescence under normal culture conditions or after growth on collagen matrix and treatment with TGF-β (20 ng/ml) to induce epithelial to mesenchymal transition, with or without warfarin (2 µM). p-Axl was normalized to total Axl area. (FIG. 26B) Panc1 cells were treated with either SFM, recombinant Gas 6 (100 ng/ml) or Gas6 following pretreatment with 10C9 (mAb anti-Axl). Transition to a mesenchymal phenotype was characterized by changes in vimentin and nuclear Zeb1 expression determined by immunofluoresence. (FIGS. 26A-B) Data are displayed as mean±SEM and represent 5 images per chamber, with assay performed in triplicate. % area per image was normalized to cell number. Images were analyzed using Elements software. *, $p<0.05$; **, $p<0.001$ by ANOVA with Tukey's MCT. (FIG. 26C) Paraffin embedded sections of Panc-1 tumors were analyzed by immunofluorescence for markers of EMT. Representative images of E-Cadherin and Vimentin are shown. Total magnification, 200×; scale bar, 100 µM. Images were analyzed using Elements software; quantification of % area fraction is shown. Data is displayed as mean±s.d. and represent 5 images per tumor with 5 animals per group analyzed. **$p<0.0001$ by t-test.

FIGS. 27A-D. Axl is required for the growth of Mia PaCa-2 tumors. SCID mice were injected orthotopically with Mia PaCa-2 cells stably expressing control (shLuc, n=8) or targeted (shAxl, n=7) shRNA constructs. (FIG. 27A) Tumor volume was monitored by sonography. (FIG. 27B) At the time of sacrifice (~d72) all mice injected with Mia-shLuc cells had large tumors while 4 of 7 mice injected with Mia-shAxl cells had large tumors. These tumors are indicated as shAxl-revert. (FIGS. 27C-D) The expression level of Axl was determined by qPCR (FIG. 27C) and western blotting (FIG. 27D) in Mia PaCa-2 parental cells, shLuc, shAxl-revert and shAxl tumors or cells.

FIGS. 28A-D. Characterization of 10C9. (FIG. 28A) ELISA of 10C9 and AF154 (R&D Systems) for binding to Axl coated wells. (FIG. 28B) Flow cytometric analysis with 10C9 or a control IgG (Cntl) for Axl expression in MIA PaCa-2 cells stably transfected with shRNA targeting luciferase (shLuc) or Axl (shAxl). (FIGS. 28C-D) Axl (FIG. 28C) and p-Axl (FIG. 28D) expression by Panc-1 cells in vitro was measured by immunofluorescence after overnight Gas6 exposure (100 ng/ml) in either SFM or following pre-incubation (30 min) with 10C9 (168 µg/ml). Data are displayed as mean±SEM and represent 5 images per chamber, with assay performed in triplicate. % area per image was normalized to cell number. Images were analyzed using Elements software. *p<0.05.

FIGS. 30A-D. In vivo warfarin effects. (FIG. 30A) Paraffin embedded sections of Panc-1 tumors were analyzed by H&E for viable tumor tissue. Sections were evaluated on lowest magnification (40× total mag) and area % necrosis was quantified. Data is displayed as mean±SEM and represent 5 images per tumor with 5 animals per group analyzed. (FIGS. 30B-D) Paraffin imbedded sections of Panc-1 tumors were evaluated by immunofluorescence for markers of proliferation (FIG. 30B, p-Histone H3), apoptosis (FIG. 30C, cleaved Caspase 3), and microvessel density (FIG. 30D, Endomucin). Data is displayed as mean±SEM and represent 5 images per tumor with 5 animals per group analyzed Representative images of FIG. 30C, cleaved caspase 3 (red) and FIG. 30D, Endomucin (green) are shown. Total magnification, 200×; scale bar, 100 μM. Images were analyzed using Elements software, quantification of % area expression/hpf is shown. *p<0.05, ***p<0.001 vs control by t-test.

FIGS. 31A-B. Maintenance of mesenchymal phenotype is Axl dependent and inhibited by warfarin. (FIGS. 31A-B) Mia PaCa-2 cells were grown in 1% serum containing media the absence (Control) or presence of warfarin (2 μM) overnight. Cells were assessed for expression of phosphorylated Axl, nuclear Zeb1 (FIG. 31A) and vimentin and E-cadherin (FIG. 31B) by ICC. Data are displayed as mean±SEM and represent 5 images per chamber, with assay performed in triplicate. % area per image was normalized to cell number. (FIG. 31B) Representative images of Vimentin and E-Cadherin expression are shown, total magnification 400×. Images were analyzed using Elements software. Welch's t-test*, p<0.05; **, p<0.01 vs control.

FIGS. 32A-C. Acquisition of Axl expression sensitizes Capan-EMT cells to warfarin. (FIG. 32A) Capan-1 cells cultured on collagen were analyzed by flow cytometry for Axl expression. The positive gate was set using a control IgG and 10C9 was used to detect Axl. Capan-1 cells cultured on collagen in the presence of TGFβ (20 ng/ml) (Capan-EMT) showed a ~4-fold induction of Axl expression. (FIG. 32B) Capan-EMT cells were cultured in SFM overnight in the absence (control) or presence of warfarin and expression Axl, E-Cadherin, and cleaved caspase 3 was determined by ICC. Representative images are shown. (FIG. 32C) The expression Zeb1, Snail, and Twist was determined by qPCR in Capan-1 and Capan-EMT cells.

FIGS. 33A-C. Metastasis in KC-R mice. The pancreas of KC mice undergo a well described progression from normal pancreas (NP), to dedifferentiated pancreas (DDP), acinar to ductal metaplasia (ADM), pancreatic intraepithelial neoplasia (PanIN) and eventually pancreatic ductal adenocarcinoma (PDA). KC-R, but not KC mice, then display uniform and rapid metastases to lung (FIG. 33A, gross morphology) and/or liver (FIG. 33B, gross morphology; FIGS. 33C, H&E immunohistology).

DETAILED DESCRIPTION

Figure 3:
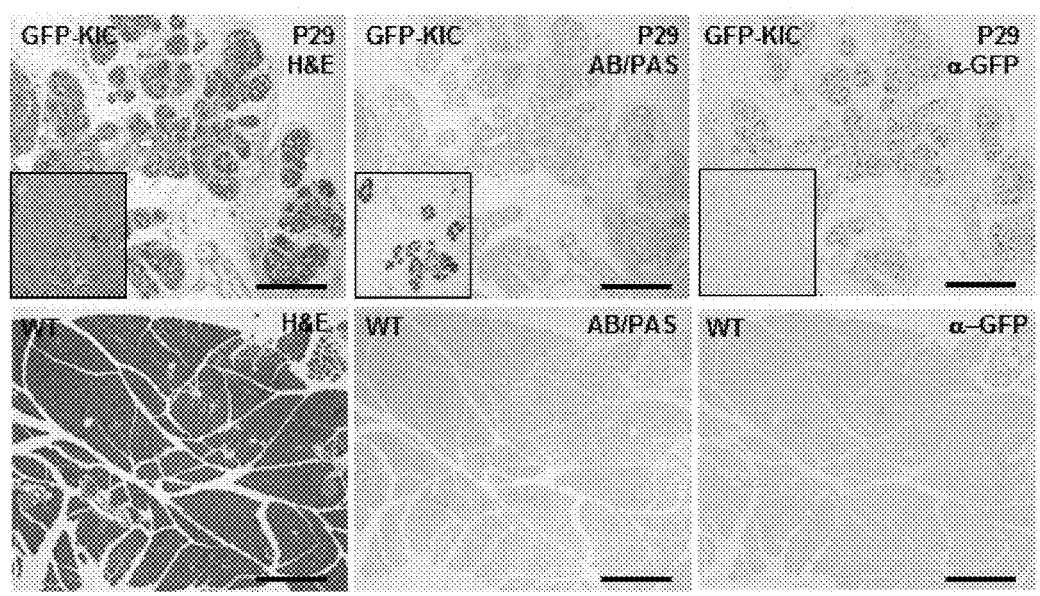
FIG. 3. Rgs16::GFP expression in pancreatic neoplasia. Hematoxylin & Eosin (H&E) staining for nuclear/cytoplasmic boundaries, Alcian Blue & Periodic Acid-Schiff (AB/PAS) staining for mucinous regions, and GFP staining for Rgs16 expression are shown in serial sections of GFP-KIC pancreas. Inserts compare a representative region that is AB/PAS positive but GFP negative at low resolution. Scale bar=500 µm.

To test if Rgs16 is an early marker of PDA, the inventors crossed the Rgs16::GFP transgene into KIC mice. Here, they show that the Rgs16::GFP transgene is a $Kras^{G12D}$ dependent marker of all stages of neoplasia in KIC mice—IPMN, PanIN, and PDA (Hruban et al., 2000; Maitra et al., 2005). The distribution and intensity of Rgs::GFP expression is proportional to and coincident with tumor burden. Thus, the inventors report here the development of a rapid, systematic, and robust in vivo screen for effective drug combinations to treat Kras-dependent PDA. Protein kinase and G-Protein Coupled Receptor signaling activates Kras. Regulators of G-protein Signaling (RGS) proteins are coincidence detectors that can be induced by multiple inputs to feedback regulate GPCR signaling. An Rgs16::GFP transgene is a $Kras^{G12D}$-dependent marker of all stages of PDA neoplasia, and increases proportional to tumor burden in KIC mice. RNA-Seq analysis of cultured primary PDA cells shows characteristics of embryonic progenitors of pancreatic ducts and endocrine cells, and extraordinarily high expression of the receptor tyrosine kinase Axl, an emerging cancer drug target.

The inventors show PDA weanling mice treated with the standard-of-care combination gemcitabine and nab-paclitaxel (Abraxane) (Masellis et al., 2009; Frese et al., 2012; Von Hoff et al., 2013; Neesse et al., 2014) for two weeks h ave significantly lower Rgs16::GFP expression and reduced tumor size and occurrence. The Axl tyrosine kinase receptor is associated with aggressive cancer and poor patient outcome in breast, liver, and pancreatic cancer (Gjerdrum et al., 2010; Song et al., 2011; Reichl et al., 2014). Axl, and its gamma-carboxylated ligand, Gas6, are associated with drug-resistant tumor relapse (Linger et al., 2008; Song et al., 2011; Schmidt et al., 2012, Kirane et al., 2015). The inventors therefore evaluated novel combinations of standard-of-care PDA chemotherapeutics with Gas6/Axl signaling inhibitors in a rapid in vivo PDA therapeutic assay. They show that warfarin or an Axl kinase inhibitor (BGB324), in combination with gemcitabine and nab-paclitaxel, significantly reduced tumor initiation and growth. Thus, the in vivo PDA model harboring the Rgs16::GFP reporter is an efficient system for identifying effective drug combinations, and for identifying novel or repurposed drugs to treat PDA.

Additionally, the Rgs16:GFP KIC mice are used to identify biomarkers of PanINs and PDA including early metabolic markers of pancreatic insufficiency. These markers appear during disease progression such as overeating, engorged intestines, large quantity of feces, hypoglycemia, weight loss, feces enriched in lipids and or/carbohydrates and include molecular markers in blood, pancreatic juice or feces. These markers can be used to identify subjects at high risk for developing PDA, and subjects identified with PanIN3 or PDA are candidates for tumor resection and/or neoadjuvant treatment. Thus, the in vivo PDA model with the Rgs16::GFP reporter can be used to identify biomarkers of pancreatic insufficiency, PanINs and PDA.

I. PDA Therapeutic Agents

The present inventors have determined that by combining the standard of care treatment for PDA—Abraxane® and gemcitabine—with an Axl kinase inhibitor, a more effective treatment is created.

A. Axl Kinase Inhibitors

Tyrosine-protein kinase receptor UFO is an enzyme that in humans is encoded by the AXL gene. The gene was initially designated as UFO, in allusion to the unidentified function of this protein. The protein encoded by this gene is a member of the receptor tyrosine kinase subfamily. Although it is similar to other receptor tyrosine kinases, the Axl protein represents a unique structure of the extracellular region that juxtaposes IgL and FNIII repeats. It transduces signals from the extracellular matrix into the cytoplasm by binding growth factors like vitamin K-dependent protein growth-arrest-specific gene 6 (GAS6). It is involved in the stimulation of cell proliferation. This receptor can also mediate cell aggregation by homophilic binding. The Axl gene is evolutionarily conserved between vertebrate species. This gene has two different alternatively spliced transcript variants. Axl is a chronic myelogenous leukemia-associated oncogene and also associated with colon cancer and melanoma. It is in close vicinity to the BCL3 oncogene, which is at 19q13.1-q13.2. There is ongoing research to develop possible drugs to target this signalling pathway and treat cancers.

Warfarin, also known by the brand names Coumadin among others, is an anticoagulant normally used in the prevention of thrombosis and thromboembolism, the formation of blood clots in the blood vessels and their migration elsewhere in the body, respectively. It was initially introduced in 1948 as a pesticide against rats and mice, and is still used for this purpose, although more potent poisons such as brodifacoum have since been developed. In the early 1950s, warfarin was found to be effective and relatively safe for preventing thrombosis and thromboembolism in many disorders. It was approved for use as a medication in 1954, and has remained popular ever since. Warfarin is the most widely prescribed oral anticoagulant drug in North America.

Despite its effectiveness, treatment with warfarin has several shortcomings. Many commonly used medications interact with warfarin, as do some foods (particularly leaf vegetable foods or "greens," since these typically contain large amounts of vitamin $K_1$) and its activity has to be monitored by blood testing for the international normalized ratio (INR) to ensure an adequate yet safe dose is taken. A high INR predisposes patients to an increased risk of bleeding, while an INR below the therapeutic target indicates the dose of warfarin is insufficient to protect against thromboembolic events.

Warfarin and related 4-hydroxycoumarin-containing molecules decrease blood coagulation by inhibiting vitamin K epoxide reductase, an enzyme that recycles oxidized vitamin $K_1$ to its reduced form after it has participated in the carboxylation of several blood coagulation proteins, mainly prothrombin and factor VII. Despite being labeled a vitamin K antagonist, warfarin does not antagonize the action of vitamin $K_1$, but rather antagonizes vitamin $K_1$ recycling, depleting active vitamin $K_1$. Thus, the pharmacologic action may always be reversed by fresh vitamin $K_1$. When administered, these drugs do not anticoagulate blood immediately. Instead, onset of their effect requires about two to three days before remaining active clotting factors have had time to naturally disappear in metabolism, and the duration of action of a single dose of warfarin is 2 to 5 days. Reversal of warfarin's effect by discontinuing its use, or by administering vitamin $K_1$, requires a similar period of time.

Warfarin is a synthetic derivative of dicoumarol, a 4-hydroxycoumarin-derived mycotoxin anticoagulant originally discovered in spoiled sweet clover-based animal feeds. Dicoumarol, in turn, is derived from coumarin, a sweet-smelling but coagulation-inactive chemical found naturally in "sweet" clover (to which it gives its odor and name), tonka beans (also known as "cumaru" from which coumarin's name derives), and many other plants.

Warfarin consists of a racemic mixture of two active enantiomers—R- and S-forms—each of which is cleared by different pathways. S-warfarin is 2-5 times more potent than the R-isomer in producing an anticoagulant response.

Warfarin is slower-acting than the common anticoagulant heparin, though it has a number of advantages. Heparin must be given by injection, whereas warfarin is available orally. Warfarin has a long half-life and need only be given once a day. Heparin can also cause a prothrombotic condition, heparin-induced thrombocytopenia (an antibody-mediated decrease in platelet levels), which increases the risk for thrombosis. It takes several days for warfarin to reach the therapeutic effect since the circulating coagulation factors are not affected by the drug (thrombin has a half-life time of days). Warfarin's long half-life means that it remains effective for several days after it was stopped. Furthermore, if given initially without additional anticoagulant cover, it can increase thrombosis risk (see below). For these main reasons, hospitalised patients are usually given heparin with warfarin initially, the heparin covering the 3-5 day lag period and being withdrawn after a few days.

Dosing of warfarin is complicated because it is known to interact with many commonly used medications and certain foods. These interactions may enhance or reduce warfarin's anticoagulation effect. To optimize the therapeutic effect without risking dangerous side effects such as bleeding, close monitoring of the degree of anticoagulation is required by a blood test measuring an INR. During the initial stage of treatment, INR is checked daily; intervals between tests can be lengthened if the patient manages stable therapeutic INR levels on an unchanged warfarin dose. Newer point-of-care testing is available and has increased the ease of INR testing in the outpatient setting. Instead of a blood draw, the point of care test involves a simple finger prick.

When initiating warfarin therapy ("warfarinization"), the doctor will decide how strong the anticoagulant therapy needs to be. The target INR level varies from case to case depending on the clinical indicators, but tends to be 2-3 in most conditions. In particular, target INR may be 2.5-3.5 (or even 3.0-4.5) in patients with one or more mechanical heart valves.

In addition, for the first three days of "warfarinization", the levels of protein C and protein S (anticoagulation factors) drop faster than procoagulation proteins such as factor II, VII, IX, and X. Therefore, bridging anticoagulant therapies (usually heparin) are often used to reverse this temporary hypercoagulable state.

Warfarin interacts with many commonly used drugs, and the metabolism of warfarin varies greatly between patients. Some foods have also been reported to interact with warfarin. Apart from the metabolic interactions, highly protein bound drugs can displace warfarin from serum albumin and cause an increase in the INR. This makes finding the correct dosage difficult, and accentuates the need of monitoring; when initiating a medication that is known to interact with warfarin (e.g., simvastatin), INR checks are increased or dosages adjusted until a new ideal dosage is found.

Many commonly used antibiotics, such as metronidazole or the macrolides, will greatly increase the effect of warfarin by reducing the metabolism of warfarin in the body. Other broad-spectrum antibiotics can reduce the amount of the normal bacterial flora in the bowel, which make significant quantities of vitamin $K_1$, thus potentiating the effect of warfarin. In addition, food that contains large quantities of vitamin $K_1$ will reduce the warfarin effect. Thyroid activity also appears to influence warfarin dosing requirements; hypothyroidism (decreased thyroid function) makes people less responsive to warfarin treatment, while hyperthyroidism (overactive thyroid) boosts the anticoagulant effect. Several mechanisms have been proposed for this effect, including changes in the rate of breakdown of clotting factors and changes in the metabolism of warfarin. Warfarin also believed to interact with various foodstuffs, including ginger, garlic, ginseng and cranberry juices, as well as alcohol.

The following, additional drugs targeting, Axl kinase are in clinical or preclinical investigation: BGB324 (BergenBio & Rigel Pharmaceuticals), S49076 (Servier, Neuilly-sur-Seine, France), TP 0903 (Tolero Pharmaceuticals, Salt Lake City, Utah, & Astex Pharmaceuticals, Dublin, Calif.), LY2801653 (Eli Lilly & Co.), MP-470 (Astex Pharmaceuticals), SKI-606 (Pfizer(, MGCD 265 (Mirati Inc.), MGCD 516 (Mirati Inc.), ASP2215 (Astellas Pharmaceuticals), XL 184 (Exelixis), BMS-777607 (Aslan Pharmaceuticals, Inventive Healthcare Clinical), GSK136089/XL880 (GlaxoSmithKline), SGI-7079 (Astex Pharmaceuticals), SP3975 (Deciphera Biotech), NPS-1034 (NeoPharma), LDC1267 and NA80xl.

B. Gemcitabine

Gemcitabine is a nucleoside analog used as chemotherapy. It is marketed as Gemzar by Eli Lilly and Company. Chemically, gemcitabine is a nucleoside analog in which the hydrogen atoms on the 2' carbon of deoxycytidine are replaced by fluorine atoms. As with fluorouracil and other analogues of pyrimidines, the triphosphate analogue of gemcitabine replaces one of the building blocks of nucleic acids, in this case cytidine, during DNA replication. The process arrests tumor growth, as only one additional nucleoside can be attached to the "faulty" nucleoside, resulting in apoptosis.

Another target of gemcitabine is the enzyme ribonucleotide reductase (RNR). The diphosphate analogue binds to RNR active site and inactivates the enzyme irreversibly. Once RNR is inhibited, the cell cannot produce the deoxyribonucleotides required for DNA replication and repair, and cell apoptosis is induced.

Gemcitabine is administered by the intravenous route, since it is extensively metabolized by the gastrointestinal tract. Dose ranges from 1-1.2 g/m$^2$ of body surface area according to type of cancer treated.

Gemcitabine is used in various carcinomas: non-small cell lung cancer, pancreatic cancer, bladder cancer and breast cancer. It is being investigated for use in esophageal cancer, and is used experimentally in lymphomas and various other tumor types. Gemcitabine represents an advance in pancreatic cancer care. It is also not as debilitating as some other forms of chemotherapy.

A study reported in the Journal of the American Medical Association in 2007 suggested that gemcitabine showed benefit in patients with pancreatic cancer who were felt to have successful tumor resections.

Gemcitabine became first line treatment for bladder cancer Stage 4 with metastases in combination with cisplatin after a study in 2000 with 405 patients showed similar efficacy but less toxicity compared to the former MVAC regimen. This new CG-regimen involves taking cisplatin on day 2 and taking gemcitabine on days 1, 8, and 15. In July 2006 the FDA approved gemcitabine for use with carboplatin in the treatment of advanced ovarian cancer that has relapsed at least 6 months after completion of platinum-based (e.g., carboplatin or cisplatin) therapy. Neutropenia was the most commonly reported adverse effect (90% of patients). Other serious adverse effects were mostly hematologic. Gemcitabine was recently also investigated for advanced cancer of the biliary tract and gallbladder and was found to have a modest effect on the tumor when combined with cisplatin (NEJM 2010).

Side effects include flu-like symptoms such as muscle pain, fever, headache, chills, and fatigue, fever (within 6-12 hours of first dose), fatigue, nausea (mild), vomiting, poor appetite, skin rash, allergic reaction, diarrhea, weakness, hair loss, mouth sores, difficulty sleeping and shortness of breath.

C. Paclitaxel

Paclitaxel is a medication used to treat a number of types of cancer including: ovarian cancer, breast cancer, lung cancer and pancreatic cancer among others. It and docetaxel represent the taxane family of drugs. Paclitaxel's mechanism of action involves interference with the normal breakdown of microtubules during cell division. Common side effects include: hair loss, muscle and joint pains, and diarrhea, among others. It results in a greater risk of infections which can be potentially serious. Use during pregnancy often results in problems in the infant.

Paclitaxel was first isolated from the bark of the Pacific yew, *Taxus brevifolia*, thus its name "taxol." Developed commercially by Bristol-Myers Squibb, the generic name has changed to "paclitaxel" with a trademark becoming Taxol®. Other trademarks include Abraxane®. Clinicians sometimes use the abbreviation "PTX" for paclitaxel, which is discouraged, because it is not a unique identifier.

Paclitaxel is on the World Health Organization's List of Essential Medicines, a list of the most important medication needed in a basic health system. There was initially concern over the environmental impact of its initial sourcing from the slow growing Pacific yew. In addition, both the assignment of rights to Bristol-Myers Squibb and the product name were subject to public debate and Congressional hearings.

Albumin-bound paclitaxel (trade name Abraxane®, also called nab-paclitaxel) is an alternative formulation where paclitaxel is bound to albumin nano-particles. Much of the clinical toxicity of paclitaxel is associated with the solvent Cremophor EL® in which it is dissolved for delivery. Abraxis BioScience developed Abraxane®, in which paclitaxel is bonded to albumin as an alternative delivery agent to the often toxic solvent delivery method. This was approved by the U.S. Food and Drug Administration in January 2005 for the treatment of breast cancer after failure of combination chemotherapy for metastatic disease or relapse within six months of adjuvant chemotherapy.

Synthetic approaches to paclitaxel production led to the development of docetaxel. Docetaxel has a similar set of clinical uses to paclitaxel and is marketed under the name of Taxotere®. Recently the presence of taxanes including paclitaxel, 10-deacetylbaccatin III, baccatin III, paclitaxel C, and 7-epipaclitaxel in the shells and leaves of hazel plants has been reported. The finding of these compounds in shells, which are considered discarded material and are mass-produced by many food industries, is of interest for the future availability of paclitaxel.

Common side effects include nausea and vomiting, loss of appetite, change in taste, thinned or brittle hair, pain in the joints of the arms or legs lasting two to three days, changes in the color of the nails, and tingling in the hands or toes. More serious side effects such as unusual bruising or bleeding, pain/redness/swelling at the injection site, Hand-foot syndrome, change in normal bowel habits for more than two days, fever, chills, cough, sore throat, difficulty swallowing, dizziness, shortness of breath, severe exhaustion, skin rash, facial flushing, female infertility by ovarian damage and chest pain can also occur. A number of these side effects are associated with the excipient used, Cremophor EL, a polyoxyethylated castor oil. Allergies to drugs such as cyclosporine, teniposide and drugs containing polyoxyethylated castor oil may indicate increased risk of adverse reactions to paclitaxel. Dexamethasone is given prior to beginning paclitaxel treatment to mitigate some of the side effects. Leuprolide, a GnRH analog may prevent ovarian damage, according to mice studies.

Paclitaxel is one of several cytoskeletal drugs that target tubulin. Paclitaxel-treated cells have defects in mitotic spindle assembly, chromosome segregation, and cell division. Unlike other tubulin-targeting drugs such as colchicine that inhibit microtubule assembly, paclitaxel stabilizes the microtubule polymer and protects it from disassembly. Chromosomes are thus unable to achieve a metaphase spindle configuration. This blocks progression of mitosis, and prolonged activation of the mitotic checkpoint triggers apoptosis or reversion to the G-phase of the cell cycle without cell division.

The ability of paclitaxel to inhibit spindle function is generally attributed to its suppression of microtubule dynamics, but recent studies have demonstrated that suppression of dynamics occurs at concentrations lower than those needed to block mitosis. At the higher therapeutic concentrations, paclitaxel appears to suppress microtubule detachment from centrosomes, a process normally activated during mitosis. Paclitaxel binds to beta-tubulin subunits of microtubules.

II. Methods of Treatment

In a particular aspect, the present disclosure provides methods for the treatment of PDA. Treatment methods will involve administering to an individual having such a disease an effective amount of a composition or compositions containing a compound or compounds of the present disclosure. An effective amount is described, generally, as that amount sufficient to detectably and repeatedly to ameliorate, reduce, minimize or limit the extent of the disease or its symptoms. More specifically, it is envisioned that the treatment with a compound or compounds of the present disclosure kill cancer cells, inhibit their growth, reduce or inhibit metastasis, inhibit or reduce or delay recurrence, or otherwise provide clinical benefit. Also, the combination may reduce toxicity due to lower dosing and or reduced frequency of administration.

A. Pancreatic Ductal Adenocarcinoma (PDA)

Pancreatic cancer accounts for 22% of all deaths due to gastrointestinal malignancy, and 5% of all cancer deaths. In general it is a malignancy of the elderly with over 80% of cases occurring after the age of 60. Pancreatic ductal carcinoma makes up the vast majority (90%) of all pancreatic neoplasms, and remains a disease with very poor prognosis and high morbidity.

Three precursor lesions for pancreatic adenocarcinoma have been identified:
  pancreatic intraepithelial neoplasia (PanIN)
  intraductal papillary mucinous neoplasm (IPMN)
  mucinous cystic neoplasm Cancerous cells arise from pancreatic ductal epithelium. As the majority of tumors (90%) are not resectable, this is mostly achieved with imaging (typically CT scan) although laparoscopy is often required to confirm resectability. The key to accurate staging is assessment of the SMA and coeliac axis, which if involved exclude the patient from any attempted resection.

Histological types include adenocarcinoma (most), acinar cell carcinoma of pancreas, adenosquamous carcinoma of pancreas, an dundifferentiated with osteoclasts giant cells. Two-thirds of all cases are found in the head and uncinate process, with the remaining one third being found in the body and tail.

1. Early Signs

Since pancreatic cancer usually does not cause recognizable symptoms in its early stages, the disease is typically not diagnosed until it has spread beyond the pancreas itself. This is one of the main reasons for the generally poor survival rates. Exceptions to this are the functioning PanNETs, where over-production of various active hormones can give rise to symptoms (which depend on the type of hormone).

Bearing in mind that the disease is rarely diagnosed before the age of 40, common symptoms of pancreatic adenocarcinoma occurring before diagnosis include pain in the upper abdomen or back, often spreading from around the stomach to the back, jaundice, a yellow tint to the whites of the eyes or skin, with or without pain, and possibly in combination with darkened urine, and unexplained weight loss, either from loss of appetite, or loss of exocrine function resulting in poor digestion. The tumor may compress neighboring organs, disrupting digestive processes and making it difficult for the stomach to empty, which may cause nausea and a feeling of fullness. The undigested fat leads to foul-smelling, fatty feces that are difficult to flush away. Constipation is common.

At least 50% of people with pancreatic adenocarcinoma have diabetes at the time of diagnosis. While long-standing diabetes is a known risk factor for pancreatic cancer, the cancer can itself cause diabetes, in which case recent onset of diabetes could be considered an early sign of the disease. People over 50 who develop diabetes have eight times the usual risk of developing pancreatic adenocarcinoma within three years, after which the relative risk declines.

2. Risk Factors

Risk factors for pancreatic adenocarcinoma include age, gender, and race; the risk of developing pancreatic cancer increases with age. Most cases occur after age 65, while cases before age 40 are uncommon. The disease is slightly more common in men than women, and in the United States is over 1.5 times more common in African Americans, though incidence in Africa is low.

Cigarette smoking is the best-established avoidable risk factor for pancreatic cancer, approximately doubling risk among long-term smokers, the risk increasing with the number of cigarettes smoked and the years of smoking The risk declines slowly after smoking cessation, taking some 20 years to return to almost that of non-smokers. Obesity, defined as a BMI of greater than 35, increases relative risk by about half.

For about 5-10% of pancreatic cancer cases, there is an inherited component, where people have a family history of pancreatic cancer. The risk escalates greatly if more than one first-degree relative had the disease, and more modestly if they developed it before the age of 50. Most of the genes involved have not been identified. Hereditary pancreatitis gives a greatly increased lifetime risk of pancreatic cancer of 30-40% to the age of 70. Screening for early pancreatic cancer may be offered to individuals with hereditary pancreatitis on a research basis. Some people may choose to have their pancreas surgically removed to prevent cancer developing in the future.

Pancreatic cancer has been associated with the following other rare hereditary syndromes: Peutz-Jeghers syndrome due to mutations in the STK11 tumor suppressor gene (very rare, but a very strong risk factor); dysplastic nevus syndrome (or familial atypical multiple mole and melanoma syndrome, FAMMM-PC) due to mutations in the CDKN2A tumor suppressor gene; autosomal recessive ataxia-telangiectasia and autosomal dominantly inherited mutations in the BRCA2 gene and PALB2 gene; hereditary non-polyposis colon cancer (Lynch syndrome); and familial adenomatous polyposis. PanNETs have been associated with multiple endocrine neoplasia type 1 (MEN1) and von Hippel Lindau syndromes.

Chronic pancreatitis appears to almost triple risk, and as with diabetes, new-onset pancreatitis may be a symptom of a tumor. The risk of pancreatic cancer in individuals with familial pancreatitis is particularly high. Diabetes mellitus also is a risk factor for pancreatic cancer and (as noted in the Signs and symptoms section) new-onset diabetes may also be an early sign of the disease. People who have been diagnosed with Type 2 diabetes for longer than ten years may have a 50% increased risk, as compared with non-diabetics.

3. Diagnosis

The symptoms of pancreatic adenocarcinoma do not usually appear in the disease's early stages, and are individually not distinctive to the disease. The symptoms at diagnosis vary according to the location of the cancer in the pancreas, which anatomists divide (from left to right on most diagrams) into the thick head, the neck, and the tapering body, ending in the tail.

Regardless of a tumor's location, the most common symptom is unexplained weight loss, which may be considerable. A large minority (between 35% and 47%) of people diagnosed with the disease will have had nausea, vomiting or a feeling of weakness.

Tumors in the head of the pancreas typically also cause jaundice, pain, loss of appetite, dark urine, and light-colored stools. Tumors in the body and tail typically also cause pain.

People sometimes have recent onset of atypical type 2 diabetes that is difficult to control, a history of recent but unexplained blood vessel inflammation caused by blood clots (thrombophlebitis) known as Trousseau sign, or a previous attack of pancreatitis. A doctor may suspect pancreatic cancer when the onset of diabetes in someone over 50-years-old is accompanied by typical symptoms such as unexplained weight loss, persistent abdominal or back pain, indigestion, vomiting, or fatty feces. Jaundice accompanied by a painlessly swollen gallbladder (known as Courvoisier's sign) may also raise suspicion, and can help differentiate pancreatic cancer from gallstones.

Medical imaging techniques, such as computed tomography (CT scan) and endoscopic ultrasound (EUS) are used both to confirm the diagnosis and to help decide whether the tumor can be surgically removed (its "resectability"). Magnetic resonance imaging and positron emission tomography may also be used, and magnetic resonance cholangiopancreatography may be useful in some cases. Abdominal ultrasound is less sensitive and will miss small tumors, but can identify cancers that have spread to the liver and build-up of fluid in the peritoneal cavity (ascites). It may be used for a quick and cheap first examination before other techniques.

A biopsy by fine needle aspiration, often guided by endoscopic ultrasound, may be used where there is uncertainty over the diagnosis, but a histologic diagnosis is not usually required for removal of the tumor by surgery to go ahead.

Liver function tests can show a combination of results indicative of bile duct obstruction (raised conjugated bilirubin, γ-glutamyl transpeptidase and alkaline phosphatase levels). CA19-9 (carbohydrate antigen 19.9) is a tumor marker that is frequently elevated in pancreatic cancer. However, it lacks sensitivity and specificity, not least because 5% of people lack the Lewis (a) antigen and cannot produce CA19-9. It has a sensitivity of 80% and specificity of 73% in for detecting pancreatic adenocarcinoma, and is used for following known cases rather than diagnosis.

The most common form of pancreatic cancer (adenocarcinoma) is typically characterized by moderately to poorly differentiated glandular structures on microscopic examination. There is typically considerable desmoplasia or formation of a dense fibrous stroma or structural tissue consisting of a range of cell types (including myofibroblasts, macrophages, lymphocytes and mast cells) and deposited material (such as type I collagen and hyaluronic acid). This creates a tumor microenvironment that is short of blood vessels (hypovascular) and so of oxygen (tumor hypoxia). It is thought that this prevents many chemotherapy drugs from reaching the tumor, as one factor making the cancer especially hard to treat.

4. Staging

Both endocrine and exocrine tumors of the pancreas are now staged by a single pancreatic staging system. Staging of pancreatic ductal adenocarcinoma is with the TNM system, and as a majority of tumors are not-resectable, this is mostly achieved with imaging (typically CT scan) although laparoscopy is often required to confirm resectability. Primary tumor staging (T) is as follows:

Tx, T0, Tis: see TNM system
T1: tumor <2 cm in greatest dimension, limited to pancreas
T2: tumor >2 cm in greatest dimension, limited to pancreas
T3: extension beyond pancreas, no involvement of SMA or coeliac axis
T4: involvement of SMA or coeliac axis Regional Lymph Nodes (N) is as Follows:
Nx: nodes cannot be assessed
N0: no evidence of nodal involvement
N1: regional nodal metastases present Metastases (M) are Graded as Follows:
Mx: presence of metastases cannot be assessed
M0: no evidence of metastases
M1: distant metastases present Stage Groupings are as Follows:
stage 0: Tis N0 M0
stage Ia: T1 N0 M0
stage Ib: T2 N0 M0
stage IIa: T3 N0 M0
stage IIb: T1, T2 or T3 with N1 M0
stage III: T4 and M0 (any N)
stage IV: M1 (any T any N)

5. Treatment and Prognosis

As noted above, most tumors are not resectable at diagnosis. Surgery for stage I and II (see staging of pancreatic cancer) does offer the chance of cure, with however high morbidity (20-30%) and mortality (5%). Resection is performed with a Whipple operation. Even when resection is possible, the majority of patients succumb to recurrence, with only a doubling of survival in operated patients from 5 to 10% at 5 years. Almost a quarter of patients are dead 12 months following diagnosis.

B. Dosages

In certain embodiments, the compounds of the present disclosure is/are administered to a subject. In another embodiment of the disclosure, the dose range of the compound(s) will be measured by body weight, for example, about 0.5 mg/kg body weight to about 500 mg/kg body weight. Those of skill will recognize the utility of a variety of dosage range, for example, 1 mg/kg body weight to 450 mg/kg body weight, 2 mg/kg body weight to 400 mg/kg body weighty, 3 mg/kg body weight to 350 mg/kg body weighty, 4 mg/kg body weight to 300 mg/kg body weight, 5 mg/kg body weight to 250 mg/kg body weighty, 6 mg/kg body weight to 200 mg/kg body weight, 7 mg/kg body weight to 150 mg/kg body weighty, 8 mg/kg body weight to 100 mg/kg body weight, or 9 mg/kg body weight to 50 mg/kg body weight. Further, those of skill will recognize that a variety of different dosage levels will be of use, for example, 1 mg/kg, 2 mg/kg, 3 mg/kg, 4 mg/kg, 5 mg/kg, 7.5 mg/kg, 10 mg/kg, 12.5 mg/kg, 15 mg/kg, 17.5 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 120 mg/kg, 140 mg/kg, 150 mg/kg, 160 mg/kg, 180 mg/kg, 200 mg/kg, 225 mg/kg, 250 mg/kg, 275 mg/kg, 300 mg/kg, 325 mg/kg, 350 mg/kg, 375 mg/kg, 400 mg/kg, 450 mg/kg, 500 mg/kg, 550 mg/kg, 600 mg/kg, 700 mg/kg, 750 mg/kg, 800 mg/kg, 900 mg/kg, 1000 mg/kg, 1250 mg/kg, 1500 mg/kg, 1750 mg/kg, 2000 mg/kg, 2500 mg/kg, and/or 3000 mg/kg. Of course, all of these dosages are exemplary, and any dosage in-between these points is also expected to be of use in the disclosure. Any of the above dosage ranges or dosage levels may be employed for a compound or compounds of the present disclosure.

The treatments may include various "unit doses." Unit dose is defined as containing a predetermined-quantity of the therapeutic composition calculated to produce the desired responses in association with its administration, i.e., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion over a set period of time.

As is well known in the art, a specific dose level of active compounds for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, general safety and purity standards as required by FDA Office of Biologics standards.

C. Formulations and Routes for Administration

Pharmaceutical compositions of the present disclosure comprise an effective amount of one or more candidate substance or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one candidate substance or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The candidate substance may comprise different types of carriers depending on whether it is to be administered in solid, liquid or aerosol form, and whether it need to be sterile for such routes of administration as injection. The present disclosure can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, subcutaneously, subconjunctival, intravesicularlly, mucosally, intrapericardially, intraumbilically, intraocularally, orally, locally, via inhalation (e.g., aerosol inhalation), via injection, via infusion, via continuous infusion, via localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present disclosure administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The candidate substance may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present disclosure. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the candidate substance is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the disclosure, the oral composition may be prepared as a syrup or elixir. A syrup or elixir, and may comprise, for example, at least one active agent, a sweetening agent, a preservative, a flavoring agent, a dye, a preservative, or combinations thereof.

In certain particular embodiments, an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

D. Combined Therapy

In the context of the present disclosure, it is contemplated that the compounds may be used in combination with each other to more effectively treat melanoma. When multiple therapeutic agents are administered, as long as the dose of the additional therapeutic agent does not exceed previously quoted toxicity levels, the effective amounts of the additional therapeutic agent may simply be defined as that amount effective to exert a therapeutic effect when administered to an animal in combination with the primary agent. This may be easily determined by monitoring the animal or patient and measuring those physical and biochemical parameters of health and disease that are indicative of the success of a given treatment. Such methods are routine in animal testing and clinical practice.

To kill or slow the growth of a cancer cell using the methods and compositions of the present disclosure, one can provide to the subject a combination of agents. These compositions would be provided in a combined amount effective to effect a therapeutic benefit (inhibition of cancer cell growth, reduction in tumor size, induction of apoptosis in a cancer cell, etc.). This process may involve administering a combination at the same time. This may be achieved by administering a single composition or pharmacological formulation that includes both agents, or by administering two distinct compositions or formulations, at the same time.

Alternatively, treatment with one agent may precede or follow the additional agent treatment by intervals ranging from minutes to weeks. In embodiments where the additional agent is administered separately to the patient, one would generally ensure that a significant period of time did not expire between the time of each delivery, such that the agents would still be able to exert an advantageously combined effect on the cell. In such instances, it is contemplated that one would contact the cell with both modalities within about 12-24 hr of each other and, more preferably, within about 6-12 hr of each other, with a delay time of only about 12 hr being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either or both agents will be desired. Various combinations may be employed, where a taxane/gemcitabine is "A" and the Axl kinase inhibitor is "B," as exemplified below:

| | | | | | |
|---|---|---|---|---|---|
| A/B/A | B/A/B | B/B/A | A/A/B | B/A/A | A/B/B |
| B/B/B/A | B/B/A/B | A/A/B/B | A/B/A/B | A/B/B/A | B/B/A/A |
| B/A/B/A | B/A/A/B | B/B/B/A | A/A/A/B | B/A/A/A | A/B/A/A |
| A/A/B/A | A/B/B/B | B/A/B/B | B/B/A/B | | |

III. Methods of Screening

A. Mouse Models

Embodiments of the present disclosure provide an animal model with a Rgs16::GFP transgene and Kras mutation. For example, Kras mutations include G12C, G12D, G12V, G12A, G12S, G12R, G13D, G13C, Q61R, and Q61L. In exemplary methods, the Kras mutation is a KrasG12D mutation.

Kirsten rat sarcoma viral oncogene homolog (Kras), is a protein that in humans is encoded by the Kras gene. The protein product of the normal Kras gene performs an essential function in normal tissue signaling, and the mutation of a Kras gene is an essential step in the development of many cancers. Like other members of the ras subfamily, the Kras protein is a GTPase and is an early player in many signal transduction pathways. Kras is usually tethered to cell membranes because of the presence of an isoprene group on its C-terminus. Kras-mediated cancers include pancreatic cancer, colon cancer, lung cancer, and leukemias. In particular, methods of the present disclosure can be used to screen for candidate drugs for pancreatic ductal adenocarcinoma (PDA).

Suitable animals for use as models are preferably mammalian subjects, most preferably convenient laboratory animals such as rabbits, rats, mice, and the like. For closer analogy to human subjects, primates could also be used. Particularly useful are subjects that are particularly susceptible to tumor development, such as subjects with impaired immune systems, typically nude mice or SCID mice. Any appropriate vertebrate subject can be used, the choice being dictated mainly by convenience and similarity to the system of ultimate interest.

In certain embodiments, the animal model is a genetically engineered mouse model such as for pancreatic ductal adenocarcinoma. Over the last decade, several models, primarily based on the genetic activation of resident Kras oncogenes knocked-in within the endogenous Kras locus have been generated. These models faithfully reproduce the histological lesions that characterize human pancreatic tumors. Decoration of these models with additional mutations, primarily involving tumor suppressor loci known to be also mutated in human PDA tumors, results in accelerated tumor progression and in the induction of invasive and metastatic malignancies. Mouse PDAs also display a desmoplastic stroma and inflammatory responses that closely resemble those observed in human patients. Interestingly, adult mice appear to be resistant to PDA development unless the animals undergo pancreatic damage, mainly in the form of acute, chronic or even temporary pancreatitis.

An Rgs16::GFP transgenic mouse can be produced by methods known in the art for creating transgenic mice. Methods for generating transgenic animals of the present invention, including knock-outs and knock-ins, are well known in the art (see, generally, Gene Targeting: A Practical Approach, Joyner, ed., Oxford University Press, Inc. (2000)). The transgene is introduced into the cell, directly or indirectly by introduction into a precursor of the cell, e.g., by microinjection, transfection or infection, e.g., by infection with a recombinant virus. The term genetic manipulation includes the introduction of a recombinant DNA molecule. This molecule may be integrated within a chromosome, or it may be extrachromosomally replicating DNA.

Expression systems can be prepared using methods known in the art. For example, an expression system can be prepared as part of a larger plasmid. Such preparation allows the cloning and selection of the correct constructions in an efficient manner as is known in the art. Expression systems can be located between convenient restriction sites on the plasmid so that they can be easily isolated from the remaining plasmid sequences for incorporation into the desired mammal. Preferably, the DNA construct encoding Rgs16 (Accession NO. NM_002928.3) comprises a bacterial artificial chromosome including the naturally associated transcriptional regulatory sequences to provide for tissue specific expression.

The various methods employed in the preparation of the plasmids and transformation of host organisms are known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17.

An expression system or construct encoding a transgene as described herein can also include a 3' untranslated region downstream of the DNA sequence. Such regions can stabilize the RNA transcript of the expression system and thus increases the yield of desired protein from the expression system. Among the 3' untranslated regions useful in the constructs of this invention are sequences that provide a poly A signal.

In another embodiment, the targeting construct may contain more than one selectable maker gene, including a negative selectable marker, such as the herpes simplex virus tk (HSV-tk) gene, which is preferably positioned outside one or both of the homologous arms of the targeting construct. The negative selectable marker may be operatively linked to a promoter and a polyadenylation signal (see, e.g., U.S. Pat. Nos. 5,464,764; 5,487,992; 5,627,059 and 5,631,153).

Once an appropriate targeting construct has been prepared, the targeting construct may be introduced into an appropriate host cell using any method known in the art. Various techniques may be employed in the present invention, including, for example: pronuclear microinjection; retrovirus mediated gene transfer into germ lines; gene targeting in embryonic stem cells; electroporation of embryos; sperm-mediated gene transfer; and calcium phosphate/DNA co-precipitates, microinjection of DNA into the nucleus, bacterial protoplast fusion with intact cells, transfection, polycations, e.g., polybrene, polyornithine, etc., or the like (see, e.g., U.S. Pat. No. 4,873,191; Van der Putten et al., 1985, Proc. Natl. Acad. Sci., USA 82:6148-6152; Thompson et al., 1989, Cell 56:313-321; Lo, 1983, Mol Cell. Biol. 3:1803-1814; Lavitrano et al., 1989, Cell, 57:717-723). Various techniques for transforming mammalian cells are known in the art. (see, e.g., Gordon, 1989, Intl. Rev. Cytol., 115:171-229; Keown et al., 1989, Methods in Enzymology; Keown et al., 1990, Methods and Enzymology, Vol. 185, pp. 527-537; Mansour et al., 1988, Nature, 336:348-352).

Any cell type capable of homologous recombination may be used in the practice of the present invention. Examples of such target cells include cells derived from vertebrates including mammals such as humans, bovine species, ovine species, murine species, simian species, and ether eukaryotic organisms such as filamentous fungi, and higher multicellular organisms such as plants.

Preferred cell types include embryonic stem (ES) cells, which are typically obtained from pre-implantation embryos cultured in vitro (see, e.g., Evans, M. J. et al., 1981, Nature 292:154-156; Bradley, M. O. et al., 1984, Nature 309:255-258; Gossler et al., 1986, Proc. Natl. Acad. Sci. USA 83:9065-9069; and Robertson et al., 1986, Nature 322:445-448). The ES cells are cultured and prepared for introduction of the targeting construct using methods well known to the skilled artisan. (see, e.g., Robertson, E. J. ed. "Teratocarcinomas and Embryonic Stem Cells, a Practical Approach", IRL Press, Washington D.C., 1987; Bradley et al., 1986, Current Topics in Devel. Biol. 20:357-371; by Hogan et al., in "Manipulating the Mouse Embryo": A Laboratory Manual, Cold Spring Harbor Laboratory Press, Cold Spring Harbor N.Y., 1986; Thomas et al., 1987, Cell 51:503; Koller et al., 1991, Proc. Natl. Acad. Sci. USA, 88:10730; Dorin et al., 1992, Transgenic Res. 1:101; and Veis et al., 1993, Cell 75:229). The ES cells that will be inserted with the targeting construct are derived from an embryo or blastocyst of the same species as the developing embryo into which they are to be introduced. ES cells are typically selected for their ability to integrate into the inner cell mass and contribute to the germ line of an individual when introduced into the mammal in an embryo at the blastocyst stage of development. Thus, any ES cell line having this capability is suitable for use in the practice of the present invention.

After the targeting construct has been introduced into cells, the cells in which successful gene targeting has occurred are identified. Insertion of the targeting construct into the targeted gene is typically detected by identifying cells for expression of the marker gene. In a preferred embodiment, the cells transformed with the targeting construct of the present invention are subjected to treatment with an appropriate agent that selects against cells not expressing the selectable marker. Only those cells expressing the selectable marker gene survive and/or grow under certain conditions. For example, cells that express the introduced neomycin resistance gene are resistant to the compound G418, while cells that do not express the neo gene marker are killed by G418. If the targeting construct also comprises a screening marker such as GFP, homologous recombination can be identified through screening cell colonies under a fluorescent light. Cells that have undergone homologous recombination will have deleted the GFP gene and will not fluoresce.

Due to the high stability and relatively large inserts, ease of manipulation and shotgun sequencing, bacterial artificial chromosome (BAC) libraries can provide human sequences for genes of interest. BAC libraries contain an average insert size of 100-150 kb. BAC clones are capable of harboring inserts as large as 300,000 base pairs. Shizuya, et al., (1992) Proc. Natl. Acad. Sci., USA 89:8794-8797; Kim, et al., (1996) Genomics 34 213-218; Swiatek, et al., (1993) Genes and Development 7:2071-2084. Genomic BAC libraries of the human and mouse have been constructed and are commercially available (Invitrogen, Carlsbad Calif.). Genomic BAC libraries can also serve as a source of human and murine CD20 gene sequences as well as transcriptional control regions. For example, a BAC vector such as pLD53 is modified by homologous recombination in *E. coli* to introduce the transgenic construct such as Rgs::GFP into the BAC vector. The modified BAC DNA is then injected by pronuclear injection of fertilized mouse oocytes to pseudopregnant female mice. The pups are then tested by various methods such as PCR for the presence of the transgene.

The label used in the various aspects of the disclosure is green fluorescent protein (GFP). The native gene encoding this protein has been cloned from the bioluminescent jellyfish Aequorea Victoria (Morin, J. et al., J Cell Physiol (1972) 77:313-318). The availability of the gene has made it possible to use GFP as a marker for gene expression. GFP itself is a 283 amino acid protein with a molecular weight of 27 kD. It requires no additional proteins from its native source nor does it require substrates or cofactors available only in its native source in order to fluoresce. (Prasher, D. C. et al., Gene (1992) 111:229-233; Yang, F. et al., Nature Biotechnol (1996) 14:1252-1256; Cody, C. W. et al., Biochemistry (1993) 32:1212-1218.) Mutants of the GFP gene have been found useful to enhance expression and to modify excitation and fluorescence. GFP-S65T (wherein serine at 65 is replaced with threonine) is particularly useful in the invention method and has a single excitation peak at 490 nm. (Heim, R. et al., Nature (1995) 373:663-664); U.S. Pat. No. 5,625,048. Other mutants have also been disclosed by Delagrade, S. et al., Biotechnology (1995) 13:1.51-154; Cormack, B. et al., Gene (1996) 173:33-38 and Cramer, A. et al. Nature Biotechnol (1996) 14:315-319. Additional mutants are also disclosed in U.S. Pat. No. 5,625,048. By suitable modification, the spectrum of light emitted by the GFP can be altered. Thus, although the term "GFP" is used in the present application, the proteins included within this definition are not necessarily green in appearance. Various forms of GFP exhibit colors other than green and these, too, are included within the definition of "GFP" and are useful in the methods and materials of the invention. In addition, it is noted that green fluorescent proteins falling within the definition of "GFP" herein have been isolated from other organisms, such as the sea pansy, Renilla reriformis. Any suitable and convenient form of the GFP gene can be used to modify the tumor cells useful in the models of the invention, and for retroviral transformation of endogenous tumors. The particular humanized hGFP-S65T clone is used in the examples set forth below for illustration. Techniques for labeling cells in general using GFP are disclosed in U.S. Pat. No. 5,491,084, incorporated herein by reference.

Pancreatic adenocarcinoma mouse models have an activating mutation of Kras and any one or more tumor suppressor genes has decreased or lack of expression, such as deletion of all or a portion of the one or more genes encoding the tumor suppressor gene. For example, the tumor suppressor gene is Ink4a/Arf, Ink4a, Arf p53, Smad4/Dpc, Lkb1, Brca2, or Mlh1. In one embodiment, the pancreatic and duodenal homeobox gene 1 (Pdx1)-Cre transgene is used to delete said one or more tumor suppressor genes or loci in the pancreas. For example, the activating Kras mutation is a KrasG12D knock-in allele (LSL-Kras). Animal models have been engineered to bear both a pancreas-specific Cre-mediated mutant Kras allele (KrasG12D) (Jackson, et al. (2001) Genes Dev. 15:3243) and a deletion of a conditional Ink4a/Arf allele (Ink4a/Arflox). The Kras allele is a 'knock-in,' i.e., it is controlled by its endogenous promoter. The Kras allele, KrasG12D, carries an activating mutation (G12D), which results in the constitutive expression of Kras. Therefore, in the animal model, Kras is expressed at a level that mimics expression of the gene in human pancreatic adenocarcinoma. For Cre recombinase expression, the Pdx1-Cre transgene (Gu G. et al. (2002) Development 129, 2447-2457), which produces Cre activity in all the acinar, islet and duct cells and deletes loxP containing alleles in all pancreatic lineages, was employed. Kras is therefore activated at endogenous levels and Ink4a/Arf is deleted specifically in all cells of the pancreas.

Exemplary genetically engineered mouse models of PDA for used with the methods of the present disclosure are KC (i.e., $Kras^{LSL-G12D}$; $p48^{Cre}$) and KIC (i.e., $Kras^{LSL-G12D}$; Ink4a$^{flox/flox}$; $p48^{cre}$) (U.S. Patent Publication No. 20080242742, incorporated herein by reference). Animals bearing the combination of these mutant alleles develop focal premalignant ductal lesions, termed pancreatic intraepithelial neoplasias (PanINs, as used herein) which rapidly and faithfully progress to highly aggressive, invasive and metastatic tumors which ultimately result in death of the animals by 11 weeks of age.

Embodiments of the present invention concern a transgenic mouse model with an Rgs::GFP transgene and a Kras mutation. Exemplary transgenic mouse models include Rgs16::GFP;KC or Rgs16::GFP;KIC reporter mice. These mice are produced by crossing Rgs16::GFP BAC transgenic mice with KC or KIC mice and selecting for transgenic mice by PCR for $p48^{cre}$, LSL-Kras$^{G12D}$, and Cdkn2a and detection of GFP in the brain of newborn pups or in the retina of adult mice. Typically, crossing and backcrossing is accomplished by mating siblings or a parental strain with an offspring, depending on the goal of each particular step in the breeding process. In certain cases, it may be necessary to generate a large number of offspring in order to generate a single offspring that contains each of the knockout constructs and/or transgenes in the proper chromosomal location. In addition, it may be necessary to cross or backcross over several generations to ultimately obtain the desired genotype.

In a further embodiment, an Rgs16 knockout mouse can be produced by methods known in the art. In particular, a double Rgs8-Rgs16 knockout mouse can be produced. The term "knockout" is defined as the endogenous Rgs16 and Rgs8 loci no longer producing functional Rgs16 and Rgs8 proteins. These knockouts can be made in many ways, by for example, disrupting one or more of the exons of Rgs16 and Rgs8. This disruption can take place in a variety of ways, through for example, homologous recombination events, which substitute non-Rgs8-16 coding sequence, such as a marker gene, such as the neo gene, for Rgs8-16 coding sequence, or the lacZ gene. The knockouts could also be made with inducible expression systems, such as a Cre/lox system, so that the disruption of the Rgs8-16 genes is inducible, for example, through tissue specific promoters of Cre. It is understood that the knockouts can be made by disrupting any exon or multiple exons of the Rgs8-16 genes. The disruption can include for example, a point mutation, which alters the protein sequence or a point deletion which causes a missense polypeptide to be produced, or deletions or alterations so any fragment of the Rgs8-16 genes is disrupted which disrupts Rgs8-16 protein production.

An Rgs8-Rgs16 double knockout mouse can be used to study the tumor suppressor function of both Rgs8 and Rgs16. In certain embodiments, the Rgs8-Rgs16 double knockout mouse is crossed with KC or KIC mice and selected for transgenic KC-R (i.e., LSL-Kras$^{G12D}$; $p48^{Cre}$; Rgs8$^{-/-}$16$^{-/-(DKO)}$) mice. In exemplary methods, the KC-R mice die before 4 months of age because they can not maintain energy homeostasis as Rgs8 and Rgs16 are required in the liver to conserve energy utilization in malnourished mice. Once the KC-R mice develop PDA, they rapidly progress to aggressive metastasis to liver and lung.

Transgenic offspring of the surrogate host may be screened for the presence and/or expression of the transgene in the desired tissue, cell or animal by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

B. Candidate Therapeutics

The present disclosure provides methods to screen for candidate therapeutics for Kras-mediated cancers. The in vivo assay comprises an animal model with a Rgs16::GFP transgene and Kras mutation. For example, Kras mutations include G12C, G12D, G12V, G12A, G12S, G12R, G13D, G13C, Q61R, and Q61L. In exemplary methods, the Kras mutation is a Kras$^{G12D}$ mutation.

In some aspects, the mice are treated with the drug or drug combination at an early PanIN stage. Early PanIN lesions begin at about 2 to about 3 weeks of age. The drug can be administered between postnatal P15 and postnatal P29. The drug can be administered at multiple times such as 2, 3, 4, or 5 times. The mice are sacrificed at about 1 to 3 weeks after the first treatment, such as about 2 weeks.

A candidate drug is identified by a decrease of Rgs16::GFP fluorescence intensity. The decrease in fluorescence intensity correlates with tumor size and number of tumor initiation sites. In certain aspects, the distribution and intensity of Rgs::GFP expression is proportional to and coincident with tumor burden. The fluorescence can be measured in dissected organs. In exemplary methods, the pancreas is dissected under a fluorescence dissection microscope to quantitate GFP expression. Tissue samples are simply properly processed as fresh samples in slices of suitable size, typically 1 mm thick, and placed under a microscope for examination. Even colonies of less than 10 cells are thus visible. A variety of microscopic visualization techniques is known in the art and any appropriate method can be used. Methods of determining GFP fluorescence intensity are known in the art. For example, images of the brightest non-overlapping fields of GFP expression are collected to represent the regions of greatest tumor burden and quantified using NIH ImageJ software with background subtraction.

In one embodiment, however, it is unnecessary to remove organ tissues; rather, the fluorescence can be visualized in the whole animal by real-time fluorescence optical tumor imaging (FOTI).

As used herein, the term "compound" refers to any chemical entity, pharmaceutical, drug, and the like that can be used to treat or prevent a disease, illness, conditions, or disorder of bodily function. Compounds comprise both known and potential therapeutic compounds. A compound can be determined to be therapeutic by screening using the screening methods of the present invention. Examples of test compounds include, but are not limited to peptides, polypeptides, synthetic organic molecules, naturally occurring organic molecules, nucleic acid molecules, and combinations thereof.

In some embodiments, the candidate drug can be, without limitation, a peptide (e.g., peptidomimetic), protein (e.g., an antibody), small molecule, natural or synthetic nucleic acid (e.g., siRNA, miRNA), enzyme (e.g., kinase) or any combination or analog thereof. For example, peptide candidate substance may be peptides with L-amino acids and/or D-amino acids, phosphopeptides, and other types of peptides. The screened peptides may be of any size, but are particularly less than about 50 amino acids. Exemplary candidate drugs include inhibitors of angiogenesis, Gas6-Axl, DDR1, DDR2, PI3K, mTor, CTGF antibodies, and Smac/Diablo mimetics. The candidate drug can be administered alone or in combination with other drugs such as Gemcitabine and/or Paclitaxel.

In certain aspects, the candidate drugs are provided in library formats known in the art, such as in chemically synthesized libraries, recombinantly expressed libraries (e.g., phage display libraries), and in vitro translation-based libraries (e.g., ribosome display libraries).

The candidate drug identified by the in vivo assay in the Rgs16:GFP mice can be further validated. For example, human xenografts and subsequent human clinical trials can be used for further validation.

In yet another aspect, the invention also provides for the use of the animal models of the invention for the generation of cell lines which may be used to study the disease biology of pancreatic adenocarcinoma, e.g., for studies of heterotypic tumor-stroma interaction and identification of Kras in tumor maintenance program.

The genetically comparable, early passage mouse cell lines of the invention are useful for understanding the disease biology by, for example, studies of the basis for the heterotypic interactions between tumor and stroma using co-culture, gene expression profiling and manipulation of specific gene expression in either cell type (Olumi, A. F., et al. (1999) Cancer Res 59, 5002-5011; Tlsty, T. D., and Hein, P. W. (2001) Curr Opin Genet Dev 11, 54-59).

The cell lines of the invention may also be used for the discovery of new drug targets that disrupt the tumor-stromal symbiosis, such as, for example, compounds which not only target tumors cells directly but also exert an indirect effect by suppressing growth and survival signals elaborated by the microenvironments' interaction with the tumor cells.

C. Biomarkers

Further embodiments of the present disclosure provide methods for identifying biomarkers of pancreatic insufficiency, PanINs and PDA. In certain aspects, the Rgs16:GFP KIC mice are used to identify biomarkers of PanINs and PDA including early metabolic markers of pancreatic insufficiency. These markers appear during disease progression such as overeating, engorged intestines, large quantity of feces, hypoglycemia, weight loss, feces enriched in lipids and or/carbohydrates. The method comprises comparing the expression of a gene or protein in a sample from the Rgs16::GFP KIC mouse to the expression in a control mouse or non-cancerous tissue from the same mouse.

The term "expression" is used herein to mean the process by which a polypeptide is produced from DNA. The process involves the transcription of the gene into mRNA and the translation of this mRNA into a polypeptide. Depending on the context in which used, "expression" may refer to the production of RNA, protein or both.

Expression of a biomarker may be assessed by any of a wide variety of well known methods for detecting expression of a transcribed molecule or its corresponding protein. Non-limiting examples of such methods include immunological methods for detection of secreted proteins, protein purification methods, protein function or activity assays, nucleic acid hybridization methods, nucleic acid reverse transcription methods, and nucleic acid amplification methods. In a preferred embodiment, expression of a marker gene is assessed using an antibody (e.g., a radio-labeled, chromophore-labeled, fluorophore-labeled, or enzyme-labeled antibody), an antibody derivative (e.g., an antibody conjugated with a substrate or with the protein or ligand of a protein-ligand pair {e.g., biotin-streptavidin}), or an antibody fragment (e.g., a single-chain antibody, an isolated antibody hypervariable domain, etc.) which binds specifically with a protein corresponding to the marker gene, such as the protein encoded by the open reading frame corresponding to the marker gene or such a protein which has undergone all or a portion of its normal post-translational modification. In another preferred embodiment, expression of a marker gene is assessed by preparing mRNA/cDNA (i.e. a transcribed polynucleotide) from cells in a patient sample, and by hybridizing the mRNA/cDNA with a reference polynucleotide which is a complement of a polynucleotide comprising the marker gene, and fragments thereof cDNA can, optionally, be amplified using any of a variety of polymerase chain reaction methods prior to hybridization with the reference polynucleotide; preferably, it is not amplified.

In one embodiment, the expression of the biomarkers is detected using mass spectroscopy. In another embodiment, the expression of the biomarker is detected by detecting the mRNA transcription levels of the gene encoding said at one or more biomarker. In yet another embodiment, the expression of the biomarkers can be detected by RNA-sequencing, ELISA, RCA immunoassay, chemiluminescence, thin-film optical biosensor, proton resonance technology, protein microarray assay or any other detection method known in the art.

A person of skill in the art would be able to identify biomarkers which are potentially associated with cancer. Such biomarkers can be selected from the group consisting of as oncogenes, tumor suppressor genes, growth factor-like genes, protease-like genes, and protein kinase-like genes.

In one embodiment, the sample is a body fluid sample. In one embodiment, the body fluid sample is blood or serum. In some embodiments, the biomarkers are molecular markers identified in blood, pancreatic juice or feces. These markers can be used to identify subjects at high risk for developing PDA, and subjects identified with PanIN3 or PDA are candidates for tumor resection and/or neoadjuvant treatment.

In other embodiments, cultured primary PDA cells of the Rgs16::GFP mice are analyzed to identify biomarkers of pancreatic insufficiency, PanINs or PDA. Primary Rgs16::GFP PDA cells are harvested from the mice and cultured in growth media.

The sample can be derived from any biological source, including all body fluids (such as, for example, whole blood, plasma, serum, saliva, ocular lens fluid, sweat, urine, milk, etc.), tissue or extracts, cells, etc.

In a further embodiment, the biomarker identified by the methods of the present disclosure are used to identify a subject with pancreatic insufficiency. The subject can be treated with neoadjuvant therapy. The subject can be a mammal such as a human.

The disclosure also comprises kits for diagnosing or aiding in the diagnosis of cancer or for monitoring cancer. The kits can be used to diagnose or monitor any cancer. In one embodiment, the kit is for the diagnosis or monitoring of pancreatic cancer. The reagents may be labeled compounds or agents capable of detecting a polypeptide or an mRNA encoding a polypeptide corresponding to a marker gene of the invention in a biological sample and means for determining the amount of the polypeptide or mRNA in the sample (e.g., an antibody which binds the polypeptide or an oligonucleotide probe which binds to DNA or mRNA encoding the polypeptide). Suitable reagents for binding with a polypeptide corresponding to a marker gene of the invention include antibodies, antibody derivatives, antibody fragments, and the like. Suitable reagents for binding with a nucleic acid (e.g., a genomic DNA, an mRNA, a spliced mRNA, a cDNA, or the like) include complementary nucleic acids.

IV. Examples

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Materials and Methods

Mouse lines and genotyping. KIC (p48$^{Cre/+}$; Kras$^{G12D/+}$; Cdkn2a$^{f/f}$); KC, (p48$^{Cre/+}$; Kras$^{G12D/+}$); IC (p48$^{Cre/+}$; Cdkn2a$^{f/f}$); Rgs16::GFP; KIC, KIC mice were crossed with Rgs16::GFP BAC transgenic mice to generate Rgs16::GFP; p48$^{Cre/+}$;Kras$^{G12D/+}$;Cdkn2a$^{f/f}$ (Rgs16::GFP;KIC) reporter mice. Genotyping was done using clipped tails before sacrifice and confirmed with spleen DNA after dissection. Mice were maintained at a 12 hr day-12 hr night cycle on normal chow ad libitum according to the rules and standards of UT Southwestern Institutional Animal Care and Use Committee. Rgs16 mice were identified by blue light excitation of GFP in brain of newborn pups or in retina of adult mice. Genotyping of KIC mice was done with the following primers: p48$^{Cre}$ (For: 5'-CCTGGAAAATGCTTCTGTCCG-3' (SEQ ID NO: 1); Rev: 5'-CAGGGTGTTATAAGCAATCCC-3' (SEQ ID NO: 2); Product: 392 bp), LSL-Kras$^{G12D}$ (For: 5'-CTAGCCACCATGGCTTGAGT-3' (SEQ ID NO: 3); Rev: 5'-TCCGAATTCAGTGACTACAGATG-3' (SEQ ID NO: 4); Product: 327 bp), and Cdkn2a$^{f/f}$ (For: 5'-TTGTTG-GCCCAGGATGCCGACATC-3' (SEQ ID NO: 5); Rev: 5'-CCAAGTGTGCAAACCCAGGCTCC-3' (SEQ ID NO: 6); Product: 145 by for WT, 179 by for loxP inserted allele). All PCR conditions started with genomic denaturation at 94° C. for 10 min followed by 33 cycles of 94° C. denaturation for 30 sec, 60° C. annealing for 1 min, and 72° C. elongation for 1 min. PCR products were run in a 1% agarose gel.

Fluorescent microscopy and GFP quantification. Pancreatic expression of Rgs16::GFP in GFP-PDA mice was quantified using a Zeiss Lumar microscope. Images were captured using a single-channel camera (Hamamatsu) in 1344×1024 resolution with 1 sec exposure under 48× magnification with 1×1 binning, analog gain=10, and analog offset=2 settings. Pancreatic fields representing the tumor burden (3-4 fields for P15 pups and 5 or more for pups from P23 onwards) of the pancreas were imaged covering up to 50% of the organ surface area. All images were saved in gray-scale 16-bit tiff format. Images were quantified using NIH ImageJ software with background subtraction with a radius of 50 pixels. A variable and tight threshold was set to eliminate residual background. Intensities of all particles with size ≥5 pixels were summed to obtain the total light intensity per image.

Tissue clearing and microscopy. Pancreata and a small section of duodenum containing the ampulla of Vater were dissected, fixed overnight in PFA, washed in PBS (4° C.). Tissues were stored in PBS (4° C.). Tissue clearing and microscopy was done as described by Soderblom (Soderblom et al., 2015), based on Becker et al., (Becker et al., 2012, Kopp et al., 2012, Krah et al., 2015). Production of the three dimensional (3D) rotational movie was done as described by Soderblom (Soderblom et al., 2015) using IMARIS.

Drug dosages. GFP-PDA mice were injected intraperitoneally with gemcitabine (Eli Lilly; Indianapolis, Ind., USA) (12.5 mg/kg/day given 3 days/week, dissolved in PBS), Abraxane (Cellgene; Summit, N.J., USA) (5 mg/kg/day given 2 days/week, diluted in 2% saline solution), BGB324 (BerGenBio, Bergen, Norway) (5 mg/kg/day given 5 days/week, dissolved in a mix of DMSO:ethanol:Kolliphor EL:water with 4:4:8:84 v/v ratio), and warfarin (0.2 mg/kg/day given 5 days/week, dissolved in PBS) according to injection schedules specified below. These doses were validated in prior mouse studies (Dineen et al., 2010; Kutluk Cenik et al., 2013; Ostapoff et al., 2013; Aguilera et al., 2014; Ostapoff et al., 2014). Note that 30% cyclodextrin was discontinued as a vehicle for BGB324 (v2B, v2G) because it was not active. GA was not affected (FIGS. 17A-C; GA_v2B, GA_v2G). To verify tumor progression remains constant over the duration of these experiments, assays of untreated mice were interspersed with drug-treated cohorts, and warfarin-treated pups were the final cohort the inventors tested. Gemcitabine, Abraxane and warfarin were purchased from the UT Southwestern clinical pharmacy; BGB324 was a gift from BerGenBio.

Rgs16::GFP PDA primary cell culture. Primary Rgs16::GFP PDA cells were harvested from 6-week-old KIC mice. Cells were grown in 25 mM Glucose DMEM (HyClone) with 10% FBS (Serum Source International), penicillin and streptomycin (Life Technologies) on rat tail collagen typeI (BD Biosciences) coated plates (0.5 μg/cm$^2$) in a humidified incubator at 37° C. and 5% $CO_2$. Cells reaching confluency were washed twice with PBS (HyClone) and lifted with 0.05% Trypsin-EDTA (HyClone) treatment up to 10 min in the incubator. For drug tests in FIGS. 20A-D, primary PDA cells were incubated with gemcitabine (10 µM dissolved in PBS), warfarin (1 µM or 10 µM dissolved in water), BGB324 (1 µM or 10 µM dissolved in DMSO) or warfarin and BGB324 together for 24 hrs in 37° C. incubator. PDA live cell numbers were obtained via counts using a hemocytometer following 2% trypan blue staining to distinguish dead cells under an inverted microscope.

PDA primary cell RNA-Seq. Cultured Rgs16::GFP PDA cells were stimulated with 40% FBS containing growth medium incubation overnight and subjected to FACS to separate the GFP positive and negative cell populations. After isolating RNA via TRIzol (Life Technologies) treatment, the transcriptional profile of each GFP-PDA population was revealed via RNA-Seq performed on poly-A selected mRNA. Mouse sequence reads were aligned to the mm9 genome assembly using TopHat v2.0.9 (Trapnell et al., 2009). All default settings were used except: -G option and -no-novel-juncs. The Cuffdiff module available in Cufflinks software v2.1.1 was used to quantify the expression by the FPKM method (Trapnell et al., 2010, Trapnell et al., 2012). The geometric method (median of the geometric means of fragment counts across libraries) was used to normalize and scale FPKM values.

Dendrogram—Mouse PDA culture and tissues. The inventors calculated pairwise distances between all array sample expression data using "euclidean" method in dist ( ) R function to check the similarities between samples. This method calculates the distance between the two vectors. They performed hierarchical clustering on this distance matrix using "ward" method in hclust ( ) R function.

Dendrogram—TCGA RNA-Seq. The inventors extracted pancreatic adenocarcinoma patient samples (n=178) mRNA expression data available from the cancer genome atlas (TCGA). These data contain normalized genes expression in terms of transcripts per million (TPM) and these values were used for the further analysis. To compare expression levels in the human PDA tumor samples with mouse samples, the inventors used the NCBI homologene database to extract mouse homolog genes for human genes. From this list, they selected genes that show ≥10 TPM in at least 10% of the human primary tumor samples. This filter retained 10,135 genes used to plot the dendrogram.

Multidimensional scaling. The inventors used multidimensional scaling (MDS) to assess the differences between samples. For this, they used normalized expression matrix for all genes in the genome across all samples and computed distances between each sample pair using euclidean method; cmdscale ( ) in stats R package (Team 2014) was used to represent these distances between each pair of samples in three dimensional space.

Heatmap. Z-score was computed for a selected set of markers in each category across all samples and plotted using heatmap.2 ( ) function available in gplots R package (Warnes et al., 2015).

Statistical analysis of GFP expression. GFP values were converted to $log_{10}$ scale prior to statistical analysis. Graphs and their statistical comparisons were done using Graphpad Prism software with unpaired and two-tailed Student's t test. Significance between groups was indicated as ns (not significant); *$p<0.05$; $p<0.01$; *$p<0.001$; ****$p<0.0001$. Error bars in all the graphs are standard error mean (SEM). See FIGS. 7-8 for additional statistical analysis.

Example 2

Results

Rgs16::GFP is a $Kras^{G12D}$ dependent reporter of PDA initiation and growth. The inventors introduced the Rgs16::GFP reporter into KC and KIC mice because PDA initiates in pancreatic duct-like cells, either following ADM or neoplastic growth of progenitor cells, anywhere from the head to the tail of the pancreas (FIGS. 1, 2) but not in the hepatopancreatic duct (FIGS. 9A-F) (Aguirre et al., 2003). The affected cell types are consistent with the expression domain of p48 (Ptf1a) during pancreas development (Kawaguchi et al., 2002). Rgs16::GFP is expressed in embryonic and neonatal pancreatic ducts (Villasenor et al., 2010) and, in adults, in ducts early in the response to chronic high insulin demand and in mid-late gestation in pregnant females (Villasenor et al., 2010). Finally, endogenous Rgs16 is expressed in human PDA (TCGA, cancergenome.nih.gov/; Kim et al., 2010).

Analysis of pancreata harvested from P29 mice demonstrated that Rgs16::GFP expression in pancreatic tumors is dependent on the (heterozygous) $Kras^{G12D}$ allele; KIC and KC mice had high Rgs16::GFP expression (FIG. 1). Pancreata in KIC mice at P29 have widespread ductal neoplasia. No GFP expression was observed in IC mice (FIG. 1), which do not harbor the $Kras^{G12D}$ allele and do not develop tumors. Background fluorescence is minimal in KIC mice lacking the GFP transgene (data not shown).

Figure 10:
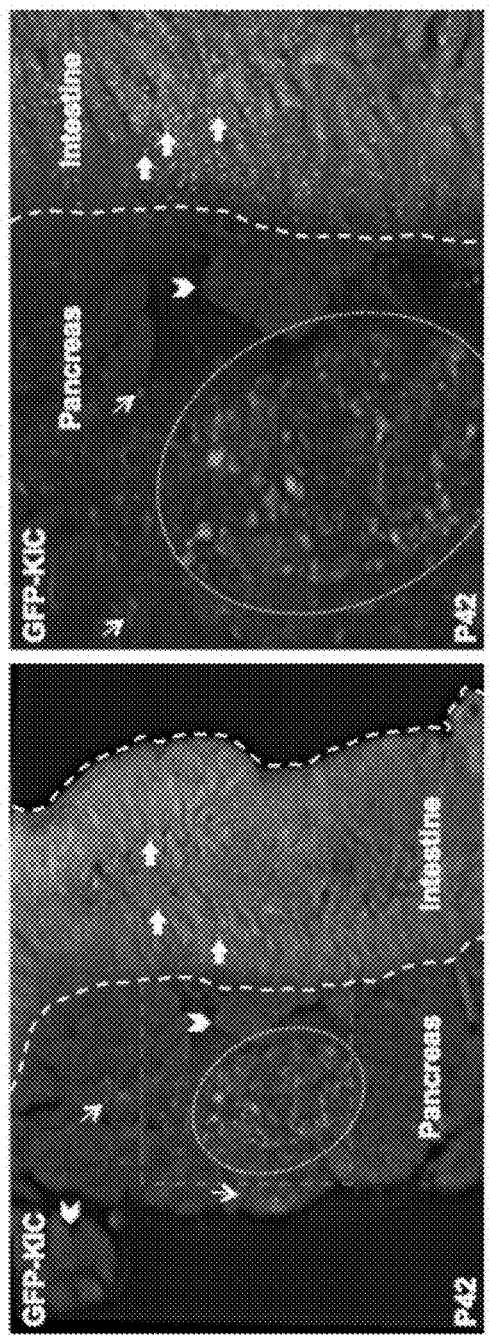
FIG. 10. PDA and PanIN neoplasia in the pancreas head (3D movie). PDA tumor in the head of the pancreas of an Rgs16::GFP;KIC mouse (P42). Light sheet microscopy was used to capture planar images of the duodenum and pancreas head. A computer generated 3D rotational movie shows Rgs16::GFP expression in a PDA tumor (dashed oval), several small areas of neoplasia (thin arrows) and normal acinar cells in lobes of the exocrine pancreas (chevrons). Rgs16::GFP is expressed in presumed neuroendocrine cells (thick arrow heads) within villi of the duodenum (heavy dashed lines). These anatomical features are identified on frame captures of a 3D movie. Left and right panels are low and high magnification cross-sections of the same area and orientation. Area on the left panel marks boundaries of right panel (red dashed rectangle).

An important advantage of the Rgs16::GFP;KIC reporter mice is that the entire pancreas can be rapidly evaluated under a fluorescence dissection microscope to quantitate non-overlapping regions of GFP expression. Every neoplastic lesion detected in bright field microscopy expressed Rgs16::GFP, and vice versa, in hundreds of pancreata dissected at multiple ages (e.g., FIGS. 9A-B). A three dimensional rotational movie shows Rgs16::GFP expression in a PDA tumor, several small areas of neoplasia and normal acinar cells in lobes at the head of the pancreas (FIG. 10).

Rgs16::GFP intensity increases with PDA initiation and growth. In KIC mice, Cre-recombinase is first expressed by the p48 (Ptf1a) promoter in the embryonic progenitor cells that give rise to the three epithelial cell lineages in the adult—ducts, exocrine and endocrine pancreas (Kawaguchi et al., 2002). Therefore, all cells in these pancreatic lineages express oncogenic $Kras^{G12D}$ and have deleted the tumor suppressor gene Cdkn2a (see FIG. 11, the entire pancreas is marked by TdTomato in $p48^{Cre}$;LSL-TdT reporter mice). Despite expression of $Kras^{G12D}$ and deletion of Cdkn2a throughout the pancreas, Rgs16::GFP is only expressed in a few early PanINs sparsely scattered throughout the pancreas two weeks after birth (P15; FIG. 2A). At P15, the pancreas appears to be morphologically and functionally normal, with the exception of these early PanINs. Thus, Rgs16::GFP reports the precise region of activated $Kras^{G12D}$ signaling at tumor initiation and throughout progression.

Between the ages P15 to P29, average GFP fluorescence increased more than 100-fold as early PanINs appeared throughout the pancreas and PDA tumors grew (FIG. 2B). P29 is therefore an optimal time to assess tumor growth in weanlings, as individual tumors achieve near-maximal brightness, more than 10,000-fold above background fluorescence.

Figure 4:
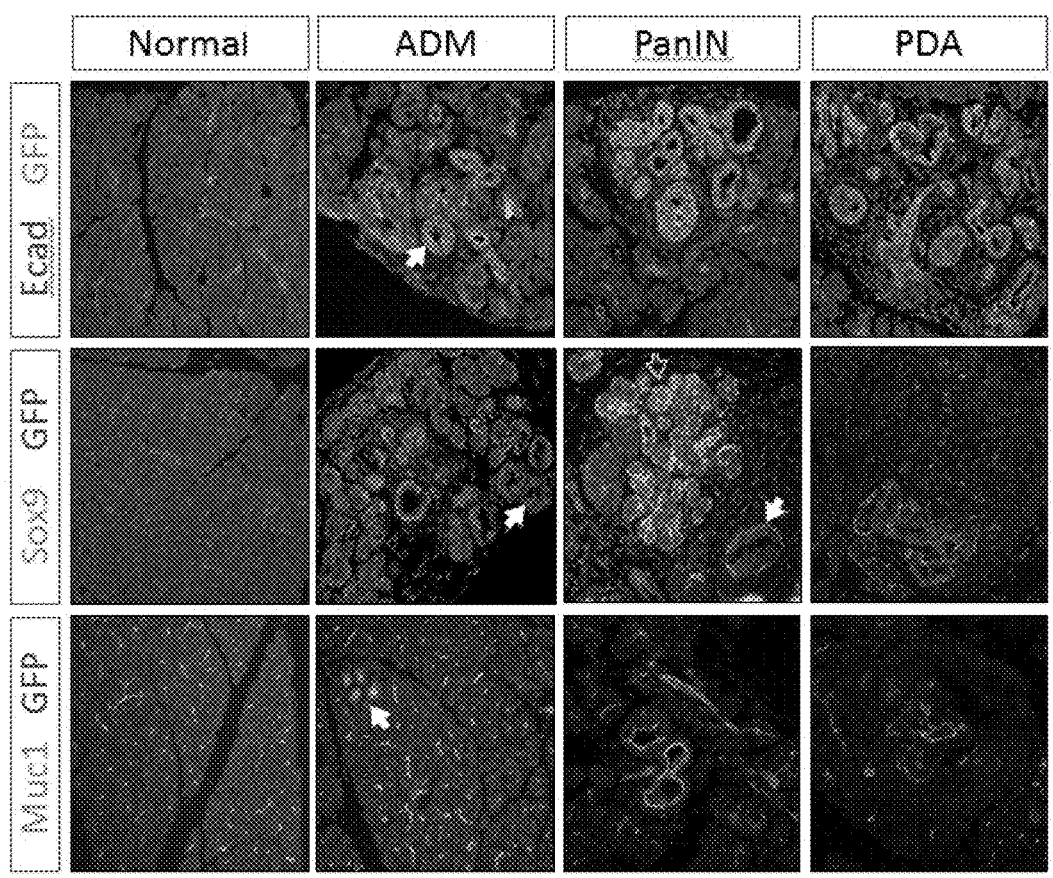
FIG. 4. Rgs16::GFP in ADM, PanIN and PDA. Immunofluorescence of high resolution confocal images showing Rgs16::GFP expression compared to Ecad (red), Sox9 (green) or Muc1 (green) in normal and neoplastic pancreas (ADM, PanIN, PDA) in KIC mice (P29). Primary features of particular interest (e.g., PanIN in the same field as ADM) are indicated by bold white arrows. Other features of interest are indicated by a white outlined arrow.
Figure 12:
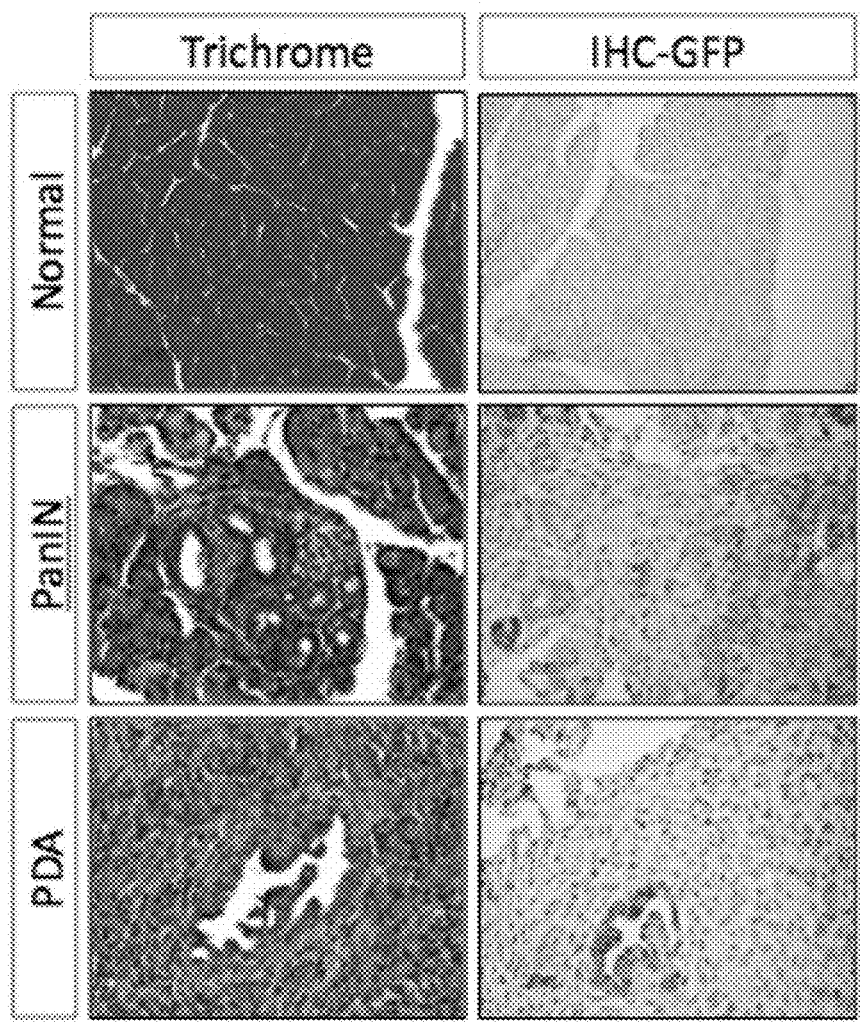
FIG. 12. Rgs16::GFP is expressed in fibrotic PanIN and PDA. Trichrome staining for fibrosis and GFP immunocytochemistry staining (with chicken primary antibody) for Rgs16::GFP expression in Rgs16::GFP; KIC pancreatic sections are shown (P29). Regions of normal acinar morphology, PanIN and PDA are shown. Scale bar=25 μm.
Figure 13:
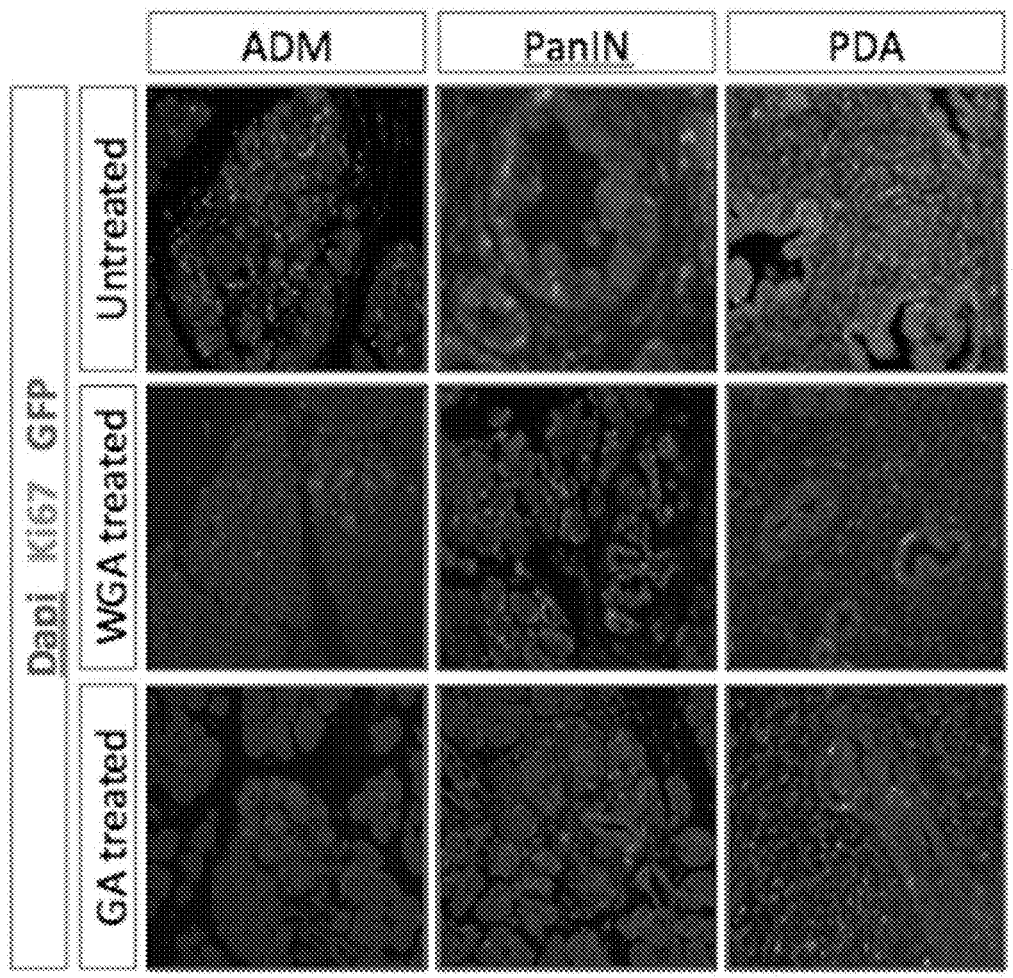
FIG. 13. Rgs16::GFP in ADM, PanIN and PDA. Confocal images of immunofluorescence staining shows relative expression of Rgs16::GFP (red) and Ki67 (green) in normal and neoplastic pancreas (ADM, PanIN, PDA) in untreated and treated (GA or WGA) KIC mice (P29). DAPI (blue) stains nuclei.
Figure 14:
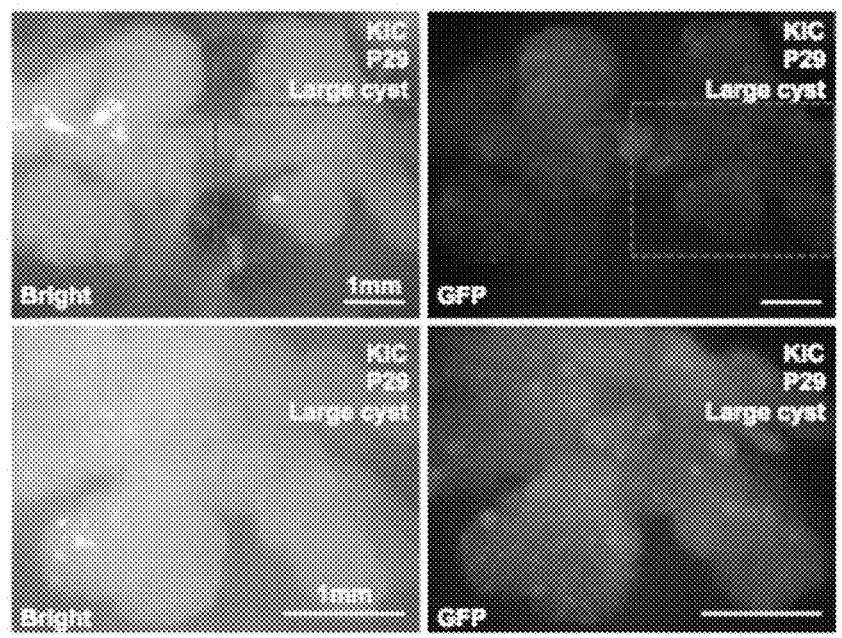
FIG. 14. Pancreatic lobes with edema in KIC mice invariably express high levels of Rgs16::GFP. Bright-field (BF) and green fluorescent (GFP) microscope images of a pancreatic lobe with a cyst and surrounding tissue from an Rgs16::GFP;KIC P29 mouse are shown. Expression initiates in acinar cells co-expressing high levels of CPA1 that apparently progress rapidly to neoplasia which maintains Rgs16::GFP but not CPA1 in duct-like structures on the margins of large cysts and throughout solid tumors. Area in the upper panels marks boundaries of lower panels (red dashed rectangle). Scale bar=1 mm.
Figure 15:
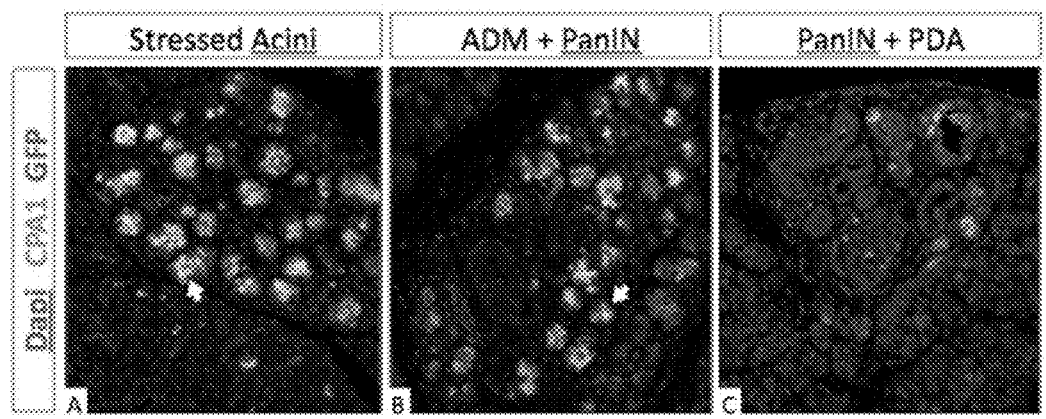
FIGS. 15A-C. Rgs16::GFP and CPA1 are co-expressed in edematous pancreatic lobes. Confocal images of immunofluorescence staining shows co-expression of Rgs16::GFP (red) and CPA1 (green) in acinar cells within well defined pancreatic lobes.

Rgs16::GFP is expressed in ADM, PanIN, and PDA. Pancreatic neoplasia secrete mucins and other polysaccharide-decorated proteins detected by Alcian Blue/Periodic Acid-Schiff (AB/PAS) staining PDA in KIC mice have intense Rgs16::GFP expression (FIG. 12) but little or no AB/PAS staining, whereas Rgs16::GFP is significantly lower in regions of neoplasia that are AB/PAS-positive (FIG. 3, inserts). High resolution confocal microscopy reveals Rgs16::GFP is not expressed in normal acinar cells, consistent with fluorescence microscopy of dissected pancreata (FIGS. 1-2). $Kras^{G12D}$-evoked ADM induces Sox9 expression, as previously reported (Kopp et al., 2012, Krah et al., 2015), and low Rgs16::GFP expression in most cells (FIG. 4). By contrast, Rgs16::GFP expression is significantly higher and co-expressed with Sox9 in duct-like PanIN lesions, consistent with the findings in FIG. 3. The marker of proliferation competent cells, Ki67, is co-expressed with Rgs16::GFP in many cells within PDA and PanIN but almost never in regions of ADM (FIG. 13). This pattern of high Rgs16::GFP expression in PanIN and PDA was confirmed by immunofluorescence with Muc1 and Ecad (FIG. 4). Exceptional conditions can induce intense Rgs16::GFP expression in acinar-like cells (FIG. 14) co-expressing high carboxypeptidase A1 (CPA1; FIGS. 15A-C). This pattern is observed in peripheral lobes with edema that sit beyond (proximal to) tumor nodules in KIC pancreata. These appear to be specialized responses where Rgs16 and CPA1 expression is secondary to PDA tumor growth.

Figure 5:
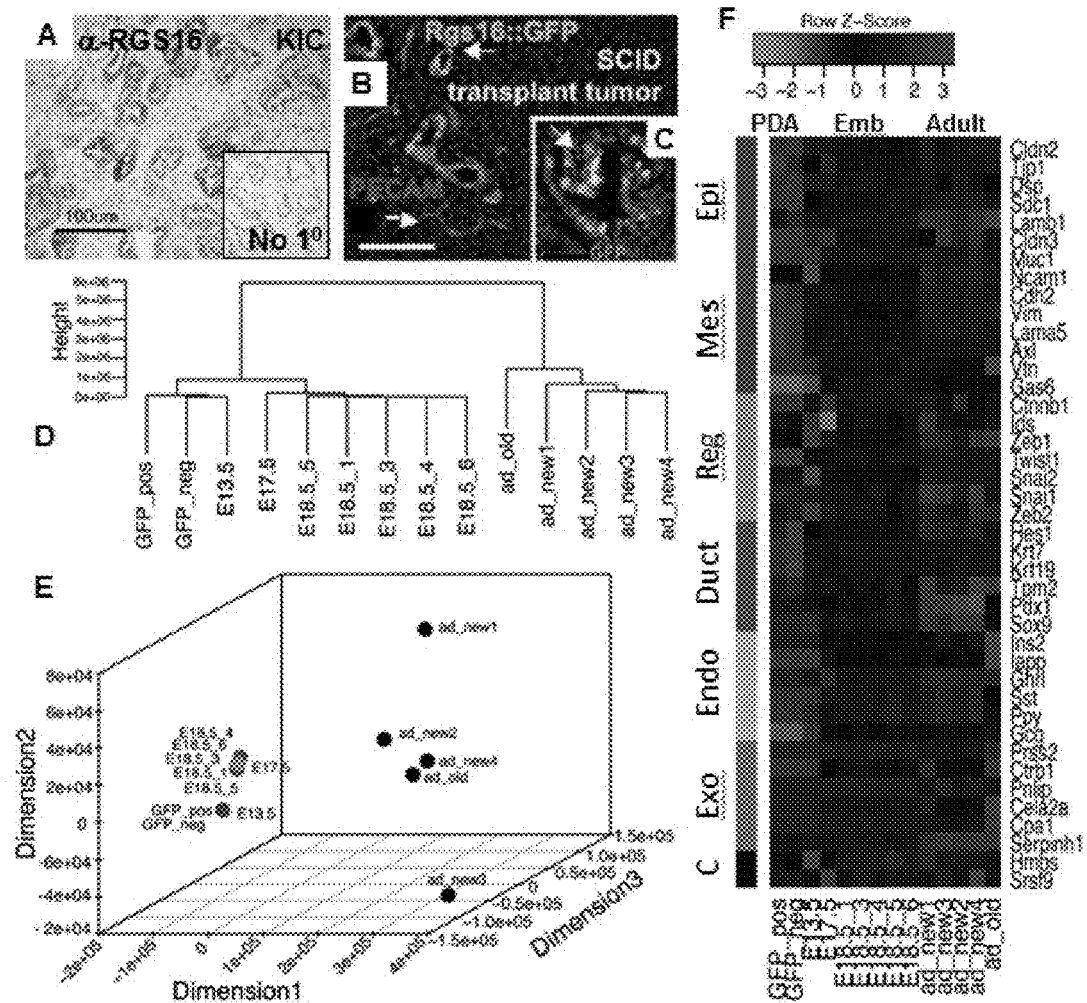
FIGS. 5A-F. Primary PDA cells express markers of pancreatic progenitor cells.
Figure 16:
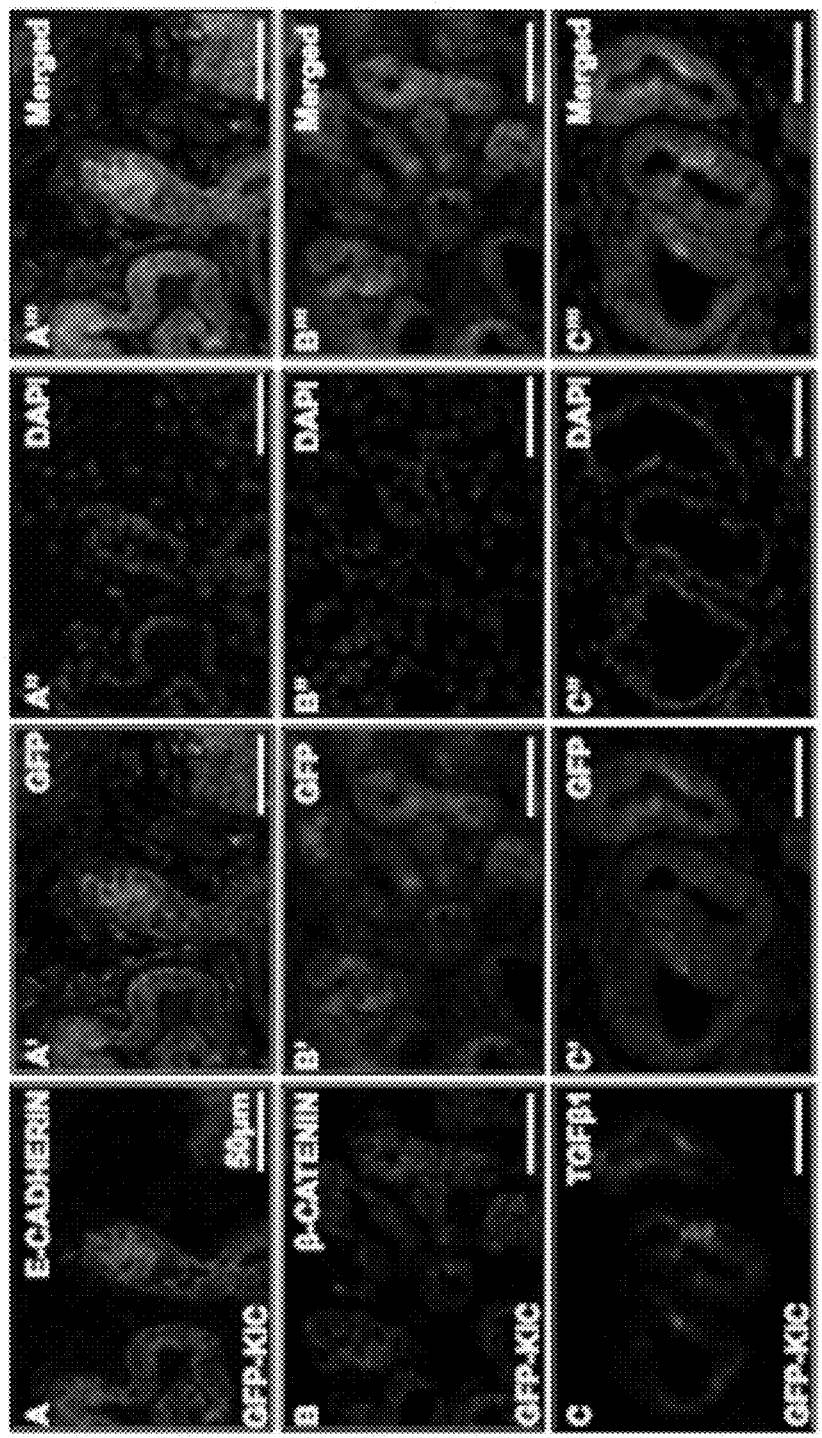
FIGS. 16A-C'''). RGS16::GFP is co-expressed with progenitor cell markers in KIC mouse pancreatic tumors. Co-expression of Rgs16::GFP with (FIG. 16A) E-CADHERIN, (FIG. 16B) β-CATENIN and (FIG. 16C) TGFβ1 in regions of ADM and epithelial plasticity. GFP (FIG. 16A', FIG. 16B', FIG. 16C') and DAPI (FIG. 16A'', FIG. 16B'', FIG. 16C'') staining are merged with that of progenitor cell markers at the last column (FIG. 16A''', FIG. 16B''', FIG. 16C'''). Scale bar=50 μm.

Rgs16::GFP is expressed in pancreatic ductal progenitor and PDA cells. KIC mice (6-8 weeks) and PDA primary cells in culture co-expressed Rgs16::GFP with markers of pancreatic progenitor cells and epithelial-mesenchymal transition (EMT), such as Sox9, Mud 1 and Ecad (FIG. 4, β-catenin; TGF-β. FIGS. 16A-C'''). Orthotopic transplantation of Rgs16::GFP-positive primary cells derived from PDA tumors at 6 weeks rapidly regenerated GFP-positive pancreatic cancer in duct-like structures in close proximity with vasculature in recipient NOD-SCID mice (FIG. 5B). By contrast, stroma of the non-transgenic host did not express GFP.

To gain more information about the gene expression profile of the KIC PDA cells, the inventors performed RNA-Seq analysis of the transcriptome, and found that PDA cells in primary culture are closely related to embryonic (E13.5) pancreas (FIGS. 5D-E). PDA cells and E13.5 progenitor cells of the ductal and endocrine lineages expressed Pdx-1 and Sox9 (FIG. 5F). Similarities in the transcriptomes diverged noticeably by E17.5 and E18.5, as pancreata begin to express more genes in maturing endocrine and exocrine cells, and fewer mesenchymal genes. The transcriptomes of PDA primary cells and normal adult pancreas are only distantly related; PDA cells do not express appreciable levels of markers of mature acinar or endocrine cell types.

In a survey of cancer-associated receptors and ligands in primary PDA cells in culture, the inventors noted that Axl is highly expressed, with modest expression of Gas6 (FIG. 5F, Table 1). Axl and Gas6 are highly expressed in many human primary PDA tumors (TCGA), containing both cancer and stromal cells. Axl was the most highly enriched receptor kinase expressed in PDA cells for which the inventors had inhibitors of active ligand maturation and receptor antagonists to test PDA initiation and progression. Furthermore, Axl is associated with EMT and drug resistance in carcinomas (Zhang et al., 2012, Byers et al., 2013). Therefore, the inventors sought to establish a rapid in vivo assay to assess the effect of clinical Axl inhibitors on PDA initiation and progression.

Two week in vivo assay: PanIN and PDA tumor growth suppressed at P29 by a combination of Axl-inhibitors, gemcitabine and Abraxane. The therapeutic screening strategy was to treat KIC pups between P15-P28 (when PanIN and PDA are in rapid expansion) with anticancer drugs, sacrifice mice at P29, and capture Rgs16::GFP intensity with a dissection fluorescence microscope. Images of the five brightest non-overlapping fields of Rgs16::GFP expression were then collected, representing the regions of greatest tumor burden (FIGS. 17A-C). This quantitative protocol represents a much more rapid approach (about 1% the time and effort) than traditional histology for a cohort of 20 adult mice.

Figure 17:
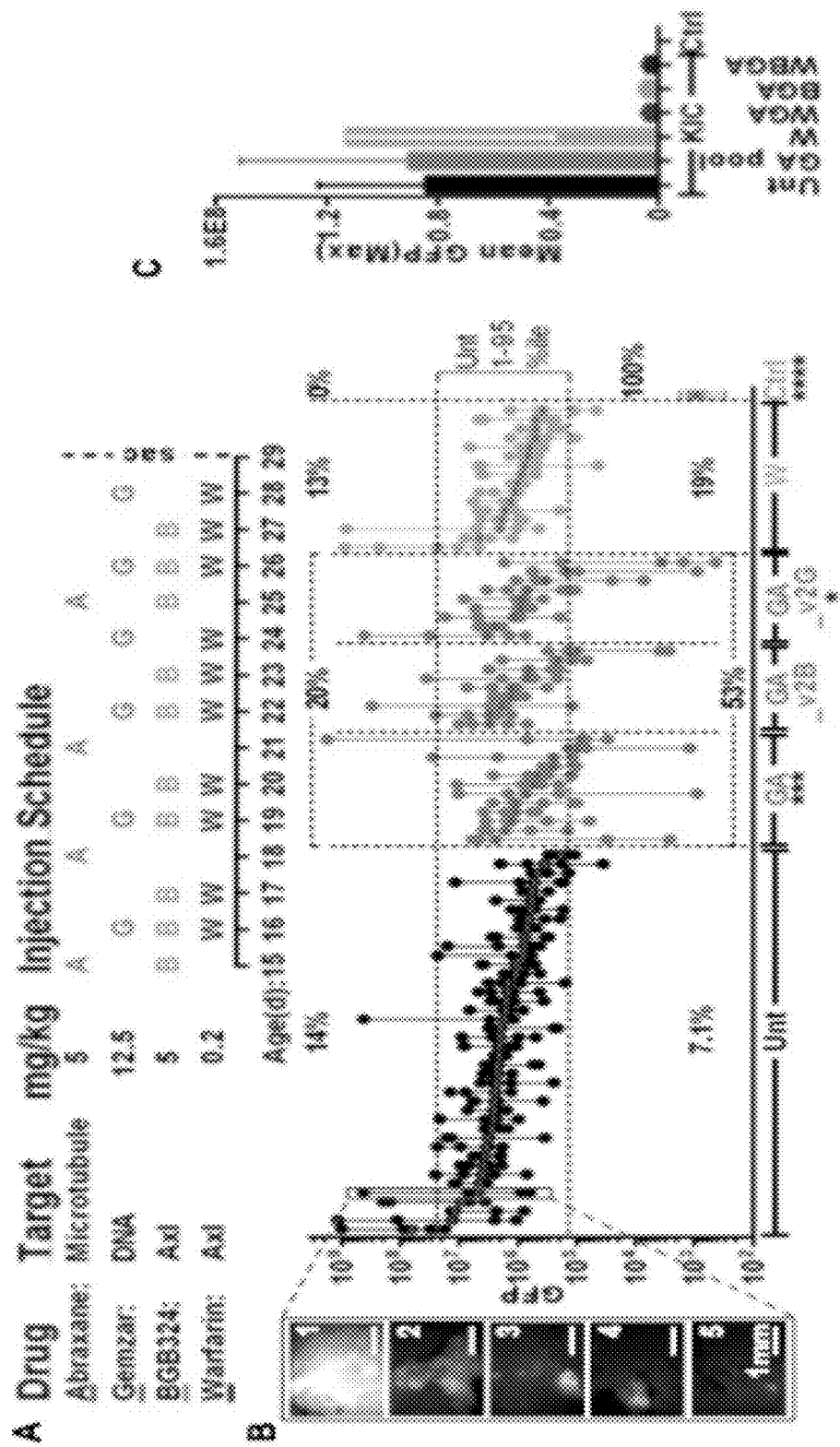
FIGS. 17A-C. PanIN initiation and median PDA tumor growth are suppressed by gemcitabine plus Abraxane in KIC mice at P29. Treatment schedule and dosage of each drug for in vivo assay in KIC mice from P15-P28 are shown. All animals were sacrificed at P29.
Figure 18:
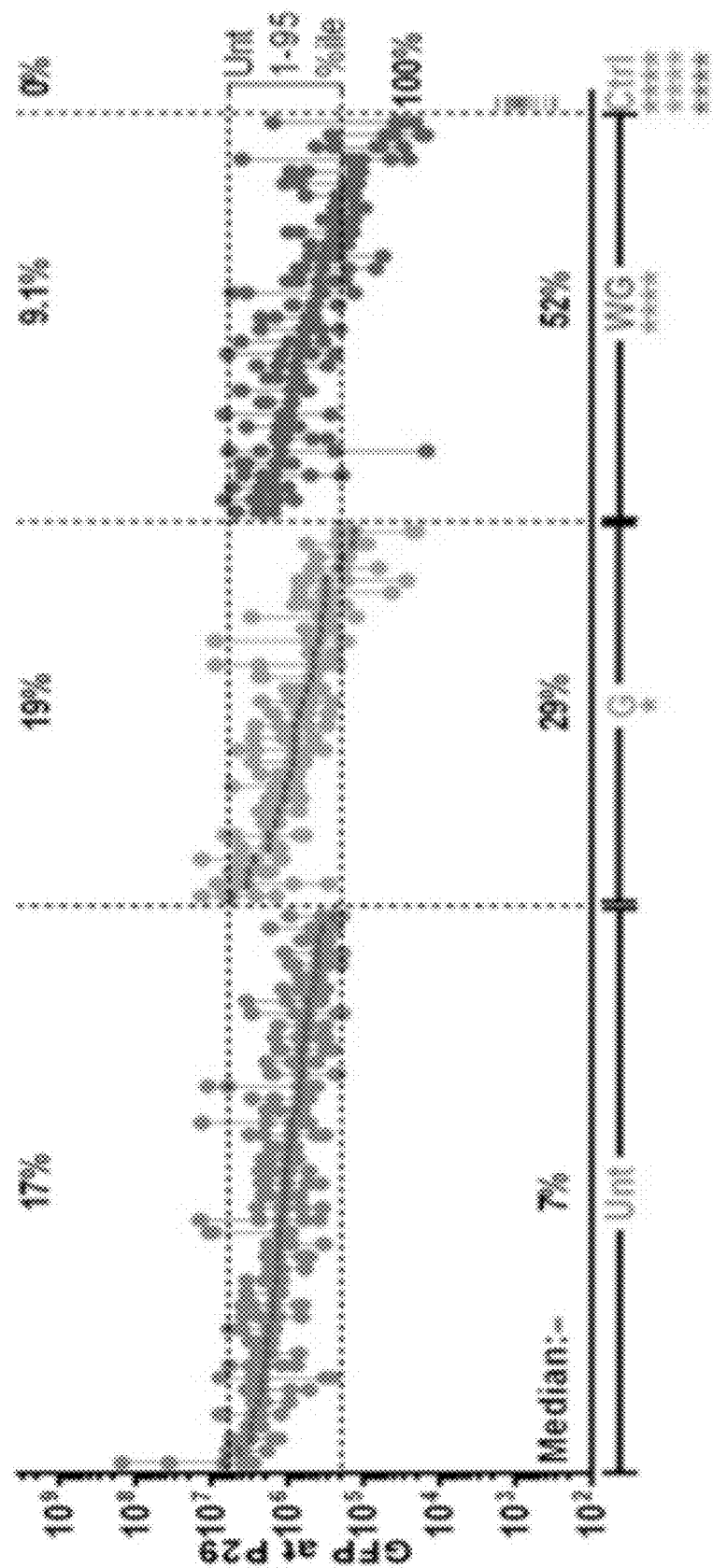
FIG. 18. Warfarin augments gemcitabine inhibition of PDA initiation and progression. GFP quantification of P29 Rgs16::GFP;KIC mouse pancreas shows reduction of GFP expression in gemcitabine (G, n=31) and gemcitabine with warfarin (WG, n=33) groups. Untreated (Unt) KIC mice (n=46) were collected from neighboring cages at the same time as the treatment groups. These mice were assayed a year after the mice in FIG. 4. Each column represents one pancreas, where each dot is a single micrograph depicting non-overlapping fields from $1^{st}$ to $5^{th}$ brightest in GFP expression (quantitated by ImageJ; statistics in FIG. 8). Normal Rgs16::GFP transgenic (Ctrl, n=24) mice have a single value each (grey lines at the far right). The $3^{rd}$ highest value as median for each mouse is represented with red horizontal lines, whereas median of Ctrl values is marked. Top and bottom horizontal dashed lines represent the $95^{th}$ and $1^{st}$ percentile values of all untreated KIC mice, respectively. For each group, percentages of mice with values above the $95^{th}$ percentile and below the $1^{st}$ percentile, respectively, are indicated. Statistical analyses were obtained from log(GFP) values via unpaired and two-tailed Student's t test. *, $p<0.05$; ****, $p<0.0001$. Asterisks match the color of the comparison group.
Figure 19:
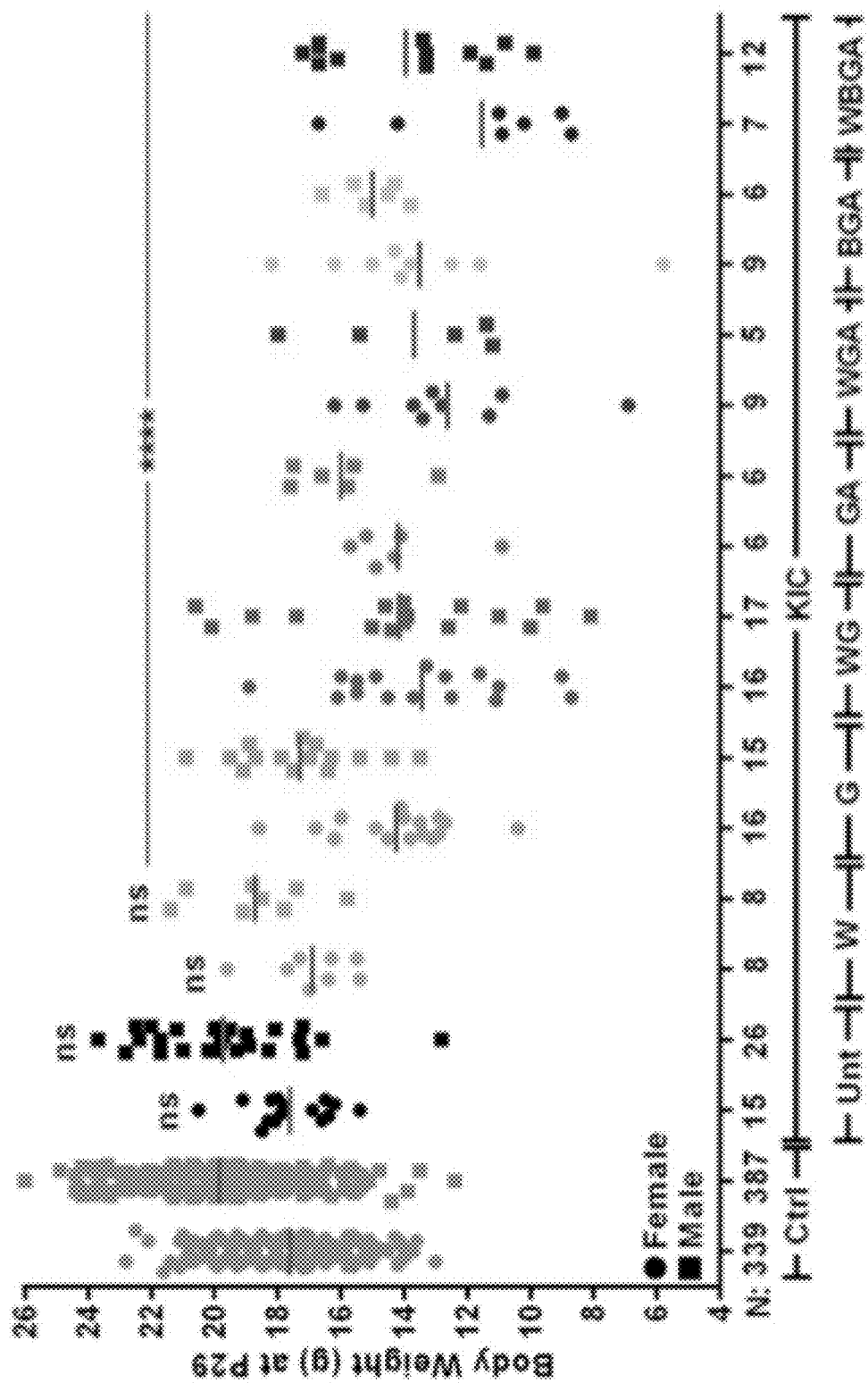
FIG. 19. Gemcitabine toxicity retards body weight gain in KIC weanling mice. Comparison of body weight of female (round) and male (square) non-KIC control (Ctrl, grey), and KIC untreated (Unt, black) or chemotherapy-treated KIC groups are shown. W, warfarin (purple); G, gemcitabine (bright green); WG, warfarin with gemcitabine (turquoise); GA, gemcitabine and Abraxane (green); WGA, warfarin with gemcitabine and Abraxane (blue); BGA, BGB324 with gemcitabine and Abraxane (bright blue); WBGA, warfarin and BGB324 with gemcitabine and Abraxane (dark blue). Significances are based on comparison of any KIC group to Ctrl via unpaired and two-tailed Student's t-test. ****, $p<0.0001$.
Figure 20:
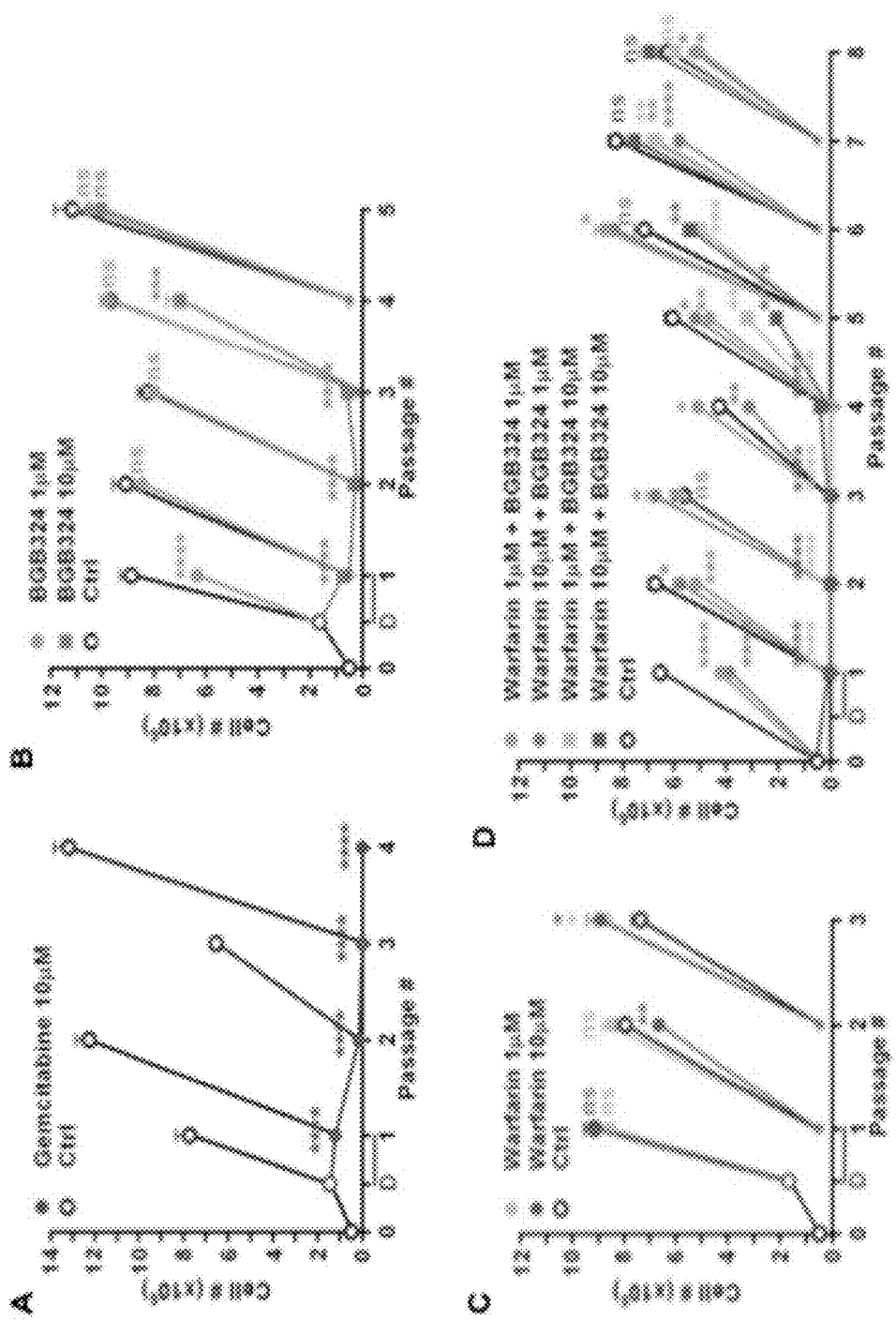
FIGS. 20A-D. BGB324 reversibly reduces cell viability and proliferation rate in primary PDA culture. Cell proliferation counts of primary PDA culture after 24 hr treatment with (FIG. 20A) gemcitabine (purple round)

To validate this in vivo screening approach, the inventors treated KIC mice with gemcitabine+Abraxane (GA), a current standard-of-care for PDA therapy (Von Hoff et al., 2013). GA therapy significantly reduced PanIN lesions throughout the pancreas (FIG. 17B; note the fields of low GFP expression in treated animals compared to untreated animals) and reduced average and median GFP expression (FIG. 6B). GA was more effective than gemcitabine alone at inhibiting PanIN initiation, relative to untreated controls (FIGS. 17A-18, statistical analysis FIGS. 7-8). Thus, this method detected that a standard-of-care drug treatment was able to impede tumor growth. However, toxic side effects inhibited growth of weanling mice (FIG. 19). Furthermore, while GA treatment reduced PanIN lesions, large PDA tumors emerged at the same frequency in untreated and GA treated mice (3 trials), consistent with its modest effects in humans (Becker et al., 2014). As in humans, tumor heterogeneity exists between mice, reflected in differences in Rgs16::GFP expression levels, histology, immunofluorescence and response to treatment in KIC mice. Heterogeneity also exists within each pancreas—some regions were apparently unaffected at P29 whereas other areas had ADM, PanIN, and/or small or large PDA tumors.

Figure 6:
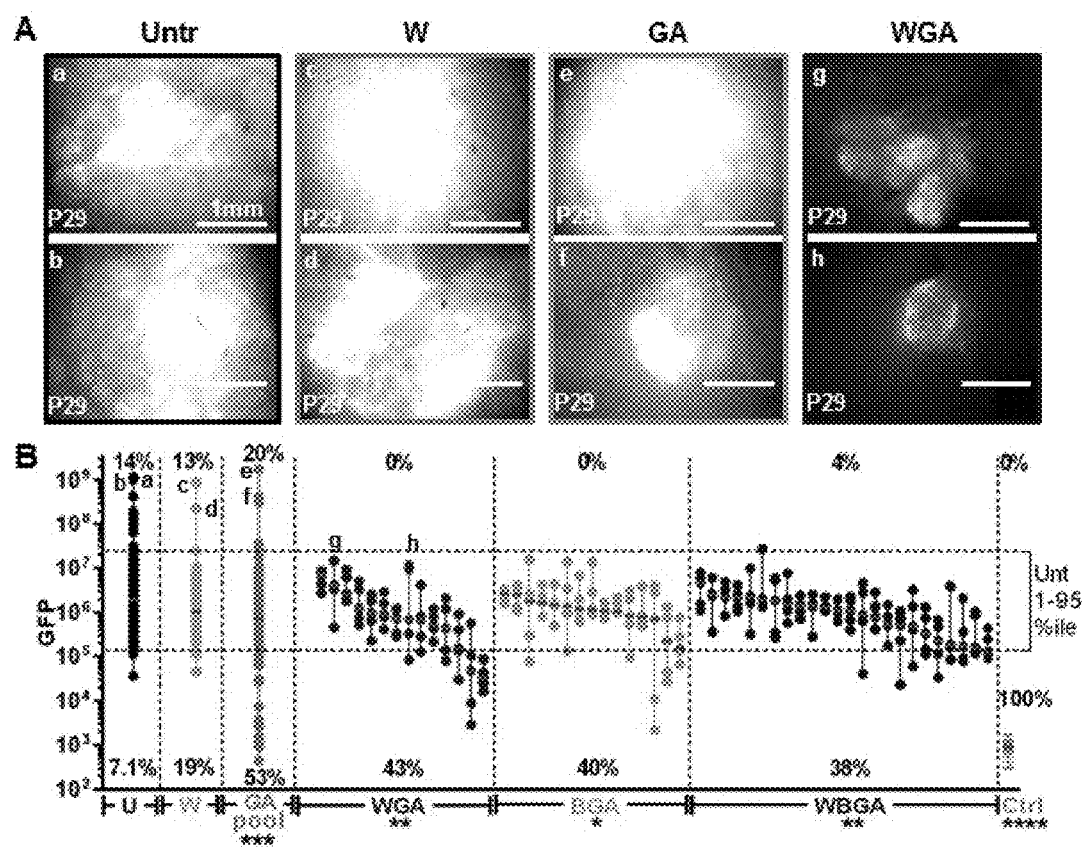
FIGS. 6A-B. Two week in vivo assay: PDA tumor growth and PanINs suppressed at P29 by Axl-inhibitors+Gemcitabine+Abraxane.
Figure 9:
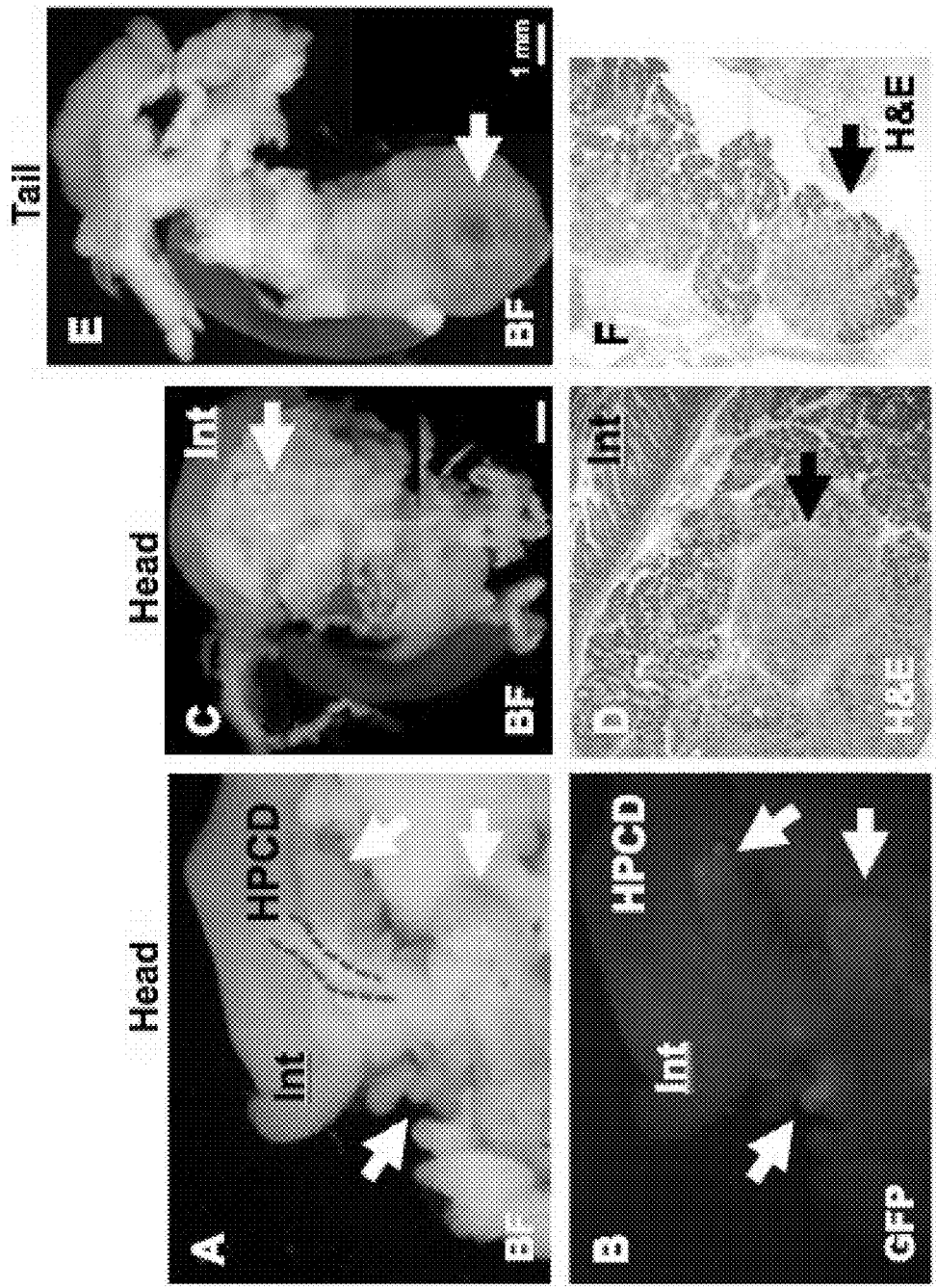
FIGS. 9A-F. PDA in KIC mouse pancreas but not hepatopancreatic duct.

To address whether blocking Axl signaling would improve GA effectiveness, the inventors tested two clinical Axl inhibitors, BGB324 (Ben-Batalla et al., 2013) and warfarin, in combination with GA in PDA primary cell culture and KIC Rgs16::GFP reporter mice. In PDA primary cell culture, high concentrations of gemcitabine killed cells, and BGB324 was cytostatic, but warfarin had no effect (FIGS. 20A-D). In KIC mice, warfarin had no effect by itself but when combined with gemcitabine+Abraxane (WGA), PanIN lesions were further reduced, and importantly, WGA significantly reduced the growth of large PDA tumors observed in untreated and GA treated mice (FIG. 6). Similar inhibitory effects were seen when GA was combined with BGB324 (BGA) or warfarin plus BGB324 (WBGA) (FIG. 6). Together, these data demonstrate that the screening strategy in KIC Rgs16::GFP mice is a relatively rapid means for identifying novel or repurposed drugs, as well as new drug combinations for treatment of Kras-dependent PDA.

TABLE 1

Axl and Gas6 mRNA in PDA, embryonic, and adult pancreas

| | Primary Target | | RNA-Seq (FPKM) | | | |
|---|---|---|---|---|---|---|
| | | | PDA | Pancreas | | |
| Therapeutic | Cell Type | Gen | culture | E13.5 | E18.5 | Adult |
| BGB324 | Cancer cell | Axl | 66.70 | 6.47 | 8.25 | 4.10 |
| Warfarin | Cancer cell & Stroma | Gas6 | 1.39 | 3.43 | 17.42 | 14.10 |

BGB324 inhibits Axl kinase;
warfarin inhibits gamma carboxylation of Gas6.
RNA-Seq samples: PDA culture, n = 2; E13.5, n = 1; E18.5, n = 5; adult, n = 5

Example 3

Discussion

The dismal survival rate of patients diagnosed with pancreatic cancer justifies an intense preclinical effort to identify novel PDA therapeutics. GEMMs have significant benefits for drug screening, including recapitulation of all major stages of PDA and the complex interplay between precancerous neoplasia, adenocarcinoma, immune components, and stromal elements (Cook et al., 2012). The inventors used the KIC model because it is currently the most aggressive GEMM of PDA available (Aguirre et al., 2003). KIC mice harbor the two earliest genetic mutations common to most PDA patients: oncogenic mutations in Kras, which confer GAP-resistance (e.g., $Kras^{G12D}$), and deletions of the tumor suppressor Cdkn2a. In the KIC GEMM, neoplasia initiate around two weeks of age and tumors (1-2 mm) develop in all untreated mice by P29. Furthermore, toxic and off-target drug effects inhibit growth of weanling mice and are easily measured as reduced body weight (FIGS. 20A-D). Although weanlings may be hypersensitive to toxic drugs, the screen allows a rapid assessment of in vivo drug efficacy and specificity in weanling pups at relatively modest cost.

To accelerate discovery of effective drugs that inhibit PDA in vivo, the inventors developed Rgs16::GFP as a sensitive reporter of PanIN and PDA initiation, progression, and tumor size by four weeks of age (P29) in KIC mice. Rgs16::GFP expression is $Kras^{G12D}$-dependent in KC and KIC mice. GFP is not expressed in IC mice (which do not develop neoplasia) and PDAs that develop in the GEMMs have no background fluorescence in the absence of the GFP transgene. Endogenous Rgs16 is not abundant in normal adult exocrine pancreas nor is it usually induced in dedifferentiating (injured) acinar cells early in the process. For example, Rgs16 is not induced in the pancreas (primarily acinar cells) of adult Ptf1a KO mice while CPA1 (an acinar cell marker) declines precipitously during the two-week progression of acinar cell de-differentiation (Krah et al., 2015). $Kras^{G12D}$ opposes Ptf1a maintenance of terminally differentiated pancreas and promotes acinar dedifferentiation in P29 KC and KIC mice (Krah et al., 2015). Widespread, high Rgs16::GFP expression in acinar-like cells (co-expressing high CPA1; FIGS. 15A-C) is sometimes observed in peripheral lobes with edema that sit beyond (proximal to) tumor nodules in KIC pancreata (FIG. 14). These are specialized responses where Rgs16 and CPA1 expression is secondary to PDA tumor growth. Tumors and/or calcified ductal stones may block the duct (analogous to partial pancreatic ligation (Xu et al., 2008)), and promote edema and signaling that stimulates this unusually intense co-expression of CPA1 and Rgs16. While Rgs16 expression persists, co-expression with CPA1 in these dedifferentiating pancreatic lobes is presumably transient, because these structures (and CPA1) are absent in PanIN and in older KIC mice with solid tumors occupying the entire transformed pancreas.

Figure 11:
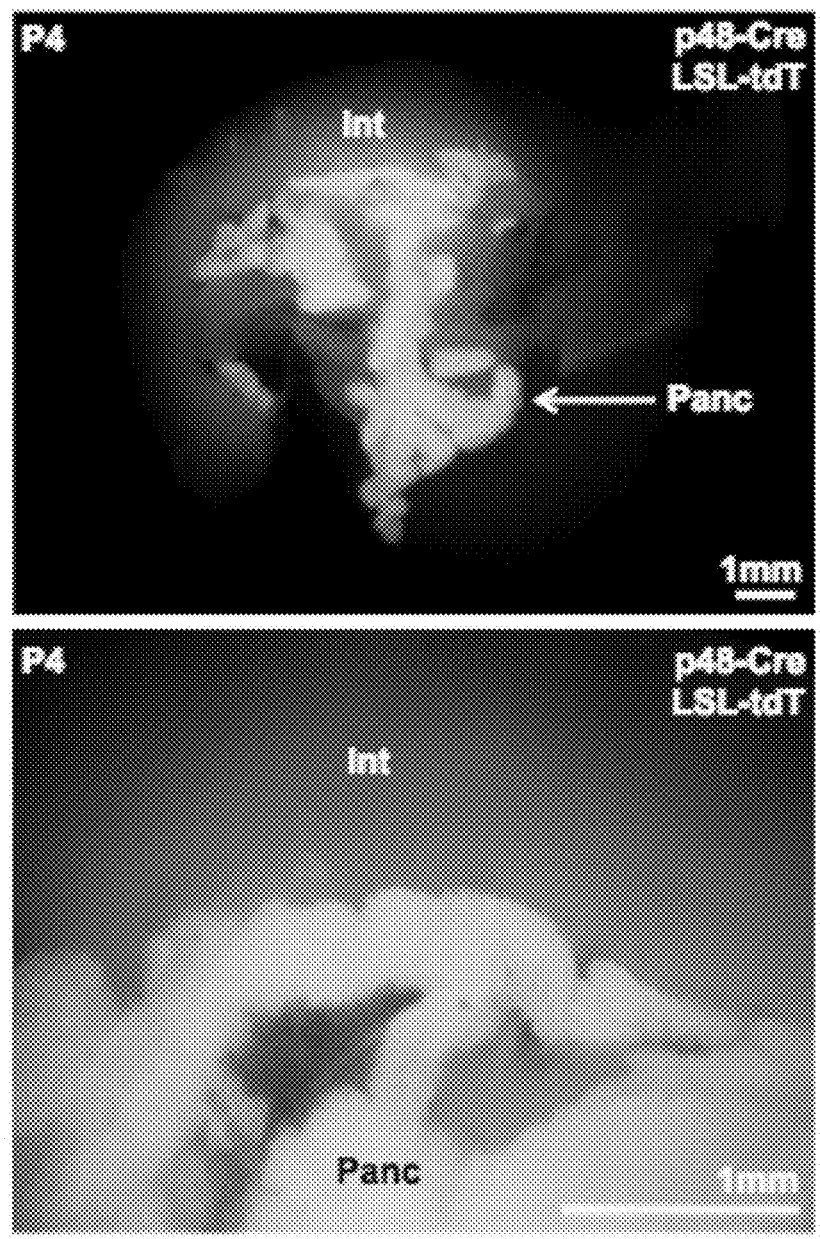
FIG. 11. p48::Cre drives LoxP-dependent recombination in the entire pancreas. p48::Cre expressing female mice were crossed with Lox-Stop-Lox-TdTomato (LSL-TdT) males to give rise to p48::Cre; LSL-TdT offspring. The p48 promoter drives CRE recombinase expression during early pancreas development. Therefore, all pancreatic cells are marked by TdT, should express $Kras^{G12D}$, and have Cdkn2a tumor suppressor deletion. Despite ubiquitous expression of $Kras^{G12D}$ and Cdkn2a deletion, only scattered lesions are observed in the pancreas of P15-P29 KIC mice. Each such lesion expresses Rgs16::GFP. Int, intestine; Panc, pancreas. Scale bar=1 mm.

An important point is that while all pancreatic cells in KIC mice express $Kras^{G12D}$ and have inactivated Cdkn2a (indeed, p48::Cre drives TdTomato expression throughout the pancreas; FIG. 11), Rgs16::GFP is absent at P15 except for expression in the earliest lesions, and then throughout tumor progression. Huang et al. (2014) showed that oncogenic Kras requires GTP loading for enhanced activity. Presumably Rgs16::GFP is marking the precise location, and perhaps the cells directly engaged in receptor-dependent activation of $Kras^{G12D}$ signaling. Thus, these in vivo reporter mice may help identify drugs which directly or indirectly inhibit $Kras^{G12D}$ activation during ADM, PanIN formation and PDA progression.

The inventors used Rgs16::GFP to evaluate novel PDA therapeutic combinations in a rapid (two week) in vivo screen. GFP intensity increases as a function of tumor burden in the pancreas (FIG. 2). Therefore, drugs and novel small molecules that inhibit PDA progression in vivo can be readily identified by their ability to reduce Rgs16::GFP fluorescence intensity in dissected pancreata (FIG. 6; FIGS. 17A-18). The inventors showed that a standard-of-care combination of gemcitabine+Abraxane (GA) reduced initiation of neoplasia in KIC;Rgs16::GFP reporter mice. However, GA did not significantly reduce growth of the largest pancreatic tumors, consistent with modest effects in prolonging survival in humans (Becker et al., 2014).

To identify additional genes that may be involved in PDA initiation and tumor growth, and therefore be potential targets for drug treatment, the inventors characterized the gene expression profile of primary PDA cells in culture by RNA-Seq. The transcription profile of PDA cells is most closely related to embryonic progenitors of ducts and islets, the same embryonic cell types that express Rgs16 (Villasenor et al., 2010). Rgs16::GFP is a marker of embryonic pancreatic stem cells at E9.0 in the pancreatic bud, and continues to be expressed in Sox9-positive duct cells and insulin-positive endocrine cells at E15.5 (Villasenor et al., 2010). Thus, following Rgs16 expression may lead to receptors and ligands important in stem cell function and cancer initiation.

Figure 21:
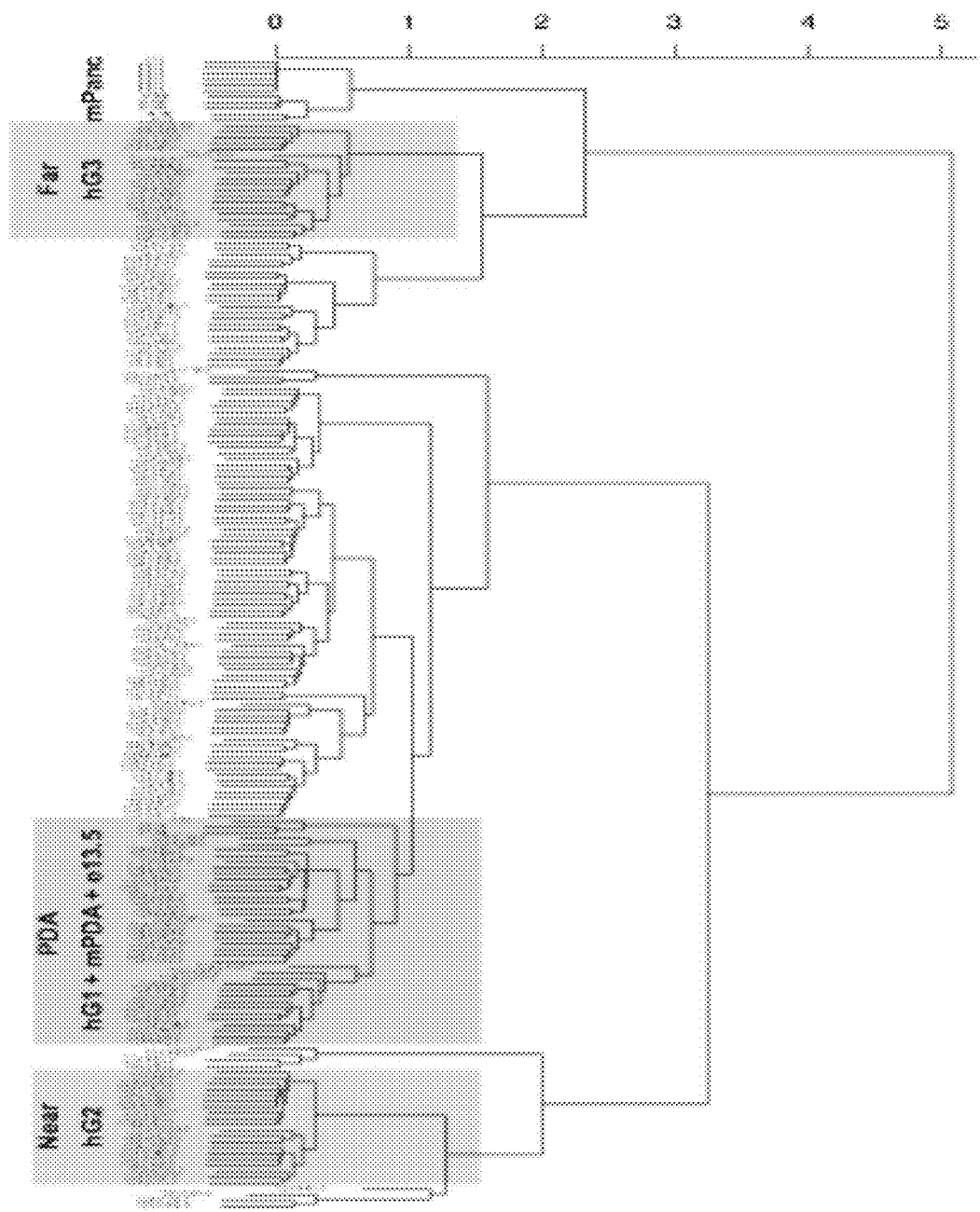
FIG. 21. Transcriptome relationships among human PDA and mouse PDA, embryonic and adult pancreas. Cluster dendrogram of RNA-Seq gene expression profiles from human primary tumor samples and mouse PDA culture and tissue samples. Human RNA-Seq data of mRNA from primary tumors was obtained from data generated by the TCGA Research Network://cancergenome.nih.gov/. The dendrogram was obtained by hierarchical clustering of pair-wise Pearson correlation distances between all samples using normalized gene expression values. Each branch represents a sample. Top axis is the height of the dendrogram representing the pairwise Pearson correlation distances. Three most important transcriptome clusters are highlighted. The purple highlighted cluster (PDA) contains human primary tumors (hG1) most similar to mouse embryonic pancreas (e13.5) and Rgs16::GFP positive and negative PDA primary cells (mPDA). The green highlighted cluster (Near) includes the next most related distinct human primary tumors (hG2) to PDA, whereas human primary tumors (hG3) most distantly related to PDA are shown in red highlighted cluster (Far). Transcriptomes of mouse late embryonic (1 e17.5 and 5 different e18.5 samples) and adult (5 different adult samples) pancreas samples are at the very top (mPanc). Labels of mouse PDA primary cells as well as embryonic and adult pancreas samples are red colored.
Figure 22:
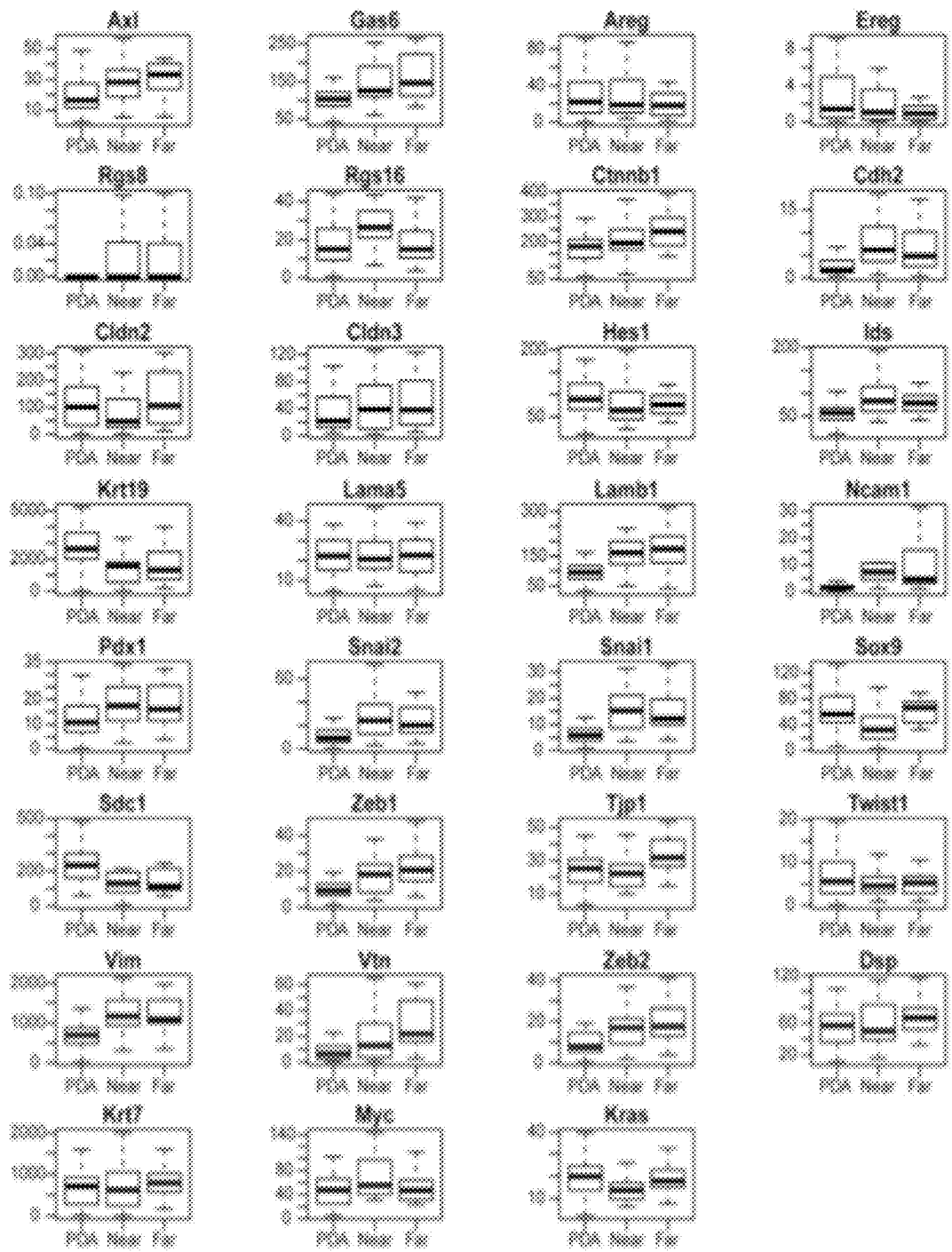
FIG. 22. mRNA expression profile of selected genes of human PDA clusters from FIG. 21. Comparison of genes important in PDA initiation and progression in the human PDA clusters (hG1, hG2, hG3) identified in FIG. 21. Boxplots show expression range for each gene in the three clusters of interest identified in the dendrogram from FIG. 21. Each gene expression range is depicted as a box containing the median value (horizontal thick black line) flanked by upper and lower quartiles (upper and lower box edge). The remaining 50% gene expression range outside the box is represented as dashed bars. hG1, human primary tumors most similar to mouse primary PDA cells within PDA cluster; Near, hG2 human primary tumors in the next most related distinct Near cluster; Far, hG3 human primary tumors in the most distantly related Far cluster from FIG. 21. Values are in FPKM.

The inventors found the tyrosine kinase receptor Axl was expressed 10-fold higher in primary PDA cells compared to normal embryonic (E13.5) and 16-fold higher than normal adult pancreas (FIG. 5F; Table 1), consistent with observations by others (Song et al., 2011). Axl and Rgs16 tend to be coordinately expressed in human PDA primary tumors (from analysis of co-expression of the human primary PDA samples characterized in FIGS. 21-22). High levels of Axl expression in advanced cancers from diverse cellular origins suggest that tumor cell-associated Axl may be a fundamental contributor to malignant progression (Holland et al., 2010). Indeed, the inventors' recent results support the notion that Axl signal transduction is required to maintain epithelial plasticity traits of aggressive pancreatic tumors comprising tumorigenicity, invasiveness, survival, drug sensitivity, and metastasis (Kirane et al., 2015). Additionally, Axl inhibition has been shown to block cell migration and reduce metastasis in breast cancer models (Gjerdrum et al., 2010; Paccez et al., 2013; Dunne et al., 2014; Paolino et al., 2014).

The inventors found that Gas6, the Axl ligand, is expressed in normal adult pancreas (and primary human PDA tumors; TCGA) but is 10-fold lower in PDA primary culture cells (Table 1). Warfarin inhibits post-translational gamma carboxylation of Gas6, which is necessary for its ability to activate Axl signaling (Lew et al., 2014). While warfarin by itself had no effect on PDA, warfarin combined with gemcitabine+Abraxane (WGA) had three important effects in KIC; Rgs16::GFP reporter mice. Compared to GA therapy alone, WGA further reduced the initiation of neoplasia, lowered median tumor size, and significantly reduced growth of the largest tumors. The inventors used low doses of WGA individually proven safe in humans. WGA retarded growth in weanling mice but this is attributable to gemcitabine and Abraxane. The inventors have recently shown that warfarin exerts its anti-cancer effects by inhibiting Gas6-mediated Axl activation in PDA tumor cells (Kirane et al., 2015). A selective Axl kinase inhibitor, BGB324, had similar effects on PDA initiation and growth when combined with GA (in preparation). Systemic Axl inhibition may also exert anti-tumor effects through host response-dependent mechanisms (Paolino et al., 2014, Kirane et al., 2015). The inventors screened a total of 53 mice with GA plus warfarin or BGB324. All mice survived treatment from P15 to P29, and about 40% had lower rates of neoplasia compared to the control mice the inventors analyzed.

Rgs16::GFP expression is essentially extinguished in pancreas of normal, euglycemic mice by P15 and completely absent by P28 (Villasenor et al., 2010). By contrast, Rgs16::GFP expression in the largest PDA tumors is about 1 million times brighter than control pancreas, or regions of KIC pancreas not yet affected by $Kras^{G12D}$ expression. Equally important for identification of the most effective PDA therapeutics, the median GFP expression in untreated mice is 1000-fold higher than non-GFP KIC mice, or Rgs16::GFP control mice lacking PDA. Warfarin+GA significantly retards PDA initiation and progression. Although this in vivo assay is sensitive and rapid, it is primarily a chemopreventive screen in young animals whereas PDA typically initiates in middle age and is diagnosed late in life. Therefore, the best drug candidates identified in this rapid in vivo assay should be validated in survival and tumor regression studies in adults. An early phase clinical trial is under consideration for low dose warfarin based on the combined findings the inventors report here, other preclinical studies (Brown, 1973; McCulloch and George, 1987; Schulman and Lindmarker, 2000; Kirane et al., 2015), and anecdotal observations in patients (Brown, 1973; McCulloch and George, 1987; Schulman and Lindmarker, 2000; Kirane et al., 2015). Although the inventors still find significant tumor progression in WGA-treated KIC mice, this might be caused by other receptors activating $Kras^{G12D}$. Further inhibition might be achieved by adding another inhibitor to the combination therapy.

In summary, the screening method described here reveals sensitivity to new drug regimens that inhibit $Kras^{G12D}$-mediated oncogenesis. These findings suggest that patients with successful resection of PDA and clear margins may benefit most from repurposed low-dose warfarin treatment in combination with gemcitabine chemotherapy. Future studies will test new drugs as they become available to help identify the most effective and targeted PDA therapeutics.

Example 4

Materials and Methods

Cell lines. Human pancreatic cancer cell lines AsPC-1, Panc-1, Capan-1, and Mia PaCa-2 were obtained from ATCC (Manassas, Va.), the murine cell line Pan02 was obtained from the DCTD tumor repository maintained by the NCI at Frederick. C5LM2 is a variant of Panc1 developed in the inventors' laboratory that was generated through 2 passages of growth in vivo and culture of liver metastases and has been characterized previously (Melisi et al., 2008). C5LM2, AsPC-1, Panc-1, Pan02, and Mia PaCa-2 lines were grown in DMEM, Capan-1 in was grown in IMDM, all cell lines were grown in a humidified atmosphere with 5% $CO_2$, at 37° C., and have been DNA fingerprinted for provenance using the Power-Plex 1.2 kit (Promega) and confirmed to be the same as the DNA fingerprint library maintained by ATCC and were confirmed to be free of *mycoplasma* (e-Myco kit, Boca Scientific).

Animal studies. All animals were housed in a pathogen-free facility with 24-hour access to food and water. Experiments were approved by, and conducted in accordance with, an IACUC approved protocol at UT Southwestern. LSL-$Kras^{G12D}$; $Cdkn2a^{lox/lox}$; $p48^{Cre}$ (KIC) mice were generated as previously described (Ostapoff et al., 2014). Four- to 6-week-old female NOD/SCID and C57/B16 mice were obtained from an on campus supplier. A total of $1\times10^6$ AsPc-1, Panc-1, Mia Paca2, Capan-1, C5LM2, Mia shLuc and Mia shAxl or $5\times10^5$ Pan02 cells, were injected orthotopically as described (Ostapoff et al., 2014). Mice with established tumors, as determined by sonography were randomized to receive normal drinking water or water containing 1 mg/L (~3.0 µM) warfarin for experiments in immunocompromised mice and 0.5 mg/L (~1.5 µM) in experiments in immunocompetent animals with or without gemcitabine 25 mg/kg twice weekly depending on experimental design. KIC mice were treated with warfarin 4 weeks starting at 3 weeks of age. For all experiments, warfarin containing water was replenished every 3 days. For Mia Paca2 tumor bearing mice, additional conditions of gemcitabine+/−10C9 (250 µg ip 2×/week) were conducted. Mice bearing Panc-1, Capan-1, C5LM2 and Mia Paca2 tumors were sacrificed after 6 weeks of therapy. AsPc-1 tumor bearing mice received 4 weeks of therapy and Pan02 tumor bearing mice 3 week of therapy. ShRNA lines were allowed to grow for 8-10 weeks. For all therapy experiments primary tumor burden was established by weighing pancreas and tumor en bloc. Metastatic incidence was determined by visual inspection of the liver and abdominal cavity and confirmed by H&E of liver sections. Tissues were fixed in 10% formalin or snap-frozen in liquid nitrogen for further studies. C5LM2 cells were injected intrasplenically to establish liver metastases, tumors were allowed to grow for 24 weeks and mice were randomized to receive either normal drinking water or warfarin (1 mg/L) starting 48 hours prior or 48 hours after tumor cell injection. Liver tumor burden was determined by liver weight.

Histology and tissue analysis. Formalin-fixed tissues were embedded in paraffin and cut in 6 µm sections. Sections were evaluated by H&E and immunohistochemical analysis using antibodies specific for vimentin (Phosphosolutions), endomucin, E-cadherin, (Santa Cruz), phospho-histone H3 (Upstate), cleaved caspase-3 (Cell Signaling). Negative controls included omission of primary antibody and immunofluorescence evaluation was conducted as described (Ostapoff et al., 2014). Necrotic area was determined by quantification of percent viable tumor area on low magnification of tumor sections by H&E.

Statistics. Data were analyzed using GraphPad software (GraphPad Prism version 4.00 for Windows; GraphPad Software; world-wide-web at graphpad.com). Results are expressed as mean±s.e.m. or s.d. Data were analyzed by t-test or ANOVA and results are considered significant at $p<0.05$.

Production of stable shRNA-mediated knockdown of Axl. Phoenix A retroviral packaging cells (Dr. Gary Nolan, Stanford University, CA) were cultured in DMEM containing 10% FBS, 100 U/mL of penicillin and 100 µg/mL of streptomycin (Sigma-Aldrich). For shRNA studies, infected cells (Mia PaCa-2-shLuc and -shAxl) were established as previously described (Gjerdrum et al., 2010). Briefly, Phoenix A cells were transfected using the calcium phosphate method with retroviral vectors expressing shRNA-Luc (L108-RRI-Red/L087-Luc-shRNA) or shRNA-Axl (L391-RRI-CherryNLS-Axl-shRNA). Approximately 30 h after transfection, the medium was changed to growth medium. Infectious supernatant was collected 48 h after transfection. Target cells were exposed to virus-containing supernatant supplemented with 5 μg/mL protamine sulfate overnight. Infected cells were selected with 1 μg/mL puromycin, for 24 hours and recovered. Infected cells were further purified based on RFP expression using FACS-Aria live cell sorter (BD Biosciences). shRNAs were expressed from a modified human U6 promoter in the LTR of the retroviral vectors RRI-Red/L087 (GenBank: EU424173) or RRI-CherryNLS. The following sequences were used (hairpin in small letters):

```
shAxl2:
                                    (SEQ ID NO: 7)
GACATCCTCTTTCTCCTGCGAAGCCCATctggtcATGGGCTTCGCAGGAGA

AAGAGGATGTC;

shLuc:
                                    (SEQ ID NO: 8)
GATTATGTCCGGTTATGTAAACAATCCGGctggtcCCGGATTGTTTACATA

ACCGGACATAATC.
```

Final retroviral vectors carrying shAx12 hairpin or shLuc hairpin are named L391-RRI-CherryNLS-Axl-shRNA (shAxl) and L108-RRI-Red-Luc-shRNA (shLuc) respectively. Knockdown was confirmed by flow cytometery (see FIGS. 28A-D).

Expression studies. For Western blot analysis, cell lysates were produced using MPER (Pierce) with added protease and phosphatase inhibitors (Pierce) and protein concentration was determined by BCA assay (Pierce). Immunodetection was conducted by electrophoretic transfer of SDS-PAGE separated proteins to PVDF membranes. Antibodies used for Western blot analysis included p-Akt, total Akt, p-ERK, cleaved caspase 3, cleaved Parp (Cell Signaling) and β-Actin (R&D Systems).

For PCR analysis, RNA was prepared using TRIzol (Invitrogen) per manufacturer instructions and concentration was determined by spectrophotometry. The cDNA used for subsequent for PCR was made using iScript (Bio-Rad Laboratories) and Choice DNA Taq polymerase (Denville Scientific). The expression of Axl, Gas6, Twist, Snail, and Zeb1 was analyzed by quantitative real-time PCR using β-actin as an internal reference gene. Each reaction was conducted in triplicate with RNA harvested from 3 independent cell cultures. The comparative Ct method was used to compute relative expression values (Karlen et al., 2007).

Signaling and functional assays. Cells were grown to confluence in 10 mm dishes or 4 well chamber slides and treated overnight with low serum (1-2%) media+/−warfarin (2 μM) or 10C9 (1.1 μM, 168 μg/ml) overnight. Cells were subsequently analyzed by western blot or immunocytochemsitry (ICC).

Anchorage-independent growth assays were performed by coating 12 well plates with 0.5-0.75% agar. Cells were resuspended in 0.375% agar with or without 2 μM warfarin. Fresh media and drug were added twice weekly and colonies were measured by light microscopy at 2 weeks; assays were performed in quadruplicate.

Migration assays were performed by growing cells in 6 well plates, at confluence a 20 μl pipette tip was used to scratch in a crossed fashion in each well. Cells were then incubated in 2% serum containing media with or without 2 μM warfarin. Cells were measured at 0, 12, 16, and 24 hours and % closure was calculated compared to time 0.

For spheroid assays, matrigel was coated on 18×18 mm glass cover-slides in a 35 mm culture dish, using Reduced Growth Factor Matrigel (BD Bioscience) as described previously (Gjerdrum et al., 2010; Lee et al., 2007). Cells were seeded on top (30,000 cells per gel) and overlaid with growth medium containing 1% Reduced Growth Factor Matrigel, 2% serum and indicated drugs or control solvent. Cultures were re-fed every 3$^{rd}$ day and maintained for 5-8 days in culture before imaging. Quantitative analysis of 3D organotypic structures was performed using Image J analysis software. Total number of established structures and the ability of established structures to migrate into the BM (Total area) were quantified and compared.

Cytotoxicity and augmentation of chemotherapy response was measured by MTS assays conducted in 96-well plates; cells were plated on day 0 and drug was added on day 1 in 4-fold dilutions. Maximum concentration of 2,000 nmol/L for gemcitabine was used with or without the addition of a constant concentration of 2 μM warfarin or 1.1 μM 10C9. Relative cell number was determined by adding MTS (Promega; final concentration 333 mg/mL), incubating for 1 to 3 hours at 37° C., and reading absorbance. Drug sensitivity curves and $IC_{50}$s were calculated using in-house software.

In vitro epithelial to mesenchymal transition assays. In vitro, mesenchymal transition was induced by incubating cells on chamber slides coated with collagen and adding TGF-β (20 ng/ml) to media with 5% serum for 48 hours. Media was then replaced with 1% serum and fresh TGF-β with or without warfarin (2 μM) for an additional 48 hours. Cells were the evaluated by immunocytochemistry by fixing in acetone, permeabilizing with 0.5% Brij, and incubating overnight with primary antibody: Axl, p-Axl, (R&D Systems); Vimentin (phosphoSolutions); Zeb1, E-Cadherin, and β-Catenin (Santa Cruz). The effect of Gas6 signaling on EMT was evaluated by seeding cells overnight and incubating with Gas6 (100 ng/ml) with or without warfarin for 48 hours. Cells were evaluated by ICC as described.

Example 5

Results

The inventors evaluated the efficacy of low dose warfarin (0.5-1 mg/L of drinking water) as a single agent in five murine models of pancreatic ductal adenocarcinoma (PDA) (FIGS. 23A-B). Low dose warfarin therapy was administered when animals had established intrapancreatic tumors as measured by sonography. Treatment with low dose warfarin reduced primary tumor growth in in a syngenic model (Pan02, FIG. 23A), a spontaneous genetic PDA model (KIC, FIG. 23A) but had little effect on the growth of human tumor xenografts (Panc1, AsPC1, Capan-1, FIG. 23A). Importantly, low dose warfarin consistently and potently inhibited metastatic burden (FIG. 23B and Table 2) in four of the five PDA models. Expression analysis revealed that warfarin-sensitive tumors expressed detectable levels of Axl, while the nonresponsive Capan-1 tumors did not (FIGS. 23C-E). Furthermore, Gas6 was expressed at detectable levels in most PDA cell lines (data not shown and Song et al., 2011), indicative of autocrine Axl activation. To evaluate the effects of selective Axl inhibition on PDA, the inventors used a stable retroviral shRNA approach. Axl knockdown completely suppressed the growth of orthotopic Mia PaCa-2 tumors (FIG. 23F). Extended in vivo growth of shAxl Mia Paca-2 cells in an independent experiment resulted in 4 of 7 mice developing tumors. These tumors were subsequently found to express Axl (FIGS. 27A-D). To validate tumor-selective inhibition of Axl activity in the treatment setting, the inventors developed a function-blocking human-specific anti-Axl monoclonal antibody, 10C9 (FIGS. 28A-D). Treatment of established orthotopic Mia PaCa-2 tumors with 10C9 blunted primary tumor growth and potently suppressed metastases (FIG. 23G). These results support the notion that low dose warfarin inhibits pancreatic tumor progression in manner dependent on tumor cell Axl expression.

Figure 29:
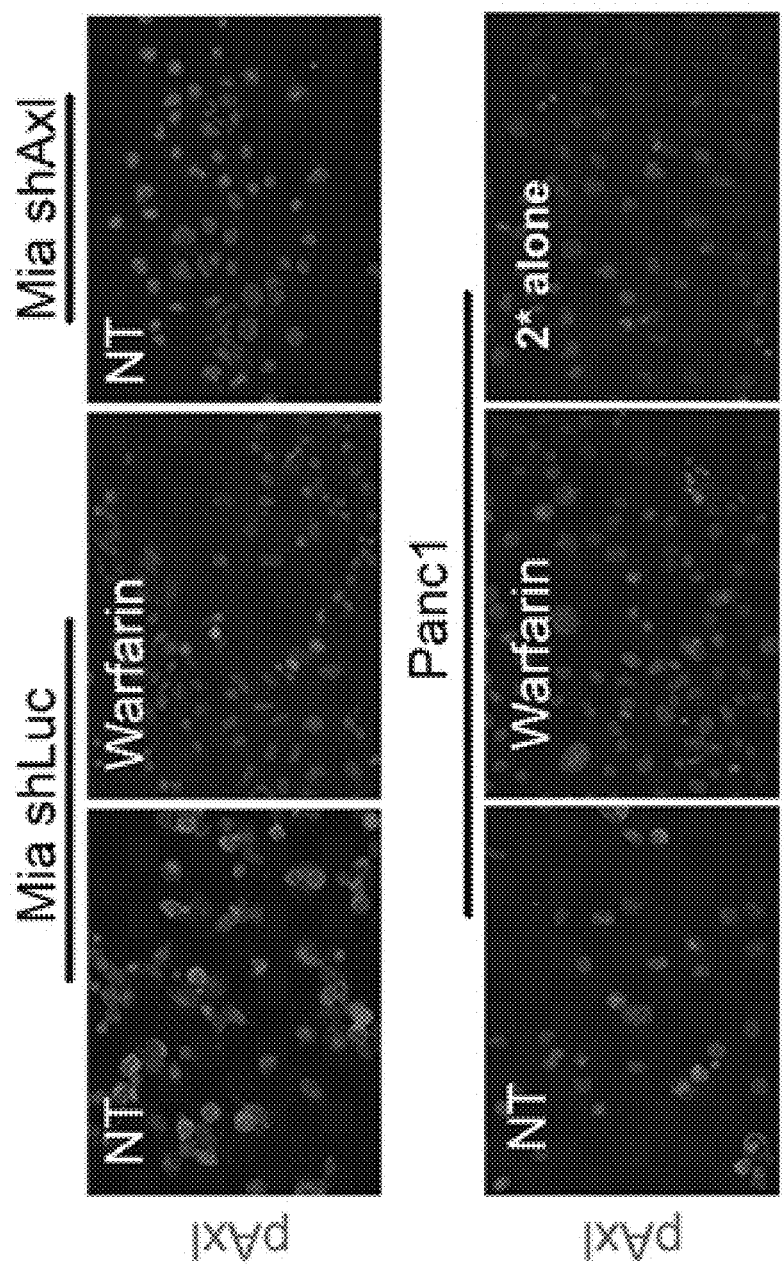
FIG. 29. Warfarin inhibits autocrine activation of Axl in pancreatic tumor cells. MiaPaca2 cells stably expressing shRNA specific for luciferase (shLuc) or Axl (shAxl) or Panc1 cells were incubated overnight in media containing 2% serum with no additions (NT) or with warfarin (2 μM). The level of phosphorylated Axl (pAxl) was determined by immunocytochemistry. Controls for specificity include Mia shAxl cells which did not show any pAxl reactivity and Panc1 cells stained with secondary alone (2* alone).

To determine the effect of warfarin on Gas6-induced Axl signaling in PDA, the inventors evaluated phosphorylated Axl (pAxl) and downstream signaling via the PI3K-Akt signaling pathway (Sawabu et al., 2007). Warfarin prevented γ-carboxylation of Gas6 in vitro (FIG. 24A) inhibited basal pAxl levels in Panc-1 cells, an effect that was rescued by addition of exogenous vitamin K (FIG. 24B). The effect of warfarin on pAxl was validated in Mia PaCa-2 and Panc-1 immunocytochemistry (FIG. 29). Further warfarin or BGB324, a specific inhibitor of Axl tyrosine kinase activity (Holland et al., 2010) inhibited phosphorylation of Axl in Panc-1 cells (FIG. 24C). Consistent with these results, treatment of Panc-1 cells in vitro with 10C9 resulted in decreased Axl and p-Axl levels (FIGS. 28C-D). Further, warfarin inhibited Gas6-induced activation of AKT in Panc1 cells in vitro (FIG. 24D). Additionally, the effect of low dose warfarin treatment on Panc-1 xenografts was consistent with the effects on Axl signaling in vitro. Warfarin treatment substantially suppressed the level of pAxl and pAkt in Panc-1 tumors (FIG. 24E), decreased expression of phosphorylated histone H3, a marker of proliferation, and elevated cleaved caspase 3, and tumor necrosis (FIGS. 30A-D) and increased the level of cleaved Parp (FIG. 2E). Low dose warfarin also reduced intratumoral microvessel density (FIG. 30D) consistent with the reported pro-angiogenic activity of Axl (Ruan and Kazlauskas, 2012).

Axl has been associated with enhanced tumor cell migration and metastatic invasiveness (Gjerdum et al., 2010). Warfarin reduced basal and Gas6-induced cell migration (scratch assay) in an Axl-dependent manner (FIG. 24F). Furthermore, tumor cell sphere formation and invasiveness in 3D culture was inhibited by warfarin and shRNA knockdown of Axl in Mia PaCa-2 cells (FIGS. 25A-C). Warfarin also inhibited anchorage independent growth of Axl-expressing cells (FIG. 25D) and inhibited liver colonization of Panc-1 cells after intrasplenic injection regardless of whether warfarin was administered pre or post (48 hrs) tumor cell injection (FIG. 25E).

The inventors also evaluated whether Axl inhibition with warfarin or 10C9 augmented the efficacy of gemcitabine, the frontline therapy for pancreatic cancer. Warfarin treatment had no effect on the $IC_{50}$ of gemcitabine on Axl-negative cells lines (Capan-1 and Mia PaCa-2 shAxl) in vitro. However, low dose warfarin potentiated the anti-proliferative effect of gemcitabine, reducing the $IC_{50}$ 8.4 and 211 fold in AsPC-1 and Panc-1 cells, respectively. Warfarin also lowered the gemcitabine $IC_{50}$ in Mia PaCa-2 and Pan02 cells (Table 3). In vivo blockade of Axl activation with low dose warfarin or 10C9 augmented gemcitabine reduction of primary tumor growth and dramatically improved metastatic control (FIGS. 25F-G).

Figure 32A:
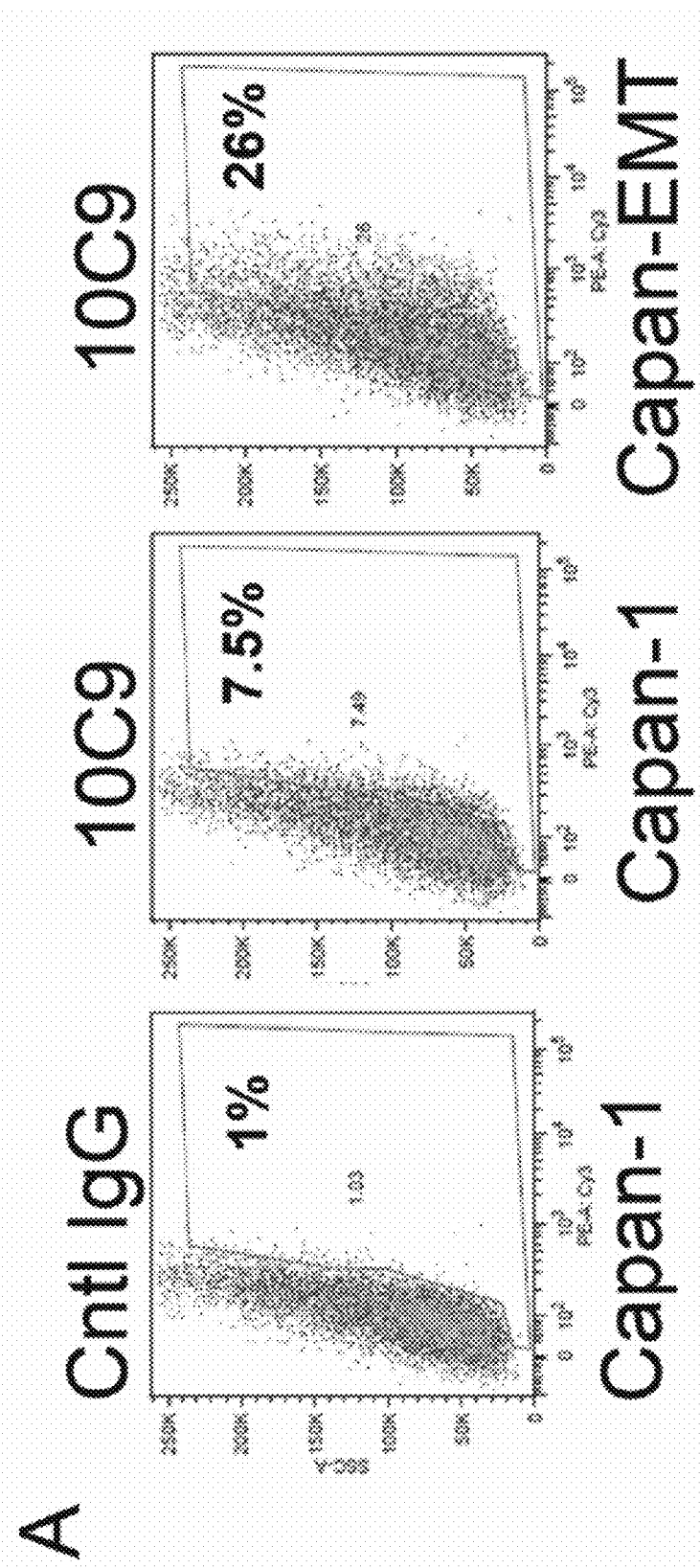

Metastasis and drug resistance are linked to induction of epithelial-to-mesenchymal transition (EMT) gene programs in pancreatic cancer (Rhim et al., 2012). Axl expression is elevated in tumor cells by EMT and correlated with mesenchymal marker proteins such as vimentin (Gjerdrum et al., 2010). Mia PaCa-2 cells display an EMT-like phenotype under basal conditions (Arumugam et al., 2009). The inventors found that treatment of Mia PaCa-2 cells with warfarin for 48 hrs in vitro reduced pAxl levels, surface Axl expression and the mesenchymal markers Zeb1 and vimentin, while elevating the expression of the epithelial marker E-cadherin (FIGS. 31A-B). Treatment of Panc-1 cells in vitro with TGFβ and collagen I, conditions that induce EMT, enhanced Axl expression and activation, an effect that was blocked by addition of warfarin (FIG. 26A). Consistent with these results, Zeb1 and nuclear β-catenin levels, another mesenchymal marker, were significantly reduced by warfarin indicative of phenotypic reversal (FIG. 26A). Furthermore, Gas6 addition to Panc1 cells in culture increased the expression of vimentin and Zeb1, an effect that was blocked by 10C9 (FIG. 26B). Additionally, the inventors identified that exposure to TGFβ and collagen induced Axl expression in Capan-1 cells (Capan-EMT), which correlated with increased expression of transcription factors (Zeb1, Snail, Twist) that drive EMT. The EMT-dependent induction of Axl in Capan-1 established autocrine activation via endogenous Gas6. Correspondingly, the Capan-EMT cells were sensitive to treatment with warfarin leading to decreased Axl expression, upregulated E-cadherin and increased cleaved caspase-3 levels (FIGS. 32A-C). Finally, the inventors found that low dose warfarin treatment of PDA Panc1 xenografts reduced expression of vimentin and elevated the expression of E-cadherin, results consistent with the observed EMT reversal in vitro (FIG. 26C).

To test tumor suppressor activity of Rgs8 and Rgs16 (Gi/Gq-GAPs), a Rgs8-Rgs16 double knock-out mice were made and introduced these mutant alleles into KC mice. The transgenic KC-R (i.e., LSL-Kras$^{G12D}$;p48$^{Cre}$; Rgs8$^{-/-}$16$^{-/-}$ (DKO)) mice die before 4 months of age because they can not maintain energy homeostasis as Rgs8 and Rgs16 are required in the liver to conserve energy utilization in malnourished mice. Once the KC-R mice develop PDA, they rapidly progress to aggressive metastasis to liver and lung.

The pancreas of these mice fails more rapidly than KC, and PDA typically develops about 6-10 months of age. The unique feature of KC-R mice is that once they develop PDA, the tumors rapidly progress to aggressive metastasis to liver and lung (FIGS. 33A-C).

TABLE 2

Metastatic Events in Preclinical Models of PDS

| Model | n | Mean | SD | Range |
|---|---|---|---|---|
| KIC | 10 | 1.6 | 1.9 | 0-5 |
| Pan02 | 4 | 22 | 11.5 | 9-37 |
| Panc1 | 8 | 2 | 1.5 | 0-4 |
| AsPC1 | 8 | 2.1 | 1.5 | 0-5 |
| Capan-1 | 10 | 0.6 | 0.84 | 0-2 |
| MIA PaCa-2 | 7 | 4.3 | 2.06 | 2-8 |
| C5LM2 | 9 | 3.6 | 2.4 | 0-7 |

NOTE:
Metastatic burden in control-treated animals in multiple preclinical models of PDA. The number animals (n), Mean +/− standard deviation (SD) and range of visible liver metastases are shown.

TABLE 3

Warfarin Enhances Gemcitabine Activity in an Axl-Dependent Manner

| Cell Line | Gemcitabine (nmol/L) | | Gemcitabine (nmol/L) + Warfarin (2 μM) | | Fold Reduction |
|---|---|---|---|---|---|
| | median | SD | median | SD | |
| Pan02 | 76.5 | 26 | 53 | 16 | 1.4 |
| Panc1 | 17.05 | 14 | 0.0805 | 0.012 | 213 |
| ASPC | 16 | 2.8 | 1.9 | 0.28 | 8.4 |

TABLE 3-continued

Warfarin Enhances Gemcitabine Activity in an Axl-Dependent Manner

| Cell Line | Gemcitabine (nmol/L) | | Gemcitabine (nmol/L) + Warfarin (2 µM) | | Fold Reduction |
|---|---|---|---|---|---|
| | median | SD | median | SD | |
| MiaPaca | 14.5 | 2.1 | 13.2 | 5.5 | 1.04 |
| MiaShAxl | 21 | 2.8 | 30.5 | 2.1 | 0 |
| Capan | 6.87 | 2.2 | 9.35 | 0.73 | 0 |

NOTE:
Cell growth assays were performed in a 96-well format for 5 days (n = 8/condition/assay). On day 0, cells were plated; on day 1, drugs were added in 4-fold dilutions. The highest dose of gemcitabine was 2,000 nmol/L. Warfarin was used at 2 µM. On day 5, the relative cell number was estimated use MTS (Promega; final concentration, 333 µg/ml); plates were incubated for 1 to 3 h at 37° C. and read at 490 nm. Drug sensitivity curves and $IC_{50}$ values were calculated using in-house software. The median $IC_{50}$ +/− SD (nmol/L) for gemcitabine alone and gemcitabine + warfarin and fold reduction in presence of warfarin are displayed.

Example 6

Discussion

Thse data show that warfarin exerts its anti-cancer effects by inhibiting Gas6-mediated Axl activation on tumor cells. The inventors found that Gas6-Axl signal transduction is required to maintain epithelial-mesenchymal plasticity traits of aggressive pancreatic tumors comprising tumorigenicity, invasiveness, survival, drug sensitivity and metastasis. EMT gene expression patterns are apparent early in pancreatic cancer development, associated with inflammatory pre-malignant lesions, and drive early metastatic spread. Inflammatory mediators such as TGFβ that induce EMT transcription factor-mediated gene reprogramming are prominent in malignant pancreatic cancer. Consistent with this, Axl expression is elevated by EMT transcription factors in breast and lung epithelial cells (Gjerdrum et al., 2010; Wilson et al., 2014; Byers et al., 2013). Further, Axl expression is associated with EMT gene signatures in drug resistant NSCLC and a requisite effector of EMT-related acquired resistance to various therapeutics (Wilson et al., 2014). The wide spread expression of Axl in advanced cancer from diverse cellular origins suggests that tumor cell associated Axl is a fundamental contributor to malignant progression. Inhibition of Axl signaling is associated with loss of malignant traits including cell migration and metastasis (Gjerdrum et al., 2010). Congruently, the inventors show that low dose warfarin treatment and tumor-specific Axl selective targeting potently block metastasis in several models of PDA. This is associated with a loss of mesenchymal protein expression and EMT transcription factor expression that result in decreased proliferation and increased apoptosis.

These results demonstrate that low dose warfarin-mediated Axl inhibition is effective as an anti-cancer agent without associated complications from anti-coagulation. These results strongly suggest that the anecdotal anti-tumor effects observed clinically with coumarin-based anti-coagulants are due in part to specific inhibition of Gas6-mediated Axl activation on tumor cells. These results are consistent with recent studies that show γ-carboxylation of Gas6 is required for Gas6-mediated Axl activation (Lew et al., 2014). Further, Paolino et al. (2014) demonstrated that low dose warfarin treatment (0.5 mg/L in drinking water) inhibits Gas6-mediated activation of TAM receptors, Tyro3, Axl and Mer (aka Mertk) on natural killer (NK) cells, leading to enhanced NK cell anti-tumor activity in a murine mammary adenocarcinoma (4T1) model system. The inventors have previously shown that tumor selective Axl inhibition is sufficient to block metastasis in the 4T1 model (Byers et al., 2013). Hence, the effects of systemic Axl inhibition may exert anti-tumor effects through tumor and host-response dependent mechanisms. On the other hand, while each of the animal models the inventors employed has an intact NK compartment, they did not observe any anti-tumor activity in Axl-negative Capan-1 cells suggesting minimal NK cell anti-tumor activity in these models. Taken together, these results of tumor-selective Axl inhibition in multiple settings suggests that inhibition of tumor cell Axl tyrosine kinase activity is a critical determinant for the observed efficacy of warfarin in cancer patients.

Although the present disclosure and its advantages have been described in detail, it should be understood that various changes, substitutions and alterations can be made herein without departing from the disclosure as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

IV. References

All patents and publications mentioned in the specifications are indicative of the levels of those skilled in the art to which the disclosure pertains. All patents and publications are herein incorporated by reference to the same extent as if each individual publication was specifically and individually indicated to be incorporated by reference.

Remington's Pharmaceutical Sciences, 18th Ed. Mack Printing Company, 1990.
Aguilera et al. (2014). *Cancer Res* 74: 1032-1044.
Aguirre et al. (2003). *Genes & Development* 17: 3112-3126.
Becker et al. (2014). *World Journal of Gastroenterology: WJG* 20: 11182-11198.
Becker et al. (2012). *PLoS One* 7: e33916.
Ben-Batalla et al. (2013). *Blood* 122: 2443-2452.
Berman et al. (1996). *Cell* 86: 445-452.
Bonner-Weir et al. (2004). *Pediatr Diabetes* 5 Suppl 2: 16-22.
Brown, J. M. (1973). *Cancer Res* 33: 1217-1224.
Burris et al. (1997). *J Clin Oncol* 15: 2403-2413.
Byers et al. (2013). *Clin Cancer Res* 19: 279-290.
Cook et al. (2012). *Drug Discov Today* 17: 253-260.
Dignard et al. (2008). *Eukaryot Cell* 7: 1591-1599.
Dineen et al. (2010). *Cancer Res* 70: 2852-2861.
Distler et al. (2014). *Biomed Res Int* 2014: 474905.
Dohlman et al. (1996). *Mol Cell Biol* 16: 5194-5209.
Dunne et al. (2014). *Clin Cancer Res* 20: 164-175.
Frese et al. (2012). *Cancer Discov* 2: 260-269.
Gjerdrum et al. (2010). *Proc. Nat'l Acad. Sci. USA* 107: 1124-1129.
Goldstein et al. (2015). *J Natl Cancer Inst* 107.
Hezel et al. (2006). *Genes & Development* 20: 1218-1249.
Holland et al. (2010). *Cancer Res* 70: 1544-1554.
Hruban et al. (2000). *Clin Cancer Res* 6: 2969-2972.
Huang et al. (2014). *Oncogene* 33: 532-535.
Huang et al. (2006). *Comp Hepatol* 5: 8.

Iacobuzio-Donahue et al. (2012). *Clinical cancer research: an official journal of the American Association for Cancer Research* 18: 4257-4265.
Ibrahim et al. (2002). *Clin Cancer Res* 8: 1038-1044.
Jeng et al. (2012). *Nat Commun* 3: 1168.
Kahn, R. A. (2014). *Cell Logist* 4: e943602.
Kawaguchi et al. (2002). *Nature Genetics* 32: 128-134.
Kim et al. (2010). *Tumor Biol* 31: 541-548.
Kirane et al. (2015). *Cancer Res.* 75(18):3699-705.
Kopp et al. (2012). *Cancer Cell* 22: 737-750.
Krah et al. (2015). *Elife* 4.
Kutluk Cenik et al. (2013). *Mol Cancer Ther* 12: 992-1001.
Lew et al. (2014). *Elife* 3.
Linger et al. (2008). *Advances in Cancer Research* 100: 35-83.
Maitra et al. (2005). *Adv Anat Pathol* 12: 81-91.
Masellis et al. (2009). *Int J Clin Oncol* 14: 478-481.
McCulloch, P. and W. D. George (1987). *Br J Surg* 74: 879-883.
Moorcraft et al. (2014). *Clin Colorectal Cancer* 13: 232-238.
Neesse et al. (2014). *Gut* 63: 974-983.
Ostapoff et al. (2013). *Mol Cancer Ther* 12: 1190-1201.
Ostapoff et al. (2014). *Cancer Res* 74: 4996-5007.
Paccez et al. (2013). *Oncogene* 32: 689-698.
Pannala et al. (2008). *Gastroenterology* 134: 981-987.
Paolino et al. (2014). *Nature* 507: 508-512.
Pashkov et al. (2011). *J Biol Chem* 286: 15116-15125.
Pylayeva-Gupta et al. (2011). *Nat Rev Cancer* 11: 761-774.
Rahib et al. (2014). *Cancer Res* 74: 2913-2921.
Rebours et al. (2015). *Clin Cancer Res.* 21(15):3522-8.
Reichl et al. (2014). *Int J Cancer.* 137(2) 385-394/
Ross, E. M. and T. M. Wilkie (2000). *Annual Review of Biochemistry* 69: 795-827.
Rovira et al. (2010). *Proc Natl Acad Sci USA* 107: 75-80.
Schmidt et al., (2012). *Cellular and Molecular Life Sciences: CMLS* 69: 1391-1414.
Schulman, S. and P. Lindmarker (2000). *N Engl J Med* 342: 1953-1958.
Siegel et al., (2015). *CA Cancer J Clin* 65: 5-29.
Soderblom et al., (2015). *Eneuro* 2.
Song et al., (2011). *Cancer* 117: 734-743.
Stephen et al., (2014). *Cancer Cell* 25: 272-281.
Team, R. C. (2014). R: A language and environment for statistical computing. RDC Team.
Tomasetti, C. and B. Vogelstein (2015). *Science* 347: 78-81.
Trapnell et al., (2009). *Bioinformatics* 25: 1105-1111.
Trapnell et al., (2012). *Nat Protoc* 7: 562-578.
Trapnell et al., (2010). *Nat Biotechnol* 28: 511-515.
van Biesen et al., (1995). *Nature* 376: 781-784.
Villasenor et al., (2010). *Dis Model Mech* 3: 567-580.
von Figura et al., (2014). *Nature Cell Biology* 16: 255-267.
Von Hoff et al., (2013). *The New England Journal of Medicine* 369: 1691-1703.
Warnes et al., (2015). gplots: Various R Programming Tools for Plotting Data. *R PAckage Version.*
Wu et al., (2011). *Science Translational Medicine* 3: 92ra66.
Xu et al., (2008). *Cell* 132: 197-207.
Zhang et al., (2012). *Nat Genet* 44: 852-860.
Brown J M. Cancer Res. 1973; 33:1217-24.
McCulloch P, George W D. Br J Surg. 1987; 74:879-83.
Schulman S, Lindmarker P. Duration of Anticoagulation Trial. The New England journal of medicine. 2000; 342: 1953-8.
Song et al., Cancer. 2011; 117:734-43.
Nakano et al., The Biochemical Journal. 1997; 323 (Pt 2):387-92.
Hafizi S, Dahlback B. FEBS J. 2006; 273:5231-44.
Hasanbasic et al., Journal of Thrombosis and Haemostasis: JTH. 2005; 3:2790-7.
Varnum et al., Nature. 1995; 373:623-6.
Tsou et al., J Biol Chem. 2014; 289:25750-63.
Paolino et al., Nature. 2014; 507:508-12.
Melisi et al., Mol Cancer Ther. 2008; 7:829-40.
Ostapoff et al., Cancer Res. 2014.
Sawabu et al., Mol Carcinog. 2007; 46:155-64.
Holland et al., Cancer Res. 2010; 70:1544-54.
Ruan et al., The EMBO Journal. 2012; 31:1692-703.
Gjerdrum et al., Proc Natl Acad Sci USA. 2010; 107:1124-9.
Rhim et al., Cell. 2012; 148:349-61.
Arumugam et al., Cancer Res. 2009; 69:5820-8.
Wilson et al., Cancer Res. 74(20):5878-90, 2014.
Byers et al., Clin Cancer Res. 2013; 19:279-90.
Lew et al., Elife. 2014; 3.
Karlen et al., BMC Bioinformatics. 2007; 8:1-16.
Lee et al., Nature Methods. 2007; 4:359-65.

---

What is claimed:

1. A transgenic mouse whose genome comprises:
a transgene encoding G-Protein Signaling protein (Rgs) 16 operably linked to green fluorescent protein (GFP) and a Cre-mediated mutant Kras$^{G12D}$ knock-in allele under the control of a p48(Ptf1a) promoter, wherein the transgene is a Kras$^{G12D}$-dependent marker and wherein the GFP fluorescence can be detected between postnatal day (P) P15 to P29 in mouse early pancreatic ductal adenocarcinoma (PDA) tumors.

2. A transgenic mouse whose genome comprises:
a transgene encoding G-Protein Signaling protein (Rgs) 16 operably linked to green fluorescent protein (GFP), a Cre-mediated mutant Kras$^{G12D}$ knock-in allele under the control of a p48(Ptf1a) promoter, and a functional disruption of the tumor suppressor Cdkn2a, wherein the transgene is a Kras$^{G12D}$-dependent marker and wherein the GFP fluorescence can be detected between day (P) P15 and P29 in mouse early pancreatic ductal adenocarcinoma (PDA) tumors.

3. A transgenic mouse whose genome comprises:
a functional disruption of both endogenous Rgs16 and Rgs8 genes and a Cre-mediated Kras$^{G12D}$ knock-in allele under the control of a p48 (Ptf1a) promoter, wherein the mouse exhibits faster and more aggressive early pancreatic ductal adeonocarcinoma (PDA) tumor initiation and progression to aggressive metastasis to liver and lung relative to the same transgenic mouse lacking the functional disruption of both endogenous Rgs16 and Rgs8 genes.

\* \* \* \* \*

UNITED STATES PATENT AND TRADEMARK OFFICE
CERTIFICATE OF CORRECTION

PATENT NO. : 9,986,723 B2
APPLICATION NO. : 14/920195
DATED : June 5, 2018
INVENTOR(S) : Thomas M. Wilkie et al.

It is certified that error appears in the above-identified patent and that said Letters Patent is hereby corrected as shown below:

In the Specification

Column 1, Line 10, insert:
--This invention was made with government support under grant number R21 CA161624 awarded by The National Institutes of Health. The government has certain rights in the invention.--.

Signed and Sealed this
Fourth Day of August, 2020

Andrei Iancu
*Director of the United States Patent and Trademark Office*